US011376325B2

(12) United States Patent
Reed et al.

(10) Patent No.: US 11,376,325 B2
(45) Date of Patent: *Jul. 5, 2022

(54) METHOD OF INDUCING AN IMMUNE RESPONSE USING AN EXPRESSION CONSTRUCT AND GLA

(71) Applicant: ACCESS TO ADVANCED HEALTH INSTITUTE, Seattle, WA (US)

(72) Inventors: Steven G. Reed, Bellevue, WA (US); Darrick Carter, Seattle, WA (US)

(73) Assignee: ACCESS TO ADVANCED HEALTH INSTITUTE, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/899,729

(22) Filed: Jun. 12, 2020

(65) Prior Publication Data

US 2020/0376116 A1  Dec. 3, 2020

Related U.S. Application Data

(63) Continuation of application No. 15/868,460, filed on Jan. 11, 2018, now abandoned, which is a continuation of application No. 14/849,212, filed on Sep. 9, 2015, now abandoned, which is a continuation of application No. 13/886,666, filed on May 3, 2013, now abandoned, which is a continuation of application No. 12/843,398, filed on Jul. 26, 2010, now abandoned, which is a continuation of application No. 12/843,395, filed on Jul. 26, 2010, now abandoned, which is a continuation of application No. 12/351,710, filed on Jan. 9, 2009, now abandoned, which is a continuation of application No. 12/134,127, filed on Jun. 5, 2008, now abandoned, which is a continuation-in-part of application No. 12/154,663, filed on May 22, 2008, now abandoned, which is a continuation of application No. 11/862,122, filed on Sep. 26, 2007, now Pat. No. 8,273,361.

(60) Provisional application No. 60/847,404, filed on Sep. 26, 2006.

(51) Int. Cl.
| | | |
|---|---|---|
| A61K 39/395 | (2006.01) | |
| A61K 39/39 | (2006.01) | |
| A61K 39/008 | (2006.01) | |
| A61K 45/06 | (2006.01) | |
| A61K 39/04 | (2006.01) | |
| A61K 39/145 | (2006.01) | |
| A61K 39/00 | (2006.01) | |
| C12N 7/00 | (2006.01) | |

(52) U.S. Cl.
CPC .......... *A61K 39/39* (2013.01); *A61K 39/0005* (2013.01); *A61K 39/008* (2013.01); *A61K 39/04* (2013.01); *A61K 39/145* (2013.01); *A61K 45/06* (2013.01); *C12N 7/00* (2013.01); *A61K 2039/53* (2013.01); *A61K 2039/55566* (2013.01); *A61K 2039/55572* (2013.01); *A61K 2039/57* (2013.01); *C12N 2760/16034* (2013.01); *C12N 2760/16071* (2013.01); *Y02A 50/30* (2018.01)

(58) Field of Classification Search
None
See application file for complete search history.

(56) References Cited

U.S. PATENT DOCUMENTS

| | | | | |
|---|---|---|---|---|
| 8,343,512 B2 * | 1/2013 | Reed | ...................... | A61K 39/39 424/275.1 |
| 8,609,114 B2 * | 12/2013 | Reed | ...................... | A61P 31/16 424/278.1 |
| 9,907,845 B2 * | 3/2018 | Reed | ...................... | A61K 39/39 |
| 10,792,359 B2 * | 10/2020 | Reed | .................... | A61K 39/145 |
| 2004/0121924 A1 * | 6/2004 | Hong | .................... | A61L 12/142 510/112 |
| 2005/0123550 A1 * | 6/2005 | Laurent | .................. | A61K 39/39 424/184.1 |

OTHER PUBLICATIONS

Imoto et al. Proc. Japan Acad. vol. 60 No. 8J pp. 285-288 (Year: 1984).*

* cited by examiner

*Primary Examiner* — Yunsoo Kim
(74) *Attorney, Agent, or Firm* — Newport IP, LLC; Benjamin A. Keim

(57) ABSTRACT

Compositions and methods, including vaccines and pharmaceutical compositions for inducing or enhancing an immune response are disclosed based on the discovery of useful immunological adjuvant properties in a synthetic, glucopyranosyl lipid adjuvant (GLA) that is provided in substantially homogeneous form. Chemically defined, synthetic GLA offers a consistent vaccine component from lot to lot without the fluctuations in contaminants or activity that compromise natural-product adjuvants. Also provided are vaccines and pharmaceutical compositions that include GLA and one or more of an antigen, a Toll-like receptor (TLR) agonist, a co-adjuvant and a carrier such as a pharmaceutical carrier.

9 Claims, 28 Drawing Sheets

Figure 1:
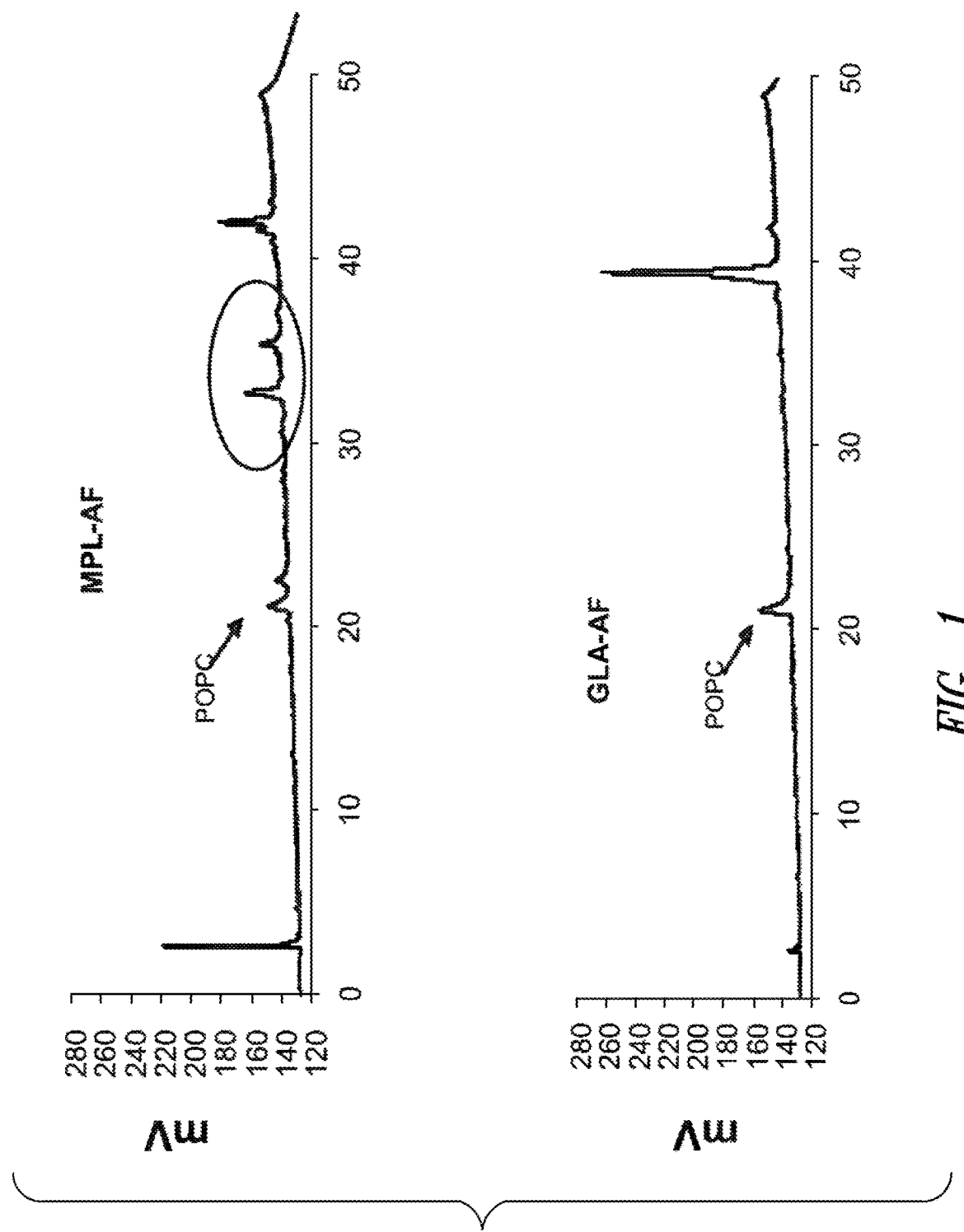
Figure 2A:
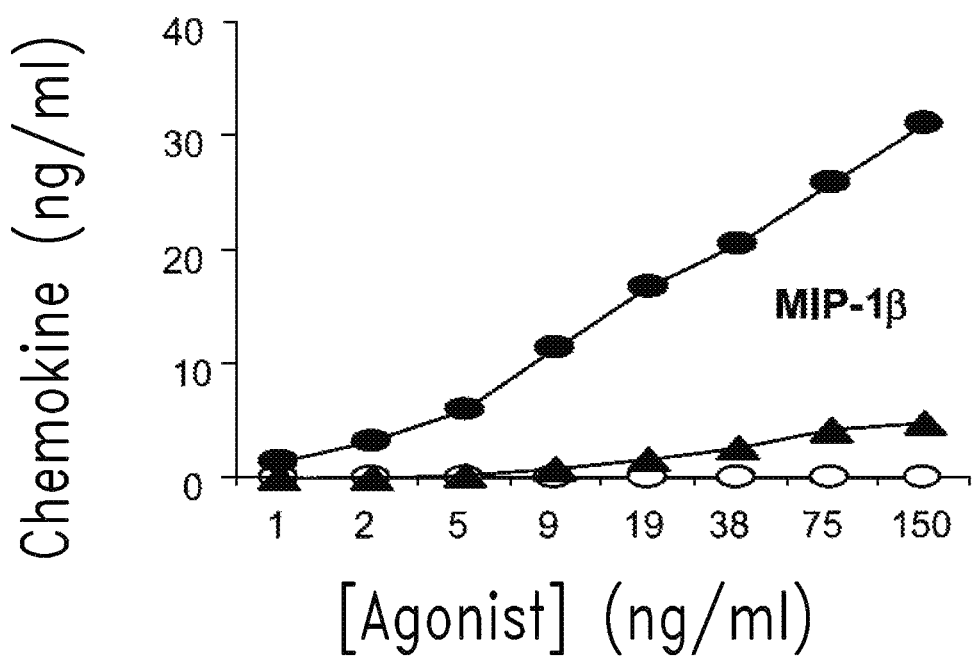
Figure 2B:
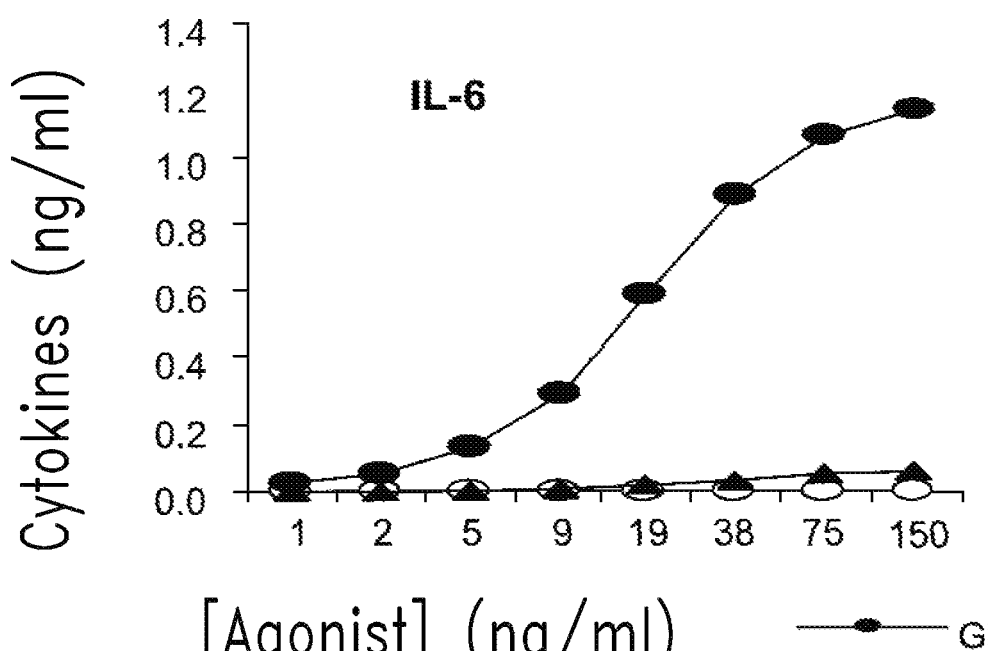
Figure 2C:
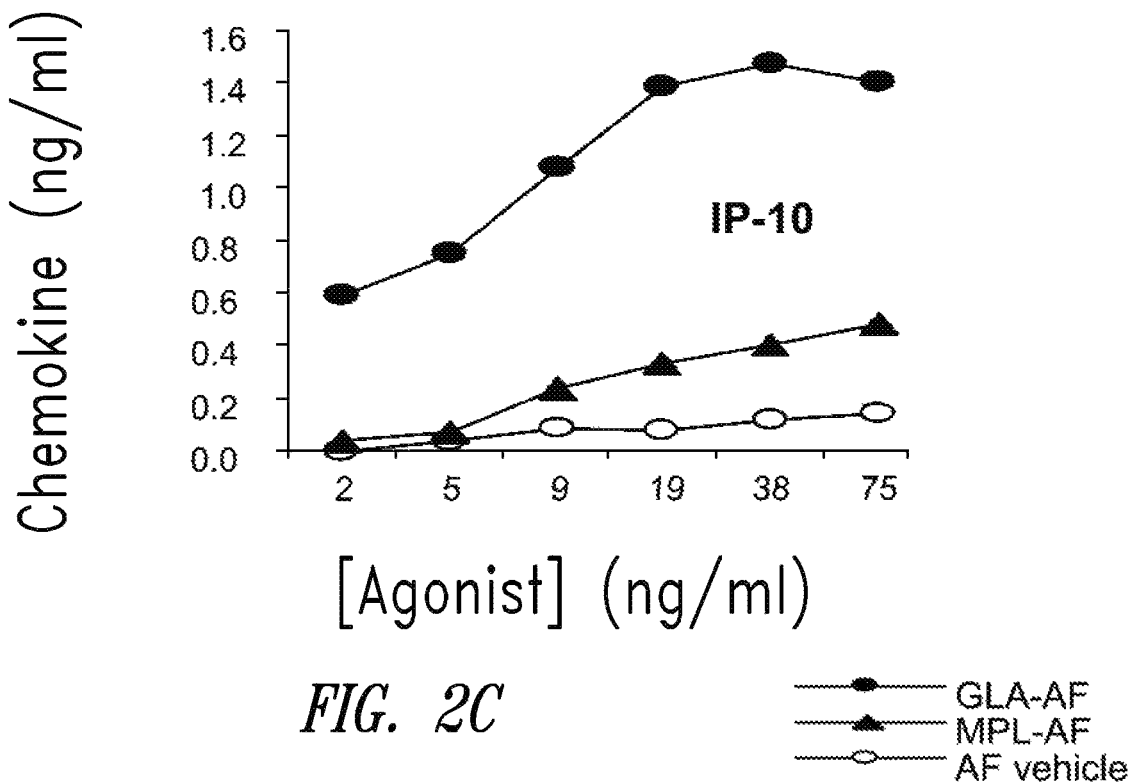
Figure 2D:
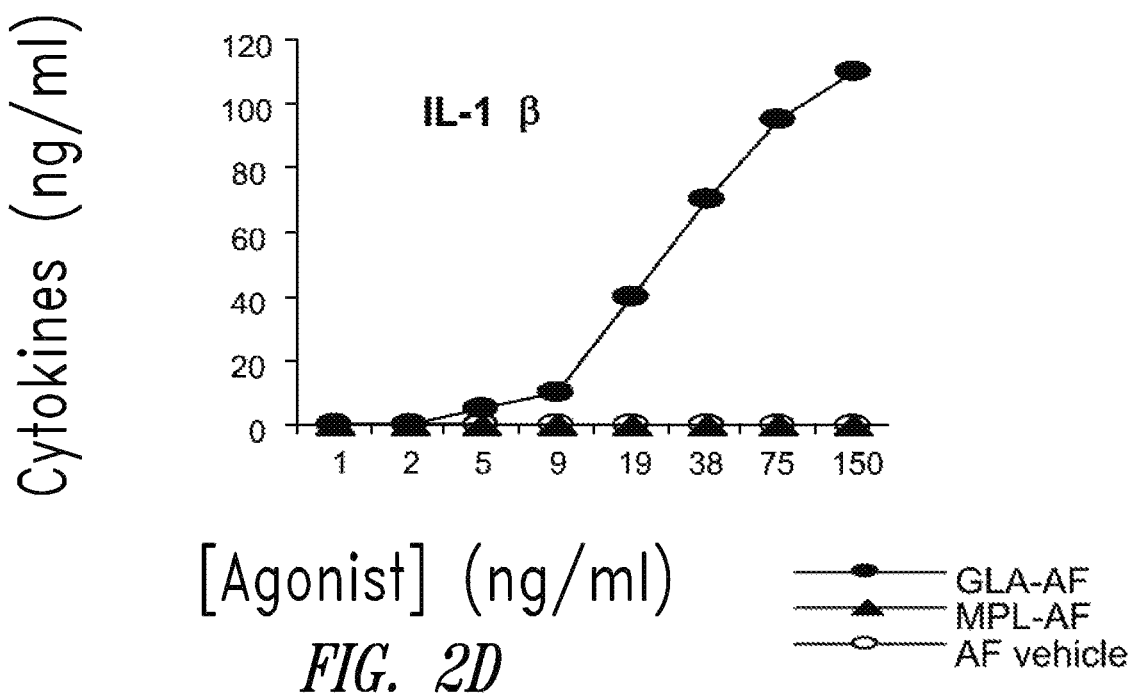
Figure 2E:
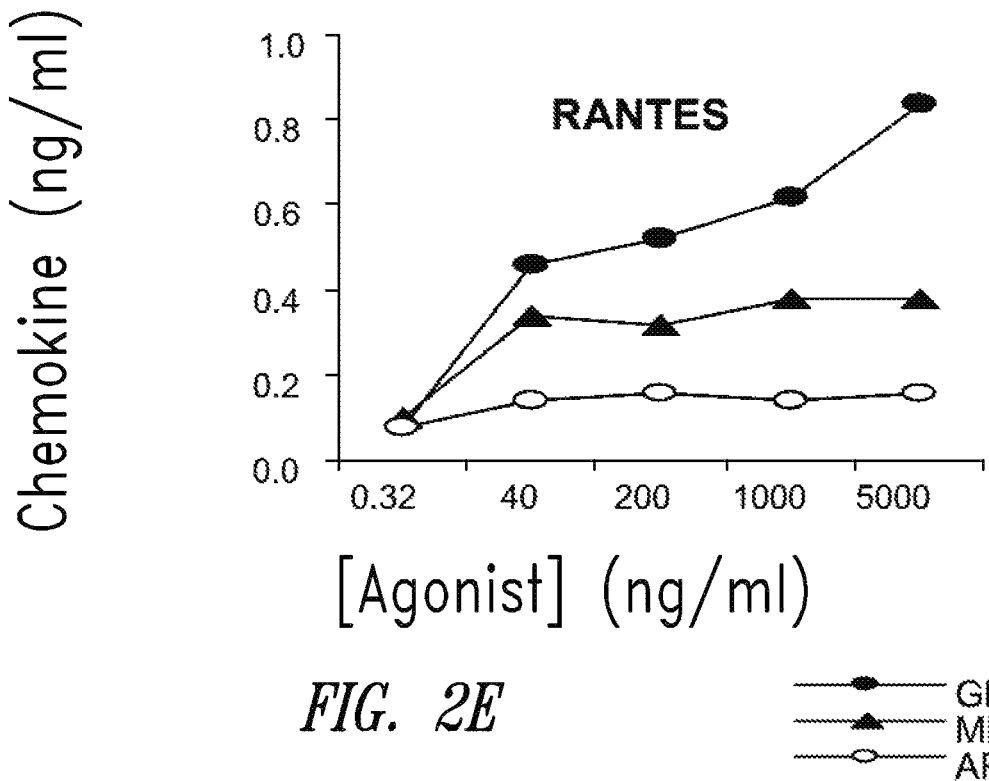
Figure 2F:
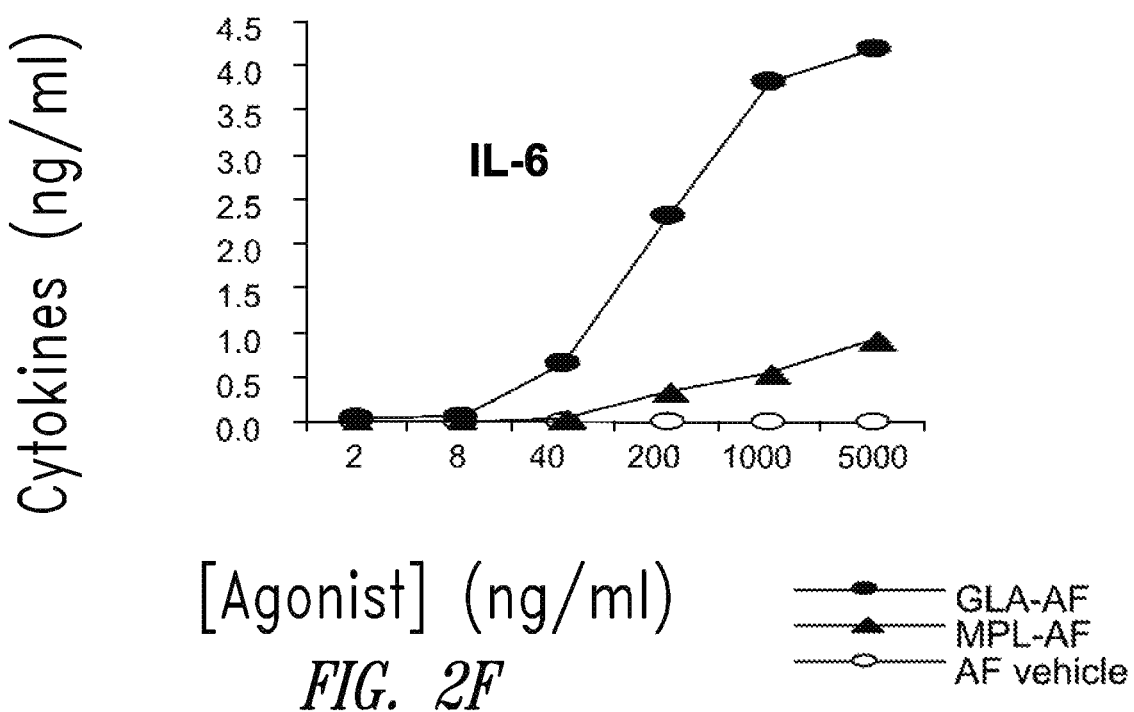
Figure 2G:
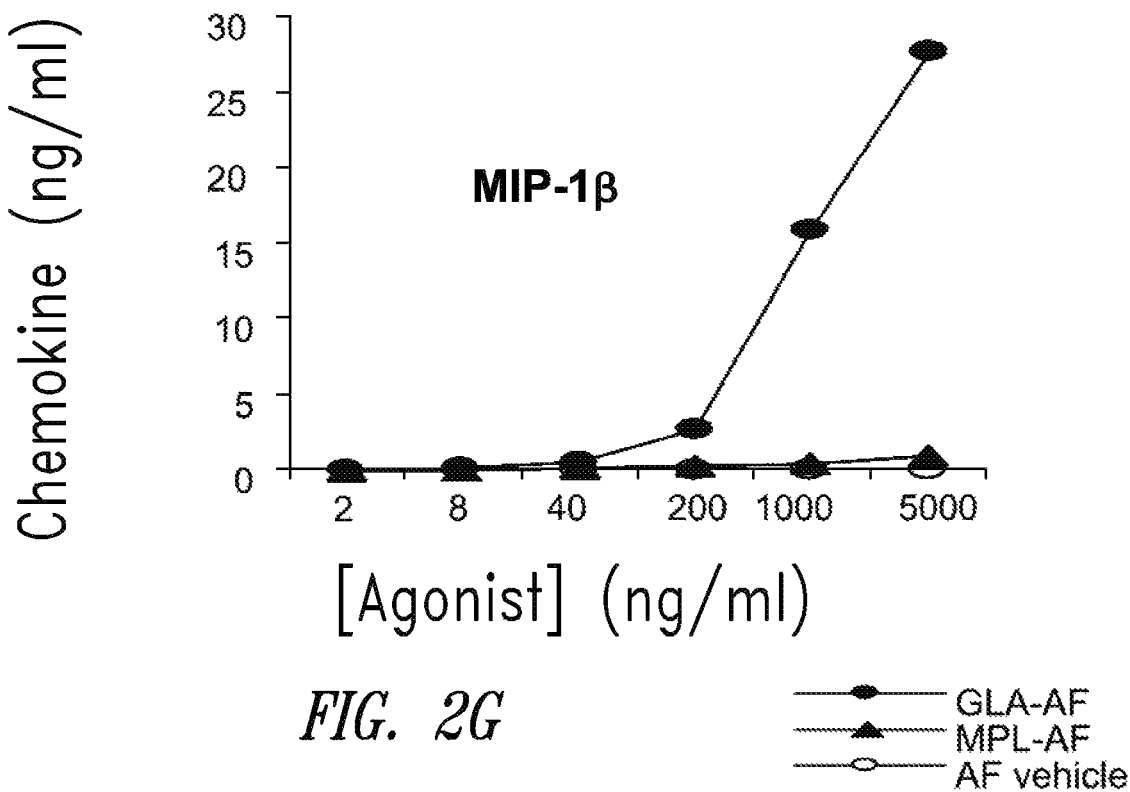
Figure 2H:
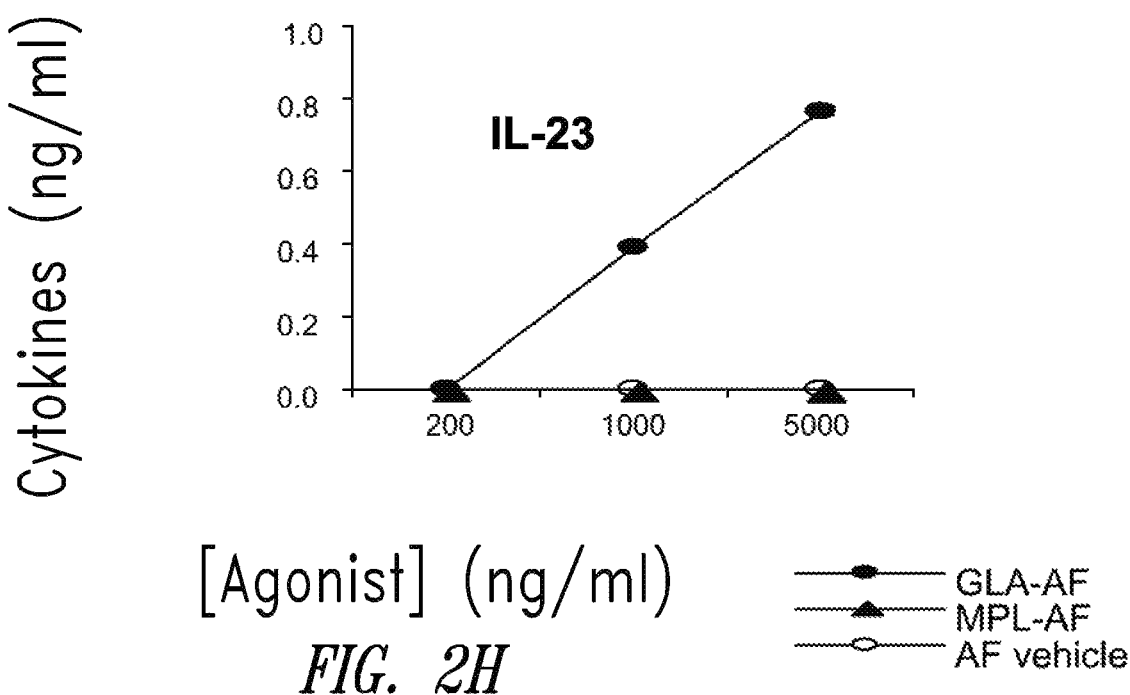

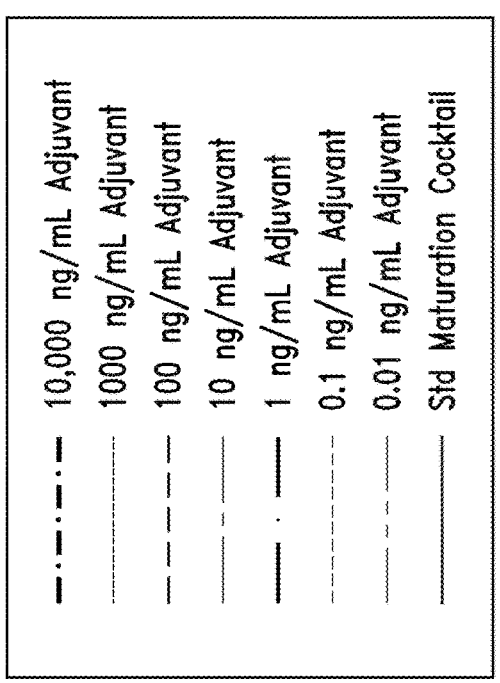
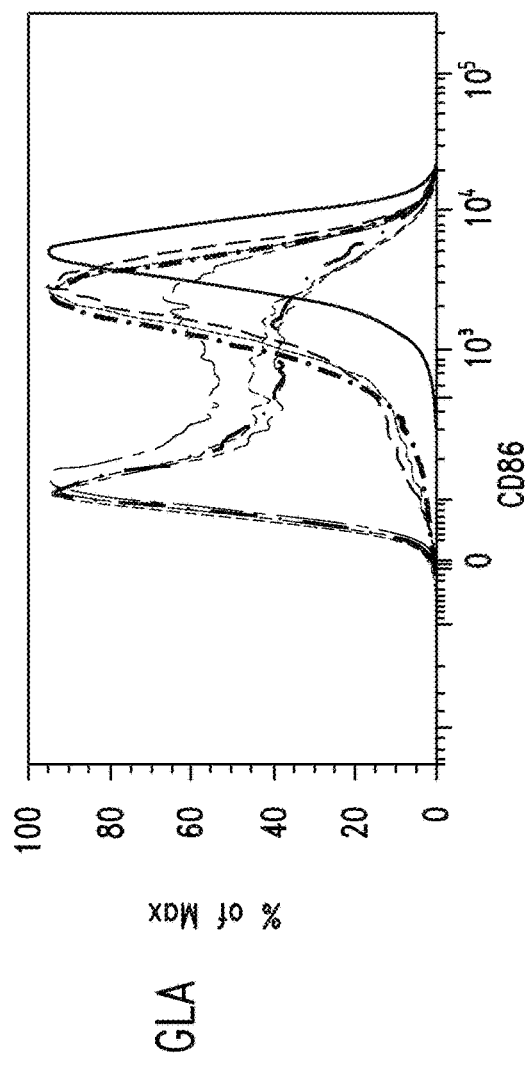
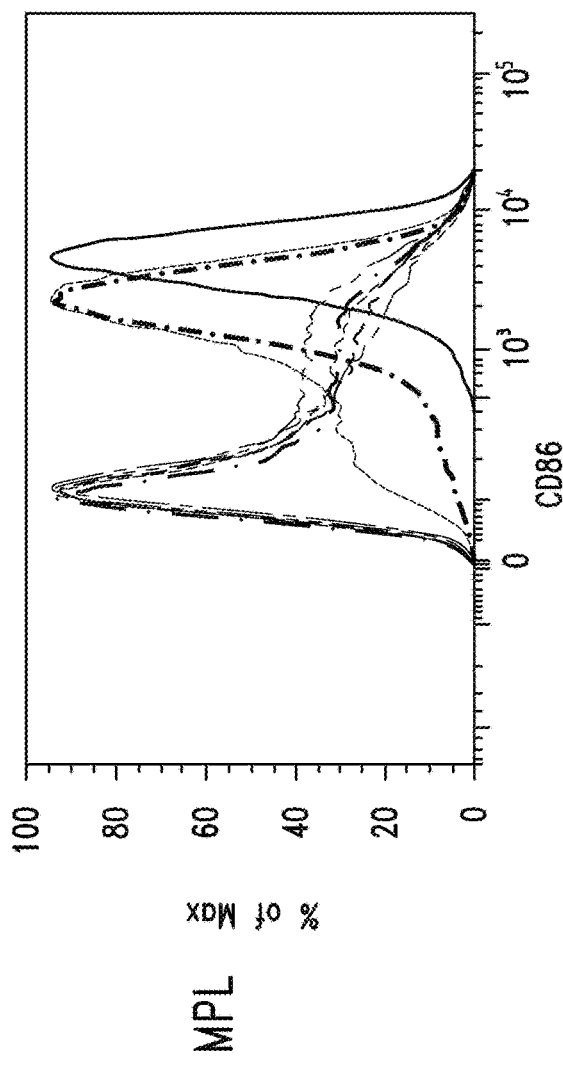
FIG. 9A
FIG. 9B

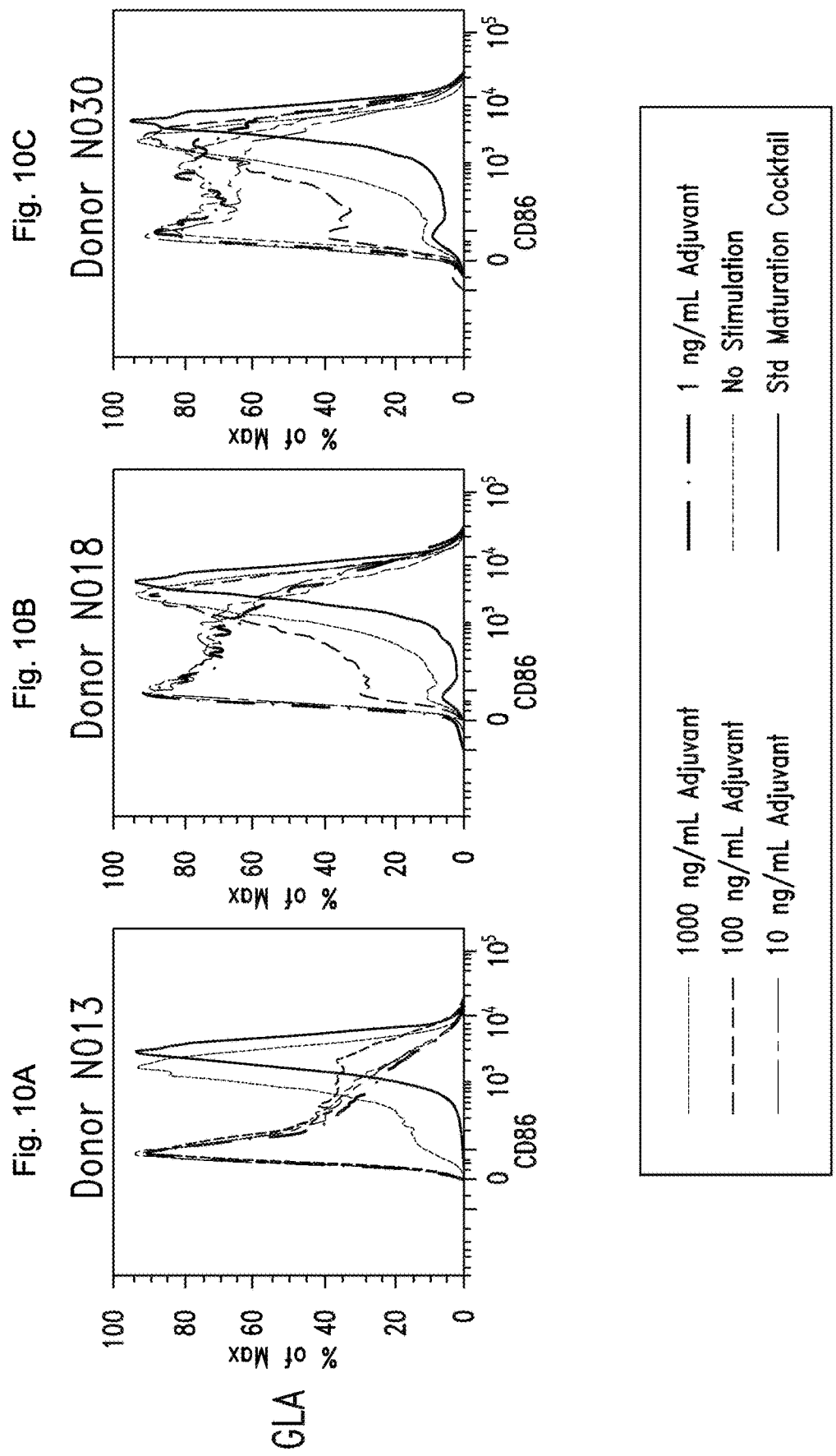

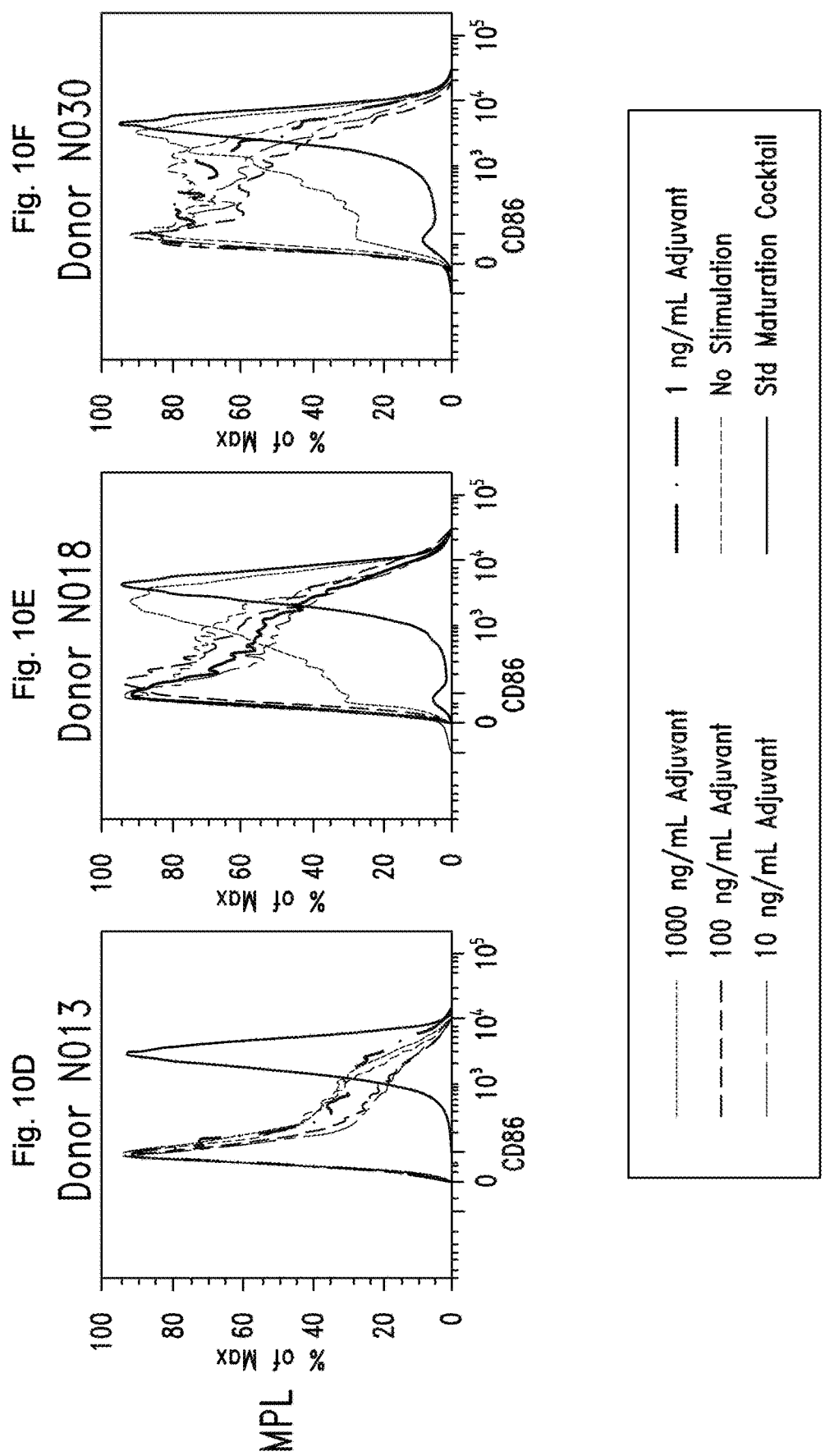

METHOD OF INDUCING AN IMMUNE RESPONSE USING AN EXPRESSION CONSTRUCT AND GLA

CROSS-REFERENCE TO RELATED APPLICATION

This application is a continuation of U.S. patent application Ser. No. 14/849,212 filed Sep. 9, 2015, which is a continuation of U.S. application Ser. No. 13/886,666 filed May 3, 2013, which is a continuation of U.S. patent application Ser. No. 12/843,398, filed Jul. 26, 2010, which is a continuation of U.S. patent application Ser. No. 12/351,710, filed Jan. 9, 2009; which is a continuation of U.S. patent application Ser. No. 12/134,127 filed Jun. 5, 2008; and a continuation-in-part of U.S. patent application Ser. No. 12/154,663, filed May 22, 2008; and a continuation-in-part of U.S. patent application Ser. No. 11/862,122, filed Sep. 26, 2007, now U.S. Pat. No. 8,273,361, which claims the benefit under 35 U.S.C. § 119(e) of U.S. Provisional Patent Application No. 60/847,404 filed Sep. 26, 2006; all of these applications are incorporated herein by reference in their entireties.

STATEMENT OF GOVERNMENT INTEREST

This invention was made in part with government support under Grant No. AI-25038 awarded by the National Institutes of Health. The government has certain rights in this invention.

BACKGROUND OF THE INVENTION

Field of the Invention

The present invention relates to the field of pharmaceutical and vaccine compositions. More specifically, embodiments described herein relate to pharmaceutical and vaccine compositions, as well as related prophylactic and therapeutic methods, wherein the compositions comprise a glucopyranosyl lipid adjuvant (GLA).

Description of the Related Art

The immune system of higher organisms has been characterized as distinguishing foreign agents (or "non-self") agents from familiar or "self" components, such that foreign agents elicit immune responses while "self" components are ignored or tolerated. Immune responses have traditionally been characterized as either humoral responses, in which antibodies specific for antigens are produced by differentiated B lymphocytes known as plasma cells, or cell mediated responses, in which various types of T lymphocytes act to eliminate antigens by a number of mechanisms. For example, CD4+ helper T cells that are capable of recognizing specific antigens may respond by releasing soluble mediators such as cytokines to recruit additional cells of the immune system to participate in an immune response. Also, CD8+ cytotoxic T cells that are also capable of specific antigen recognition may respond by binding to and destroying or damaging an antigen-bearing cell or particle. It is known in the immunological arts to provide certain vaccines according to a variety of formulations, usually for the purpose of inducing a desired immune response in a host.

Several strategies for eliciting specific immune responses through the administration of a vaccine to a host include immunization with heat-killed or with live, attenuated infectious pathogens such as viruses, bacteria or certain eukaryotic pathogens; immunization with a non-virulent infective agent capable of directing the expression of genetic material encoding the antigen(s) to which an immune response is desired; and immunization with subunit vaccines that contain isolated immunogens (such as proteins) from a particular pathogen in order to induce immunity against the pathogen. (See, e.g., Liu, 1998 Nature Medicine 4(5 suppl.):515.) For certain antigens there may be one or more types of desirable immunity for which none of these approaches has been particularly effective, including the development of vaccines that are effective in protecting a host immunologically against human immunodeficiency viruses or other infectious pathogens, cancer, autoimmune disease, or other clinical conditions.

It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of Bacterial Endotoxins, Plenum Publ. Corp., NY, p 407-419).

A further detoxified version of MPL results from the removal of the acyl chain from the 3-position of the disaccharide backbone, and is called 3-O-deacylated monophosphoryl lipid A (3D-MPL). It can be purified and prepared by the methods taught in GB 2122204B, which reference also discloses the preparation of diphosphoryl lipid A, and 3-O-deacylated variants thereof. For example, 3D-MPL has been prepared in the form of an emulsion having a small particle size less than 0.2 μm in diameter, and its method of manufacture is disclosed in WO 94/21292. Aqueous formulations comprising monophosphoryl lipid A and a surfactant have been described in WO9843670A2.

Bacterial lipopolysaccharide-derived adjuvants to be formulated in adjuvant combinations may be purified and processed from bacterial sources, or alternatively they may be synthetic. For example, purified monophosphoryl lipid A is described in Ribi et at 1986 (supra), and 3-O-deacylated monophosphoryl or diphosphoryl lipid A derived from *Salmonella* sp. is described in GB 2220211 and U.S. Pat. No. 4,912,094. 3D-MPL and the β(1-6) glucosamine disaccharides as well as other purified and synthetic lipopolysaccharides have been described (WO 98/01139; U.S. Pat. No. 6,005,099 and EP 0 729 473 B1, Hilgers et al., 1986 *Int Arch. Allergy Immunol.*, 79(4):392-6; Hilgers et al., 1987, *Immunology*, 60(1); 141-6; and EP 0 549 074 B1). Combinations of 3D-MPL and saponin adjuvants derived from the bark of *Quillaja Saponaria molina* have been described in EP 0 761 231 B. WO 95/17210 discloses an adjuvant emulsion system based on squalene, α-tocopherol, and polyoxyethylene sorbitan monooleate (TWEEN™-80), formulated with the immunostimulant QS21, and optionally including 3D-MPL. Despite the accessibility of such combinations, the use of adjuvants derived from natural products is accompanied by high production costs, inconsistency from lot to lot, difficulties associated with large-scale production, and uncertainty with respect to the presence of impurities in the compositional make-up of any given preparation.

Clearly there is a need for improved vaccines, and in particular for vaccines that beneficially contain high-purity, chemically defined adjuvant components that exhibit lot-to-lot consistency and that can be manufactured efficiently on an industrial scale without introducing unwanted or structurally undefined contaminants. The present invention provides compositions and methods for such vaccines, and offers other related advantages.

BRIEF SUMMARY OF THE INVENTION

The present invention in its several embodiments is directed to compositions and methods that advantageously employ the synthetic glucopyranosyl lipid adjuvant (GLA) as an adjuvant and vaccine component. According to one embodiment of the invention described herein, there is provided a vaccine composition comprising an antigen and a glucopyranosyl lipid adjuvant (GLA).

In other embodiments there is provided a vaccine composition comprising (a) an antigen; a glucopyranosyl lipid adjuvant (GLA); and a toll-like receptor (TLR) agonist, wherein in certain further embodiments the TLR agonist is selected from lipopolysaccharide, peptidoglycan, polyI:C, CpG, 3M003, flagellin, Leishmania homolog of eukaryotic ribosomal elongation and initiation factor 4a (LeIF) and at least one hepatitis C antigen. In another embodiment there is provided a vaccine composition comprising: an antigen; a glucopyranosyl lipid adjuvant (GLA); and at least one co-adjuvant that is selected from saponins and saponin mimetics. In another embodiment there is provided a vaccine composition comprising an antigen; a glucopyranosyl lipid adjuvant (GLA); and a carrier that comprises at least one of an oil and ISCOMATRIX™. In another embodiment there is provided a vaccine composition comprising an antigen; a glucopyranosyl lipid adjuvant (GLA); and one or more of: (i) at least one co-adjuvant, (ii) at least one TLR agonist, (iii) at least one imidazoquinoline immune response modifier, and (iv) at least one double stem loop immune modifier (dSLIM). In certain further embodiments (i) the co-adjuvant, when present, is selected from alum, a plant alkaloid and a detergent, wherein the plant alkaloid is selected from tomatine and the detergent is selected from saponin, Polysorbate 80, Span 85 and Stearyl tyrosine, (ii) the TLR agonist, when present, is selected from lipopolysaccharide, peptidoglycan, polyI:C, CpG, 3M003, flagellin, Leishmania homolog of eukaryotic ribosomal elongation and initiation factor 4a (LeIF) and at least one hepatitis C antigen, and (iii) the imidazoquinoline immune response modifier, when present, is selected from resiquimod (R848), imiquimod and gardiquimod. In another embodiment there is provided a vaccine composition comprising: an antigen; a glucopyranosyl lipid adjuvant (GLA); and at least one of a co-adjuvant and a pharmaceutically acceptable carrier, wherein: the co-adjuvant is selected from a cytokine, a detergent, and a block copolymer or biodegradable polymer, and the pharmaceutically acceptable carrier comprises a carrier that is selected from calcium phosphate, an oil-in-water emulsion, a water-in-oil emulsion, a liposome, a novosome, a non-ionic surfactant vesicle (e.g., niosome) and a microparticle. In a particular embodiment, where a liposome or similar carrier is used, the GLA is in the laminar structure of the liposome or is encapsulated. In another particular embodiment, where a microparticle is used, the microparticle is one that is based on or comprises polymer fat lipids.

In certain further embodiments the cytokine is selected from GM-CSF, IL-2, IL-7, IL-12, TNF-α and IFN-gamma, the block copolymer or biodegradable polymer is selected from Pluronic L121, CRL1005, PLGA, PLA, PLG, and polyI:C, and the detergent is selected from the group consisting of saponin, Polysorbate 80, Span 85 and Stearyl tyrosine.

In other embodiments there is provided a vaccine composition comprising: at least one recombinant expression construct which comprises a promoter operably linked to a nucleic acid sequence encoding an antigen; and a glucopyranosyl lipid adjuvant (GLA). In one embodiment the recombinant expression construct is present in a viral vector, which in certain further embodiments is present in a virus that is selected from an adenovirus, an adeno-associated virus, a herpesvirus, a lentivirus, a poxvirus, and a retrovirus.

According to certain of any of the above described embodiments, the GLA is not 3'-de-O-acylated. According to certain of any of the above described embodiments, the GLA comprises: (i) a diglucosamine backbone having a reducing terminus glucosamine linked to a non-reducing terminus glucosamine through an ether linkage between hexosamine position 1 of the non-reducing terminus glucosamine and hexosamine position 6 of the reducing terminus glucosamine; (ii) an O-phosphoryl group attached to hexosamine position 4 of the non-reducing terminus glucosamine; and (iii) up to six fatty acyl chains; wherein one of the fatty acyl chains is attached to 3-hydroxy of the reducing terminus glucosamine through an ester linkage, wherein one of the fatty acyl chains is attached to a 2-amino of the non-reducing terminus glucosamine through an amide linkage and comprises a tetradecanoyl chain linked to an alkanoyl chain of greater than 12 carbon atoms through an ester linkage, and wherein one of the fatty acyl chains is attached to 3-hydroxy of the non-reducing terminus glucosamine through an ester linkage and comprises a tetradecanoyl chain linked to an alkanoyl chain of greater than 12 carbon atoms through an ester linkage.

According to certain of any of the above described embodiments that include a TLR agonist, the TLR agonist is capable of delivering a biological signal by interacting with at least one TLR that is selected from TLR-2, TLR-3, TLR-4, TLR-5, TLR-6, TLR-7, TLR-8 and TLR-9. In certain further embodiments the TLR agonist is selected from lipopolysaccharide, peptidoglycan, polyI:C, CpG, 3M003, flagellin, Leishmania homolog of eukaryotic ribosomal elongation and initiation factor 4a (LeIF) and at least one hepatitis C antigen. In a particular embodiment, where a TLR-7 and/or TLR-8 agonist is used, the TLR-7 and/or TLR-8 agonist is entrapped within a vesicle.

According to certain of any of the above described embodiments, the GLA has the formula:

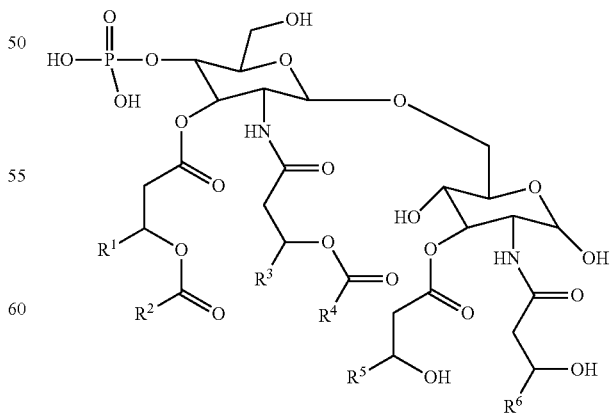

where: $R^1$, $R^3$, $R^5$ and $R^6$ are $C_{11}$-$C_{20}$ alkyl; and $R^2$ and $R^4$ are $C_{12}$-$C_{20}$ alkyl.

According to certain of any of the above described embodiments, the vaccine composition is capable of eliciting an immune response in a host. In certain further embodiments the immune response is specific for the antigen. According to certain of any of the above described embodiments, the antigen is capable of eliciting in a host an immune response that is selected from a humoral response and a cell-mediated response. According to certain of any of the above described embodiments, the vaccine composition is capable of eliciting in a host at least one immune response that is selected from a $T_H1$-type T lymphocyte response, a $T_H2$-type T lymphocyte response, a cytotoxic T lymphocyte (CTL) response, an antibody response, a cytokine response, a lymphokine response, a chemokine response, and an inflammatory response. According to certain of any of the above described embodiments, the vaccine composition is capable of eliciting in a host at least one immune response that is selected from (a) production of one or a plurality of cytokines wherein the cytokine is selected from interferon-gamma (IFN-γ), tumor necrosis factor-alpha (TNF-α), (b) production of one or a plurality of interleukins wherein the interleukin is selected from IL-1, IL-2, IL-3, IL-4, IL-6, IL-8, IL-10, IL-12, IL-13, IL-16, IL-18 and IL-23, (c) production one or a plurality of chemokines wherein the chemokine is selected from MIP-1a, MIP-1β, RANTES, CCL4 and CCL5, and (d) a lymphocyte response that is selected from a memory T cell response, a memory B cell response, an effector T cell response, a cytotoxic T cell response and an effector B cell response.

According to certain of any of the above described embodiments, the antigen is derived from at least one infectious pathogen that is selected from a bacterium, a virus, and a fungus.

In certain further embodiments the bacterium is an *Actinobacterium*, and in certain still further embodiments the *Actinobacterium* is a *Mycobacterium*. In certain other related embodiments the *Mycobacterium* is selected from *M. tuberculosis* and *M. leprae*. In certain other related embodiments the bacterium is selected from *Salmonella, Neisseria, Borrelia, Chlamydia* and *Bordetella*.

In certain other related embodiments the virus is selected from a herpes simplex virus, a human immunodeficiency virus (HIV), a feline immunodeficiency virus (FIV), cytomegalovirus, Varicella Zoster Virus, hepatitis virus, Epstein Barr Virus (EBV), respiratory syncytial virus, human papilloma virus (HPV) and a cytomegalovirus. According to certain of any of the above described embodiments, the antigen is derived from a human immunodeficiency virus, which in certain further embodiments is selected from HIV-1 and HIV-2.

In certain other related embodiments the fungus is selected from *Aspergillus, Blastomyces, Coccidioides* and *Pneumocystis*. In certain other related embodiments the fungus is a yeast, which in certain further embodiments is a *Candida*, wherein in certain still further embodiments the *Candida* is selected from *C. albicans, C. glabrata, C. krusei, C. lusitaniae, C. tropicalis* and *C. parapsilosis*.

According to certain of any of the above described embodiments, the antigen is derived from a parasite, which in certain further embodiments is a protozoan, which in certain further embodiments is a *Plasmodium*, which in certain still further embodiments is selected from *P. falciparum, P. vivax, P. malariae* and *P. ovale*. In certain other embodiments the parasite is selected from *Acanthamoeba, Entamoeba histolytica, Angiostrongylus, Schistosoma mansonii, Schistosoma haematobium, Schistosoma japonicum, Schistosoma mekongi, Cryptosporidium, Ancylostoma, Entamoeba histolytica, Entamoeba coli, Entamoeba dispar, Entamoeba hartmanni, Entamoeba polecki, Wuchereria bancrofti, Giardia, Leishmania, Enterobius vermicularis, Ascaris lumbricoides, Trichuris trichiura, Necator americanus, Ancylostoma duodenale, Brugia malayi, Onchocerca volvulus, Dracanculus medinensis, Trichinella spiralis, Strongyloides stercoralis, Opisthorchis sinensis, Paragonimus sp, Fasciola hepatica, Fasciola magna, Fasciola gigantica), Taenia saginata* and *Taenia solium*.

According to certain of any of the above described embodiments, the antigen is derived from at least one cancer cell. In certain further embodiments the cancer cell originates in a primary solid tumor, and in certain other embodiments the cancer cell originates in a cancer that is a metastatic or secondary solid tumor, and in certain other embodiments the cancer cell originates in a cancer that is a circulating tumor or an ascites tumor. In certain related embodiments the cancer cell originates in a cancer that is selected from cervical cancer, ovarian cancer, breast cancer, prostate cancer, fibrosarcoma, myxosarcoma, liposarcoma, chondrosarcoma, osteogenic sarcoma, chordoma, angiosarcoma, endotheliosarcoma, lymphangiosarcoma, pseudomyxoma petitonei, lymphangioendotheliosarcoma, synovioma, mesothelioma, Ewing's tumor, leiomyosarcoma, rhabdomyosarcoma, colon carcinoma, pancreatic cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma and Wilms' tumor. In certain other related embodiments the cancer cell originates in a cancer that is selected from testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, Waldenstrom's macroglobulinemia and heavy chain disease.

According to certain of any of the above described embodiments, the antigen is derived from, or is immunologically cross-reactive with, at least one epitope, biomolecule, cell or tissue that is associated with an autoimmune disease. In certain further embodiments the epitope, biomolecule, cell or tissue that is associated with an autoimmune disease is selected from snRNP when the autoimmune disease is systemic lupus erythematosus, at least one of thyroglobulin, thyrotropin receptor and a thyroid epithelial cell when the autoimmune disease is Graves' disease, a platelet when the autoimmune disease is thrombocytopenic purpura, at least one of pemphigus antigen, desmoglein-3, desmoplakin, envoplakin and bullous pemphigoid antigen 1 when the autoimmune disease is pemphigus, myelin basic protein when the autoimmune disease is multiple sclerosis, a pancreatic islet beta cell when the autoimmune disease is type 1 diabetes, and an acetylcholine receptor when the autoimmune disease is myasthenia gravis.

In another embodiment there is provided a pharmaceutical composition for inducing or enhancing an immune response, comprising a glucopyranosyl lipid adjuvant (GLA); and a pharmaceutically acceptable carrier or excipient. In another embodiment there is provided a pharmaceutical composition for inducing or enhancing an immune response comprising an antigen; a glucopyranosyl lipid adjuvant (GLA); and a pharmaceutically acceptable carrier or excipient. In another embodiment there is provided a pharmaceutical composition for inducing or enhancing an immune response comprising an antigen; a glucopyranosyl lipid adjuvant (GLA); a toll-like receptor (TLR) agonist; and a pharmaceutically acceptable carrier or excipient. In a further embodiment the TLR agonist is selected from lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen. In another embodiment there is provided a pharmaceutical composition for inducing or enhancing an immune response comprising: an antigen; a glucopyranosyl lipid adjuvant (GLA); at least one co-adjuvant that is selected from saponins and saponin mimetics; and a pharmaceutically acceptable carrier or excipient. In another embodiment there is provided a pharmaceutical composition for inducing or enhancing an immune response comprising antigen; a glucopyranosyl lipid adjuvant (GLA); and a pharmaceutically acceptable carrier that comprises at least one of an oil and ISCOMATRIX™. In another embodiment there is provided a pharmaceutical composition for inducing or enhancing an immune response comprising: (a) an antigen; (b) a glucopyranosyl lipid adjuvant (GLA); (c) one or more of: (i) at least one co-adjuvant, (ii) at least one TLR agonist, (iii) at least one imidazoquinoline immune response modifier, and (iv) at least one double stem loop immune modifier (dSLIM); and (d) a pharmaceutically acceptable carrier or excipient. In certain further embodiments (i) the co-adjuvant, when present, is selected from alum, a plant alkaloid and a detergent, wherein the plant alkaloid is tomatine and the detergent is selected from saponin, Polysorbate 80, Span 85 and Stearyl tyrosine, (ii) the TLR agonist, when present, is selected from lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen, and (iii) the imidazoquinoline immune response modifier, when present, is selected from resiquimod (R848), imiquimod and gardiquimod.

In another embodiment there is provided a pharmaceutical composition for inducing or enhancing an immune response, comprising: an antigen; a glucopyranosyl lipid adjuvant (GLA); and at least one co-adjuvant; and a pharmaceutically acceptable carrier, wherein: the co-adjuvant is selected from a cytokine, a block copolymer or biodegradable polymer, and a detergent, and the pharmaceutically acceptable carrier comprises a carrier that is selected from calcium phosphate, an oil-in-water emulsion, a water-in-oil emulsion, a liposome, and a microparticle. In certain further embodiments the cytokine is selected from GM-CSF, IL-2, IL-7, IL-12, TNF and IFN-gamma, the block copolymer or biodegradable polymer is selected from Pluronic® L121, CRL1005, PLGA, PLA, PLG, and polyI:C, and the detergent is selected from the group consisting of saponin, Polysorbate 80, Span 85 and Stearyl tyrosine.

In another embodiment there is provided a pharmaceutical composition comprising: at least one recombinant expression construct which comprises a promoter operably linked to a nucleic acid sequence encoding an antigen; a glucopyranosyl lipid adjuvant (GLA); and a pharmaceutically acceptable carrier or excipient. In certain further embodiments the recombinant expression construct is present in a viral vector, which in certain further embodiments is present in a virus that is selected from an adenovirus, an adeno-associated virus, a herpesvirus, a lentivirus, a poxvirus, and a retrovirus.

According to certain further embodiments of the above-described pharmaceutical compositions, the antigen and the GLA are in contact with one another, and according to certain other further embodiments of the above-described pharmaceutical compositions, the antigen and the GLA are not in contact with one another. In certain further embodiments wherein the antigen and the GLA are not in contact with one another, they are present in separate containers. In other embodiments there is provided a pharmaceutical composition for inducing or enhancing an immune response comprising a first combination comprising an antigen and a first pharmaceutically acceptable carrier or excipient; and a second combination comprising a glucopyranosyl lipid adjuvant (GLA) and a second pharmaceutically acceptable carrier or excipient, wherein the antigen and the GLA are not in contact with one another. In a further embodiment the antigen and the GLA are present in separate containers. In certain related embodiments the first pharmaceutically acceptable carrier or excipient is different from the second pharmaceutically acceptable carrier or excipient. In other related embodiments the first pharmaceutically acceptable carrier or excipient is not different from the second pharmaceutically acceptable carrier or excipient.

In another embodiment there is provided a method of treating or preventing an infectious disease in a subject having or suspected of being at risk for having the infectious disease, the method comprising administering to the subject a vaccine composition that comprises (a) an antigen; and (b) a glucopyranosyl lipid adjuvant (GLA), wherein the antigen is derived from, or is immunologically cross-reactive with, at least one infectious pathogen that is associated with the infectious disease, and thereby treating or preventing the infectious disease. In another embodiment there is provided a method of treating or preventing an infectious disease in a subject having or suspected of being at risk for having the infectious disease, the method comprising administering to the subject a vaccine composition that comprises (a) an antigen; (b) a glucopyranosyl lipid adjuvant (GLA); and (c) a toll-like receptor (TLR) agonist, wherein the antigen is derived from, or is immunologically cross-reactive with, at least one infectious pathogen that is associated with the infectious disease, and thereby treating or preventing the infectious disease. In a further embodiment the TLR agonist is selected from lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen. In another embodiment there is provided a method of treating or preventing an infectious disease in a subject having or suspected of being at risk for having the infectious disease, the method comprising administering to the subject a vaccine composition that comprises (a) an antigen; (b) a glucopyranosyl lipid adjuvant (GLA); and (c) at least one co-adjuvant that is selected from the group consisting of saponins and saponin mimetics, wherein the antigen is derived from, or is immunologically cross-reactive with, at least one infectious pathogen that is associated with the infectious disease, and thereby treating or preventing the infectious disease. In another embodiment there is provided a method of treating or preventing an infectious disease in a subject having or suspected of being at risk for having the infectious disease, the method comprising administering to the subject a vaccine composition that comprises (a) an antigen; (b) a glucopyranosyl lipid adjuvant (GLA); and (c) a carrier that comprises at least one of an oil and ISCOMATRIX™, wherein the antigen is derived from, or is immunologically cross-reactive with, at least one infectious pathogen that is associated with the infectious disease, and thereby treating or preventing the infectious disease. In another embodiment there is provided a method of treating or preventing an infectious disease in a subject having or suspected of being at risk for having the infectious disease, the method comprising administering to the subject a vaccine composition that comprises (a) an antigen; (b) a glucopyranosyl lipid adjuvant (GLA); and (c) one or more of: (i) at least one co-adjuvant, (ii) at least one TLR agonist, (iii) at least one imidazoquinoline immune response modifier, and (iv) at least one double stem loop immune modifier (dSLIM), wherein the antigen is derived from, or is immunologically cross-reactive with, at least one infectious pathogen that is associated with the infectious disease, and thereby treating or preventing the infectious disease. In certain further embodiments, (i) the co-adjuvant, when present, is selected from alum, a plant alkaloid and a detergent, wherein the plant alkaloid is tomatine and the detergent is selected from saponin, Polysorbate 80, Span 85 and Stearyl tyrosine, (ii) the TLR agonist, when present, is selected from the group consisting of lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen, and (iii) the imidazoquinoline immune response modifier, when present, is selected from the group consisting of resiquimod (R848), imiquimod and gardiquimod.

In another embodiment there is provided a method of treating or preventing an infectious disease in a subject having or suspected of being at risk for having the infectious disease, the method comprising administering to the subject a vaccine composition that comprises (a) an antigen; (b) a glucopyranosyl lipid adjuvant (GLA); and (c) at least one of a co-adjuvant and a pharmaceutically acceptable carrier, wherein: the co-adjuvant is selected from a cytokine, a block copolymer or biodegradable polymer, and a detergent, and the pharmaceutically acceptable carrier comprises a carrier that is selected from the group consisting of calcium phosphate, an oil-in-water emulsion, a water-in-oil emulsion, a liposome, and a microparticle, wherein the antigen is derived from, or is immunologically cross-reactive with, at least one infectious pathogen that is associated with the infectious disease, and thereby treating or preventing the infectious disease. In certain further embodiments the cytokine is selected from GM-CSF, IL-2, IL-7, IL-12, TNF-α and IFN-gamma, the block copolymer or biodegradable polymer is selected from Pluronic L121, CRL1005, PLGA, PLA, PLG, and polyI:C, and the detergent is selected from the group consisting of saponin, Polysorbate 80, Span 85 and Stearyl tyrosine.

In another embodiment there is provided a method of treating or preventing an infectious disease in a subject having or suspected of being at risk for having the infectious disease, the method comprising administering to the subject a vaccine composition that comprises (a) at least one recombinant expression construct which comprises a promoter operably linked to a nucleic acid sequence encoding an antigen; and (b) a glucopyranosyl lipid adjuvant (GLA), wherein the antigen is derived from, or is immunologically cross-reactive with, at least one infectious pathogen that is associated with the infectious disease, and thereby treating or preventing the infectious disease. In a further embodiment the recombinant expression construct is present in a viral vector, which in certain still further embodiments is present in a virus that is selected from an adenovirus, an adeno-associated virus, a herpesvirus, a lentivirus, a poxvirus, and a retrovirus. According to certain embodiments relating to the above described methods, the antigen is derived from at least one infectious pathogen that is selected from a bacterium, a virus, and a fungus.

In another embodiment there is provided a method of treating or preventing autoimmune disease in a subject having or suspected of being at risk for having an autoimmune disease, the method comprising administering to the subject a vaccine composition that comprises (a) an antigen; and (b) a glucopyranosyl lipid adjuvant (GLA), wherein the antigen is derived from, or is immunologically cross-reactive with, at least one epitope, biomolecule, cell or tissue that is associated with the autoimmune disease, and thereby treating or preventing the autoimmune disease. In another embodiment there is provided a method of treating or preventing an autoimmune disease in a subject having or suspected of being at risk for having an autoimmune disease, the method comprising administering to the subject a vaccine composition that comprises (a) an antigen; (b) a glucopyranosyl lipid adjuvant (GLA); and (c) a toll-like receptor (TLR) agonist, wherein the antigen is derived from, or is immunologically cross-reactive with, at least one epitope, biomolecule, cell or tissue that is associated with the autoimmune disease, and thereby treating or preventing the autoimmune disease. In certain further embodiments the TLR agonist is selected from lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen. In another embodiment there is provided a method of treating or preventing an autoimmune disease in a subject having or suspected of being at risk for having an autoimmune disease, the method comprising administering to the subject a vaccine composition that comprises (a) an antigen; (b) a glucopyranosyl lipid adjuvant (GLA); and (c) at least one co-adjuvant that is selected from the group consisting of saponins and saponin mimetics, wherein the antigen is derived from, or is immunologically cross-reactive with, at least one epitope, biomolecule, cell or tissue that is associated with the autoimmune disease, and thereby treating or preventing the autoimmune disease. In another embodiment there is provided a method of treating or preventing an autoimmune disease in a subject having or suspected of being at risk for having an autoimmune disease, the method comprising administering to the subject a vaccine composition that comprises (a) an antigen; (b) a glucopyranosyl lipid adjuvant (GLA); and (c) a carrier that comprises at least one of an oil and ISCOMATRIX™, wherein the antigen is derived from, or is immunologically cross-reactive with, at least one epitope, biomolecule, cell or tissue that is associated with the autoimmune disease, and thereby treating or preventing the autoimmune disease. In another embodiment there is provided a method of treating or preventing an autoimmune disease in a subject having or suspected of being at risk for having an autoimmune disease, the method comprising administering to the subject a vaccine composition that comprises (a) an antigen; (b) a glucopyranosyl lipid adjuvant (GLA); and (c) one or more of: (i) at least one co-adjuvant, (ii) at least one TLR agonist, (iii) at least one imidazoquinoline immune response modifier, and (iv) at least one double stem loop immune modifier (dSLIM), wherein the antigen is derived from, or is immunologically cross-reactive with, at least one epitope, biomolecule, cell or tissue that is associated with the autoimmune disease, and thereby treating or preventing the autoimmune disease. In certain further embodiments (i) the co-adjuvant, when present, is selected from alum, a plant alkaloid and a detergent, wherein the plant alkaloid is tomatine and the detergent is selected from saponin, Polysorbate 80, Span 85 and Stearyl tyrosine, (ii) the TLR agonist, when present, is selected from the group consisting of lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen, and (iii) the imidazoquinoline immune response modifier, when present, is selected from the group consisting of resiquimod (R848), imiquimod and gardiquimod.

In another embodiment there is provided a method of treating or preventing an autoimmune disease in a subject having or suspected of being at risk for having an autoimmune disease, the method comprising administering to the subject a vaccine composition that comprises (a) an antigen; (b) a glucopyranosyl lipid adjuvant (GLA); and (c) at least one of a co-adjuvant and a pharmaceutically acceptable carrier, wherein: the co-adjuvant is selected from a cytokine, a block copolymer or biodegradable polymer, and a detergent, and the pharmaceutically acceptable carrier comprises a carrier that is selected from the group consisting of calcium phosphate, an oil-in-water emulsion, a water-in-oil emulsion, a liposome, and a microparticle, wherein the antigen is derived from, or is immunologically cross-reactive with, at least one epitope, biomolecule, cell or tissue that is associated with the autoimmune disease, and thereby treating or preventing the autoimmune disease. In a further embodiment the cytokine is selected from GM-CSF, IL-2, IL-7, IL-12, TNF-α and IFN-gamma, the block copolymer or biodegradable polymer is selected from Pluronic L121, CRL1005, PLGA, PLA, PLG, and polyI:C, and the detergent is selected from the group consisting of saponin, Polysorbate 80, Span 85 and Stearyl tyrosine.

In another embodiment there is provided a method of treating or preventing an autoimmune disease in a subject having or suspected of being at risk for having an autoimmune disease, the method comprising administering to the subject a vaccine composition that comprises (a) at least one recombinant expression construct which comprises a promoter operably linked to a nucleic acid sequence encoding an antigen; and (b) a glucopyranosyl lipid adjuvant (GLA), wherein the antigen is derived from, or is immunologically cross-reactive with, at least one epitope, biomolecule, cell or tissue that is associated with the autoimmune disease, and thereby treating or preventing the autoimmune disease. In a further embodiment the recombinant expression construct is present in a viral vector, which in certain further embodiments is present in a virus that is selected from an adenovirus, an adeno-associated virus, a herpesvirus, a lentivirus, a poxvirus, and a retrovirus.

In certain of the above described embodiments as relate to a method of treating or preventing an autoimmune disease, the autoimmune disease is selected from Type 1 diabetes, rheumatoid arthritis, multiple sclerosis, systemic lupus erythematosus, myasthenia gravis, Crohn's disease, Graves' disease, thrombocytopenic purpura and pemphigus. In certain other of the above described embodiments as relate to a method of treating or preventing an autoimmune disease, the epitope, biomolecule, cell or tissue that is associated with an autoimmune disease is selected from snRNP when the autoimmune disease is systemic lupus erythematosus, at least one of thyroglobulin, thyrotropin receptor and a thyroid epithelial cell when the autoimmune disease is Graves' disease, a platelet when the autoimmune disease is thrombocytopenic purpura, at least one of pemphigus antigen, desmoglein-3, desmoplakin, envoplakin and bullous pemphigoid antigen 1 when the autoimmune disease is pemphigus, myelin basic protein when the autoimmune disease is multiple sclerosis, a pancreatic islet beta cell when the autoimmune disease is type 1 diabetes, and an acetylcholine receptor when the autoimmune disease is myasthenia gravis.

According to other embodiments there is provided a method of treating or preventing cancer in a subject having or suspected of being at risk for having an cancer, the method comprising administering to the subject a vaccine composition that comprises (a) an antigen; and (b) a glucopyranosyl lipid adjuvant (GLA), wherein the antigen is derived from, or is immunologically cross-reactive with, at least one epitope, biomolecule, cell or tissue that is associated with the cancer, and thereby treating or preventing the cancer. According to other embodiments there is provided a method of treating or preventing cancer in a subject having or suspected of being at risk for having cancer, the method comprising administering to the subject a vaccine composition that comprises (a) an antigen; (b) a glucopyranosyl lipid adjuvant (GLA); and (c) a toll-like receptor (TLR) agonist, wherein the antigen is derived from, or is immunologically cross-reactive with, at least one epitope, biomolecule, cell or tissue that is associated with the cancer, and thereby treating or preventing the cancer. In certain further embodiments the TLR agonist is selected from lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen. According to other embodiments there is provided a method of treating or preventing cancer in a subject having or suspected of being at risk for having cancer, the method comprising administering to the subject a vaccine composition that comprises (a) an antigen; (b) a glucopyranosyl lipid adjuvant (GLA); and (c) at least one co-adjuvant that is selected from the group consisting of saponins and saponin mimetics, wherein the antigen is derived from, or is immunologically cross-reactive with, at least one epitope, biomolecule, cell or tissue that is associated with the cancer, and thereby treating or preventing the cancer.

According to other embodiments there is provided a method of treating or preventing cancer in a subject having or suspected of being at risk for having cancer, the method comprising administering to the subject a vaccine composition that comprises (a) an antigen; (b) a glucopyranosyl lipid adjuvant (GLA); and (c) a carrier that comprises at least one of an oil and ISCOMATRIX™, wherein the antigen is derived from, or is immunologically cross-reactive with, at least one epitope, biomolecule, cell or tissue that is associated with the cancer, and thereby treating or preventing the cancer. According to other embodiments there is provided a method of treating or preventing cancer in a subject having or suspected of being at risk for having cancer, the method comprising administering to the subject a vaccine composition that comprises (a) an antigen; (b) a glucopyranosyl lipid adjuvant (GLA); and (c) one or more of: (i) at least one co-adjuvant, (ii) at least one TLR agonist, (iii) at least one imidazoquinoline immune response modifier, and (iv) at least one double stem loop immune modifier (dSLIM), wherein the antigen is derived from, or is immunologically cross-reactive with, at least one epitope, biomolecule, cell or tissue that is associated with the cancer, and thereby treating or preventing the cancer. In certain further embodiments (i) the co-adjuvant, when present, is selected from the group consisting of alum, a plant alkaloid and a detergent, wherein the plant alkaloid is tomatine and the detergent is selected from saponin, Polysorbate 80, Span 85 and Stearyl tyrosine, (ii) the TLR agonist, when present, is selected from the group consisting of lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen, and (iii) the imidazoquinoline immune response modifier, when present, is selected from the group consisting of resiquimod (R848), imiquimod and gardiquimod. According to other embodiments there is provided a method of treating or preventing cancer in a subject having or suspected of being at risk for having cancer, the method comprising administering to the subject a vaccine composition that comprises (a) an antigen; (b) a glucopyranosyl lipid adjuvant (GLA); and (c) at least one of a co-adjuvant and a pharmaceutically acceptable carrier, wherein the co-adjuvant is selected from the group consisting of a cytokine, a block copolymer or biodegradable polymer, and a detergent, and the pharmaceutically acceptable carrier comprises a carrier that is selected from the group consisting of calcium phosphate, an oil-in-water emulsion, a water-in-oil emulsion, a liposome, and a microparticle, wherein the antigen is derived from, or is immunologically cross-reactive with, at least one epitope, biomolecule, cell or tissue that is associated with the cancer, and thereby treating or preventing the cancer. In a further embodiment the cytokine is selected from GM-CSF, IL-2, IL-7, IL-12, TNF-α and IFN-gamma, the block copolymer or biodegradable polymer is selected from Pluronic L121, CRL1005, PLGA, PLA, PLG, and polyI:C, and the detergent is selected from saponin, Polysorbate 80, Span 85 and Stearyl tyrosine. According to other embodiments there is provided a method of treating or preventing cancer in a subject having or suspected of being at risk for having cancer, the method comprising administering to the subject a vaccine composition that comprises (a) at least one recombinant expression construct which comprises a promoter operably linked to a nucleic acid sequence encoding an antigen; and (b) a glucopyranosyl lipid adjuvant (GLA), wherein the antigen is derived from, or is immunologically cross-reactive with, at least one epitope, biomolecule, cell or tissue that is associated with the cancer, and thereby treating or preventing the cancer. In a further embodiment the recombinant expression construct is present in a viral vector, which in certain further embodiments is present in a virus that is selected from an adenovirus, an adeno-associated virus, a herpesvirus, a lentivirus, a poxvirus, and a retrovirus. In certain further embodiments of the above described methods of treating or preventing cancer the antigen is derived from at least one cancer cell, which in certain further embodiments originates in a primary solid tumor, and in certain other further embodiments originates in a cancer that is a metastatic or secondary solid tumor, and in certain other further embodiments originates in a cancer that is a circulating tumor or an ascites tumor. In certain embodiments the cancer cell originates in a cancer that is selected from cervical cancer, ovarian cancer, breast cancer, prostate cancer, fibrosarcoma, myxosarcoma, liposarcoma, chondrosarcoma, osteogenic sarcoma, chordoma, angiosarcoma, endotheliosarcoma, lymphangiosarcoma, pseudomyxoma petitonei, lymphangioendotheliosarcoma, synovioma, mesothelioma, Ewing's tumor, leiomyosarcoma, rhabdomyosarcoma, colon carcinoma, pancreatic cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma and Wilms' tumor. In certain other embodiments the cancer cell originates in a cancer that is selected from testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, Waldenstrom's macroglobulinemia and heavy chain disease.

According to certain further embodiments of any one of the above-described methods of treating or preventing infectious disease or autoimmune disease or cancer, the step of administering is performed once, while in certain other further embodiments of such methods the step of administering is performed at least two times, and in certain other further embodiments the step of administering is performed at least three times, and in certain other further embodiments the step of administering is performed four or more times. According to certain further embodiments of any one of the above-described methods of treating or preventing infectious disease or autoimmune disease or cancer, prior to the step of administering, the subject is primed with a priming agent that is selected from a bacterial extract, a live virus vaccine, at least one recombinant expression construct which comprises a promoter operably linked to a nucleic acid sequence encoding the antigen, and a viral vector that comprises a promoter operably linked to a nucleic acid sequence encoding the antigen. In a further embodiment the bacterial extract is derived from Bacillus Calmet-Guerin (BCG).

In another embodiment there is provided a method of eliciting or enhancing a desired antigen-specific immune response in a subject, comprising administering to the subject a vaccine composition that comprises (a) an antigen, and (b) a glucopyranosyl lipid adjuvant (GLA). In another embodiment there is provided a method of eliciting or enhancing a desired antigen-specific immune response in a subject, comprising administering to the subject a vaccine composition that comprises (a) an antigen, (b) a glucopyranosyl lipid adjuvant (GLA), and (c) a toll-like receptor (TLR) agonist. In certain further embodiments the TLR agonist is selected from lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen. In another embodiment there is provided a method of eliciting or enhancing a desired antigen-specific immune response in a subject, comprising administering to the subject a vaccine composition that comprises (a) an antigen, (b) a glucopyranosyl lipid adjuvant (GLA), and (c) at least one co-adjuvant that is selected from the group consisting of saponins and saponin mimetics. In another embodiment there is provided a method of eliciting or enhancing a desired antigen-specific immune response in a subject, comprising administering to the subject a vaccine composition that comprises (a) an antigen, (b) a glucopyranosyl lipid adjuvant (GLA), and (c) a carrier that comprises at least one of an oil and ISCOMATRIX™. In another embodiment there is provided a method of eliciting or enhancing a desired antigen-specific immune response in a subject, comprising administering to the subject a vaccine composition that comprises (a) an antigen; (b) a glucopyranosyl lipid adjuvant (GLA); and (c) one or more of: (i) at least one co-adjuvant, (ii) at least one TLR agonist, (iii) at least one imidazoquinoline immune response modifier, and (iv) at least one double stem loop immune modifier (dSLIM). In certain further embodiments, the co-adjuvant, when present, is selected from alum, a plant alkaloid and a detergent, wherein the plant alkaloid is selected from tomatine and the detergent is selected from saponin, Polysorbate 80, Span 85 and Stearyl tyrosine, (ii) the TLR agonist, when present, is selected from the group consisting of lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen, and (iii) the imidazoquinoline immune response modifier, when present, is selected from the group consisting of resiquimod (R848), imiquimod and gardiquimod.

In another embodiment there is provided a method of eliciting or enhancing a desired antigen-specific immune response in a subject, comprising administering to the subject a vaccine composition that comprises (a) an antigen; (b) a glucopyranosyl lipid adjuvant (GLA); and (c) at least one of a co-adjuvant and a pharmaceutically acceptable carrier, wherein: the co-adjuvant is selected from a cytokine, a block copolymer, a biodegradable polymer, and a detergent, and the pharmaceutically acceptable carrier comprises a carrier that is selected from calcium phosphate, an oil-in-water emulsion, a water-in-oil emulsion, a liposome, and a microparticle. In certain further embodiments the cytokine is selected from GM-CSF, IL-2, IL-7, IL-12, TNF-α and IFN-gamma, the block copolymer or biodegradable polymer is selected from Pluronic L121, CRL1005, PLGA, PLA, PLG, and polyI:C, and the detergent is selected from the group consisting of saponin, Polysorbate 80, Span 85 and Stearyl tyrosine.

In another embodiment there is provided a method of eliciting or enhancing a desired antigen-specific immune response in a subject, comprising administering to the subject a vaccine composition that comprises (a) at least one recombinant expression construct which comprises a promoter operably linked to a nucleic acid sequence encoding an antigen, and (b) a glucopyranosyl lipid adjuvant (GLA). In certain further embodiments the recombinant expression construct is present in a viral vector, which in certain further embodiments is present in a virus that is selected from an adenovirus, an adeno-associated virus, a herpesvirus, a lentivirus, a poxvirus, and a retrovirus.

In certain further embodiments of the above described methods of eliciting or enhancing a desired antigen-specific response in a subject, the GLA is not 3'-de-O-acylated. In certain other further embodiments of the above described methods of eliciting or enhancing a desired antigen-specific response in a subject, the GLA comprises: (i) a diglucosamine backbone having a reducing terminus glucosamine linked to a non-reducing terminus glucosamine through an ether linkage between hexosamine position 1 of the non-reducing terminus glucosamine and hexosamine position 6 of the reducing terminus glucosamine; (ii) an O-phosphoryl group attached to hexosamine position 4 of the non-reducing terminus glucosamine; and (iii) up to six fatty acyl chains; wherein one of the fatty acyl chains is attached to 3-hydroxy of the reducing terminus glucosamine through an ester linkage, wherein one of the fatty acyl chains is attached to a 2-amino of the non-reducing terminus glucosamine through an amide linkage and comprises a tetradecanoyl chain linked to an alkanoyl chain of greater than 12 carbon atoms through an ester linkage, and wherein one of the fatty acyl chains is attached to 3-hydroxy of the non-reducing terminus glucosamine through an ester linkage and comprises a tetradecanoyl chain linked to an alkanoyl chain of greater than 12 carbon atoms through an ester linkage. In certain related further embodiments the TLR agonist, when present, is capable of delivering a biological signal by interacting with at least one TLR that is selected from TLR-2, TLR-3, TLR-4, TLR-5, TLR-6, TLR-7, TLR-8 and TLR-9. In certain further embodiments the TLR agonist is selected from lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen.

In certain further embodiments of the above described methods of eliciting or enhancing a desired antigen-specific response in a subject, the GLA has the formula:

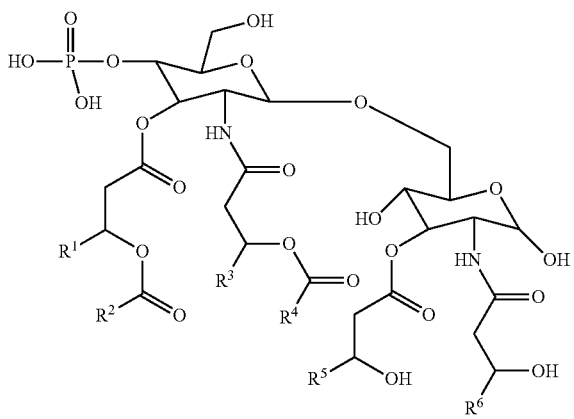

where:
$R^1$, $R^3$, $R^5$ and $R^6$ are $C_{11}$-$C_{20}$ alkyl; and
$R^2$ and $R^4$ are $C_{12}$-$C_{20}$ alkyl.

In certain further embodiments of the above described methods of eliciting or enhancing a desired antigen-specific response in a subject, the vaccine composition is capable of eliciting an immune response in a host. In certain further embodiments the immune response is specific for the antigen. In certain further embodiments of the above described methods of eliciting or enhancing a desired antigen-specific response in a subject, the antigen is capable of eliciting in a host an immune response that is selected from a humoral response and a cell-mediated response. In certain further embodiments of the above described methods of eliciting or enhancing a desired antigen-specific response in a subject, the vaccine composition is capable of eliciting in a host at least one immune response that is selected from the group consisting of: a $T_H1$-type T lymphocyte response, a $T_H2$-type T lymphocyte response, a cytotoxic T lymphocyte (CTL) response, an antibody response, a cytokine response, a lymphokine response, a chemokine response, and an inflammatory response. In certain further embodiments of the above described methods of eliciting or enhancing a desired antigen-specific response in a subject, the vaccine composition is capable of eliciting in a host at least one immune response that is selected from the group consisting of: (a) production of one or a plurality of cytokines wherein the cytokine is selected from the group consisting of interferon-gamma (IFN-γ) and tumor necrosis factor-alpha (TNF-α), (b) production of one or a plurality of interleukins wherein the interleukin is selected from IL-1, IL-2, IL-3, IL-4, IL-6, IL-8, IL-10, IL-12, IL-13, IL-16, IL-18 and IL-23, (c) production one or a plurality of chemokines wherein the chemokine is selected from MIP-1α, MIP-1β, RANTES, CCL4 and CCL5, and (d) a lymphocyte response that is selected from a memory T cell response, a memory B cell response, an effector T cell response, a cytotoxic T cell response and an effector B cell response.

According to certain other embodiments, there is provided a method of preparing a vaccine composition, comprising admixing (a) an antigen and (b) a glucopyranosyl lipid adjuvant (GLA). According to certain other embodiments, there is provided a method of preparing a vaccine composition, comprising admixing (a) an antigen, (b) a glucopyranosyl lipid adjuvant (GLA) and (c) a toll-like receptor (TLR) agonist. In certain further embodiments the TLR agonist is selected from lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen. According to certain other embodiments, there is provided a method of preparing a vaccine composition, comprising admixing (a) an antigen, (b) a glucopyranosyl lipid adjuvant (GLA), and (c) at least one co-adjuvant that is selected from the group consisting of saponins and saponin mimetics. According to certain other embodiments, there is provided a method of preparing a vaccine composition, comprising admixing (a) an antigen, (b) a glucopyranosyl lipid adjuvant (GLA), and (c) a carrier that comprises at least one of an oil and ISCOMATRIX™. According to certain other embodiments, there is provided a method of preparing a vaccine composition, comprising admixing (a) an antigen; (b) a glucopyranosyl lipid adjuvant (GLA); and (c) one or more of: (i) at least one co-adjuvant, (ii) at least one TLR agonist, (iii) at least one imidazoquinoline immune response modifier, and (iv) at least one double stem loop immune modifier (dSLIM). In certain further embodiments, (i) the co-adjuvant, when present, is selected from the group consisting of alum, a plant alkaloid and a detergent, wherein the plant alkaloid is selected from tomatine and the detergent is selected from saponin, Polysorbate 80, Span 85 and Stearyl tyrosine, (ii) the TLR agonist, when present, is selected from the group consisting of lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen, and (iii) the imidazoquinoline immune response modifier, when present, is selected from the group consisting of resiquimod (R848), imiquimod and gardiquimod. According to certain other embodiments, there is provided a method of preparing a vaccine composition, comprising admixing (a) an antigen; (b) a glucopyranosyl lipid adjuvant (GLA); and (c) at least one of a co-adjuvant and a pharmaceutically acceptable carrier, wherein: the co-adjuvant is selected from the group consisting of a cytokine, a block copolymer or biodegradable polymer, and a detergent, and the pharmaceutically acceptable carrier comprises a carrier that is selected from the group consisting of calcium phosphate, an oil-in-water emulsion, a water-in-oil emulsion, a liposome, and a microparticle. In certain further embodiments the cytokine is selected from GM-CSF, IL-2, IL-7, IL-12, TNF-α and IFN-gamma, the block copolymer or biodegradable polymer is selected from Pluronic L121, CRL1005, PLGA, PLA, PLG, and polyI:C, and the detergent is selected from saponin, Polysorbate 80, Span 85 and Stearyl tyrosine.

According to certain other embodiments, there is provided a method of preparing a vaccine composition, comprising admixing (a) at least one recombinant expression construct which comprises a promoter operably linked to a nucleic acid sequence encoding an antigen, and (b) a glucopyranosyl lipid adjuvant (GLA). In certain further embodiments the recombinant expression construct is present in a viral vector, which in certain further embodiments is present in a virus that is selected from an adenovirus, an adeno-associated virus, a herpesvirus, a lentivirus, a poxvirus, and a retrovirus. In certain embodiments the GLA is not 3'-de-O-acylated. In certain embodiments the GLA comprises: (i) a diglucosamine backbone having a reducing terminus glucosamine linked to a non-reducing terminus glucosamine through an ether linkage between hexosamine position 1 of the non-reducing terminus glucosamine and hexosamine position 6 of the reducing terminus glucosamine; (ii) an O-phosphoryl group attached to hexosamine position 4 of the non-reducing terminus glucosamine; and (iii) up to six fatty acyl chains; wherein one of the fatty acyl chains is attached to 3-hydroxy of the reducing terminus glucosamine through an ester linkage, wherein one of the fatty acyl chains is attached to a 2-amino of the non-reducing terminus glucosamine through an amide linkage and comprises a tetradecanoyl chain linked to an alkanoyl chain of greater than 12 carbon atoms through an ester linkage, and wherein one of the fatty acyl chains is attached to 3-hydroxy of the non-reducing terminus glucosamine through an ester linkage and comprises a tetradecanoyl chain linked to an alkanoyl chain of greater than 12 carbon atoms through an ester linkage. In certain embodiments the TLR agonist is capable of delivering a biological signal by interacting with at least one TLR that is selected from TLR-2, TLR-3, TLR-4, TLR-5, TLR-6, TLR-7, TLR-8 and TLR-9. In certain further embodiments the TLR agonist is selected from lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen.

According to certain embodiments of the above-described methods of preparing a vaccine composition, the GLA has the formula:

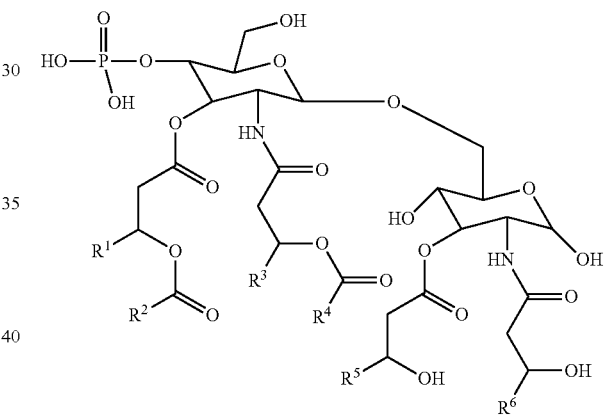

where:
$R^1$, $R^3$, $R^5$ and $R^6$ are $C_{11}$-$C_{20}$ alkyl; and
$R^2$ and $R^4$ are $C_{12}$-$C_{20}$ alkyl.

In certain further embodiments the step of admixing comprises emulsifying, and in certain other further embodiments the step of admixing comprises forming particles, which in certain further embodiments comprise microparticles. In certain other further embodiments the step of admixing comprises forming a precipitate which comprises all or a portion of the antigen and all or a portion of the GLA.

In certain other embodiments there is provided an immunological adjuvant pharmaceutical composition comprising: a glycopyranosyl lipid adjuvant (GLA); and a pharmaceutically acceptable carrier or excipient. In certain other embodiments there is provided an immunological adjuvant composition comprising a glycopyranosyl lipid adjuvant (GLA); and a toll-like receptor (TLR) agonist. In certain further embodiments the TLR agonist is selected from lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen. In certain other embodiments there is provided an immunological adjuvant composition comprising: a glycopyranosyl lipid adjuvant (GLA); and at least one co-adjuvant that is selected from saponins and saponin mimetics. In certain other embodiments there is provided an immunological adjuvant pharmaceutical composition comprising: a glycopyranosyl lipid adjuvant (GLA); and a pharmaceutically acceptable carrier that comprises at least one of an oil and ISCOMATRIX™. In certain other embodiments there is provided an immunological adjuvant composition comprising: (a) a glycopyranosyl lipid adjuvant (GLA); and (b) one or more of: (i) at least one co-adjuvant, (ii) at least one TLR agonist, (iii) at least one imidazoquinoline immune response modifier, and (iv) at least one double stem loop immune modifier (dSLIM).

In certain further embodiments, (i) the co-adjuvant, when present, is selected from the group consisting of alum, a plant alkaloid and a detergent, wherein the plant alkaloid is tomatine and the detergent is selected from saponin, Polysorbate 80, Span 85 and Stearyl tyrosine, (ii) the TLR agonist, when present, is selected from the group consisting of lipopolysaccharide, peptidoglycan, polyI:C, CpG, 3M003, flagellin, Leishmania homolog of eukaryotic ribosomal elongation and initiation factor 4a (LeIF) and at least one hepatitis C antigen, and (iii) the imidazoquinoline immune response modifier, when present, is selected from the group consisting of resiquimod (R848), imiquimod and gardiquimod.

In certain other embodiments there is provided an immunological adjuvant composition comprising: a glycopyranosyl lipid adjuvant (GLA); and at least one of a co-adjuvant and a pharmaceutically acceptable carrier, wherein: the co-adjuvant is selected from the group consisting of a cytokine, a block copolymer or biodegradable polymer, and a detergent, and the pharmaceutically acceptable carrier comprises a carrier that is selected from calcium phosphate, an oil-in-water emulsion, a water-in-oil emulsion, a liposome, and a microparticle. In certain further embodiments the cytokine is selected from GM-CSF, IL-2, IL-7, IL-12, TNF and IFN-gamma, the block copolymer or biodegradable polymer is selected from Pluronic L121, CRL1005, PLGA, PLA, PLG, and polyI:C, and the detergent is selected from the group consisting of saponin, Polysorbate 80, Span 85 and Stearyl tyrosine.

In certain other embodiments there is provided a method of altering immunological responsiveness in a host, comprising: administering to the host an immunological adjuvant pharmaceutical composition that comprises a glycopyranosyl lipid adjuvant (GLA), and a pharmaceutically acceptable carrier or excipient, and thereby altering host immunological responsiveness. In certain other embodiments there is provided a method of altering immunological responsiveness in a host, comprising: administering to the host an immunological adjuvant composition that comprises a glycopyranosyl lipid adjuvant (GLA), and (b) a toll-like receptor (TLR) agonist, and thereby altering host immunological responsiveness. In certain further embodiments the TLR agonist is selected from lipopolysaccharide, peptidoglycan, polyI:C, CpG, 3M003, flagellin, Leishmania homolog of eukaryotic ribosomal elongation and initiation factor 4a (LeIF) and at least one hepatitis C antigen. In certain other embodiments there is provided a method of altering immunological responsiveness in a host, comprising: administering to the host an immunological adjuvant composition that comprises a glycopyranosyl lipid adjuvant (GLA), and at least one co-adjuvant that is selected from the group consisting of saponins and saponin mimetics, and thereby altering host immunological responsiveness. In certain other embodiments there is provided a method of altering immunological responsiveness in a host, comprising: administering to the host an immunological adjuvant composition that comprises a glycopyranosyl lipid adjuvant (GLA), and a pharmaceutically acceptable carrier that comprises at least one of an oil and ISCOMATRIX™, and thereby altering host immunological responsiveness. In certain other embodiments there is provided a method of altering immunological responsiveness in a host, comprising: administering to the host an immunological adjuvant composition that comprises a glycopyranosyl lipid adjuvant (GLA), and one or more of: (i) at least one co-adjuvant, (ii) at least one TLR agonist, (iii) at least one imidazoquinoline immune response modifier, and (iv) at least one double stem loop immune modifier (dSLIM), and thereby altering host immunological responsiveness.

In certain further embodiments, the co-adjuvant, when present, is selected from alum, a plant alkaloid and a detergent, wherein the plant alkaloid is tomatine and the detergent is selected from saponin, Polysorbate 80, Span 85 and Stearyl tyrosine, the TLR agonist, when present, is selected from lipopolysaccharide, peptidoglycan, polyI:C, CpG, 3M003, flagellin, Leishmania homolog of eukaryotic ribosomal elongation and initiation factor 4a (LeIF) and at least one hepatitis C antigen, and the imidazoquinoline immune response modifier, when present, is selected from the group consisting of resiquimod (R848), imiquimod and gardiquimod.

In certain other embodiments there is provided a method of altering immunological responsiveness in a host, comprising: administering to the host an immunological adjuvant composition that comprises a glycopyranosyl lipid adjuvant (GLA); and at least one of a co-adjuvant and a pharmaceutically acceptable carrier, wherein: the co-adjuvant is selected from the group consisting of a cytokine, a block copolymer or biodegradable polymer, and a detergent, and the pharmaceutically acceptable carrier comprises a carrier that is selected from the group consisting of calcium phosphate, an oil-in-water emulsion, a water-in-oil emulsion, a liposome, and a microparticle, and thereby altering host immunological responsiveness. In certain further embodiments the cytokine is selected from GM-CSF, IL-2, IL-7, IL-12, TNF-α and IFN-gamma, the block copolymer or biodegradable polymer is selected from Pluronic L121, CRL1005, PLGA, PLA, PLG, and polyI:C, and the detergent is selected from the group consisting of saponin, Polysorbate 80, Span 85 and Stearyl tyrosine.

In certain further embodiments of the above described methods of altering immunological responsiveness in a host, the step of administering is performed one, two, three, four or more times. In certain other further embodiments of the above described methods of altering immunological responsiveness in a host, altering immunological responsiveness in the host comprises inducing or enhancing an immune response. In certain other further embodiments of the above described methods of altering immunological responsiveness in a host, altering immunological responsiveness in the host comprises down-regulating an immune response. In certain further embodiments of the above described methods of altering immunological responsiveness in a host, the method further comprises administering simultaneously or sequentially and in either order an antigen that is derived from, or is immunologically cross-reactive with, at least one infectious pathogen that is associated with an infectious disease against which induced or enhanced immunological responsiveness is desired. In certain further such embodiments the step of administering the antigen is performed one, two, three, four or more times. In certain other further embodiments of the above described methods of altering immunological responsiveness in a host, the method comprises administering simultaneously or sequentially and in either order an antigen that is derived from, or is immunologically cross-reactive with, at least one epitope, biomolecule, cell or tissue that is associated with an autoimmune disease and against which down-regulated immunological responsiveness is desired. In certain further such embodiments the step of administering the antigen is performed one, two, three, four or more times. In certain other further embodiments of the above described methods of altering immunological responsiveness in a host, the method comprises administering simultaneously or sequentially and in either order an antigen that is derived from, or is immunologically cross-reactive with, at least one epitope, biomolecule, cell or tissue that is associated with a cancer against which induced or enhanced immunological responsiveness is desired. In certain further such embodiments the step of administering the antigen is performed one, two, three, four or more times.

In another embodiment there is provided a kit, comprising: an immunological adjuvant composition as described above in a first container; and an antigen in a second container, wherein the immunological adjuvant composition is not in contact with the antigen. In another embodiment there is provided a kit, comprising: an immunological adjuvant composition as described above in a first container; and at least one recombinant expression construct which comprises a promoter operably linked to a nucleic acid sequence encoding an antigen, in a second container, wherein the immunological adjuvant composition is not in contact with the recombinant expression construct. In certain further embodiments of the just-described kit, the antigen is derived from at least one infectious pathogen that is selected from a bacteria, a virus, a yeast and a protozoan. In certain other further embodiments of the just-described kit, the antigen is derived from at least one cancer cell. In certain other further embodiments of the just-described kit, the antigen is derived from, or is immunologically cross-reactive with, at least one epitope, biomolecule, cell or tissue that is associated with an autoimmune disease.

These and other aspects of the present invention will become evident upon reference to the following detailed description and attached drawings. In addition, various references are set forth herein which describe in more detail certain aspects of this invention, and are therefore incorporated by reference in their entireties.

BRIEF DESCRIPTION OF THE SEVERAL VIEWS OF THE DRAWING(S)

FIG. 1 shows HPLC data demonstrating the number and amounts of contaminating materials in MPL-AF and GLA-AF. These chromatograms were collected using an Agilent 1100 system and an ESA Corona CAD detector. The method was run using a methanol to chloroform gradient on a Waters Atlantis C18 column. The injections included 2.5 µg of GLA and MPL respectively and 0.27 µg of synthetic phosphocholine (POPC) which is used as a solubilizing agent.

FIGS. 2A-2H show ELISA data demonstrating levels of cytokines and chemokines expressed by human macrophages of the Mono Mac 6 cell line (FIGS. 2A-2E), and PBMC-derived DC (FIGS. 2F-H) in response to GLA stimulation. Cells were cultured at 1×105 cells/well with an aqueous formulation of GSK Biologicals MPL® (MPL-AF), GLA (GLA-AF), or AF vehicle alone for 24 hrs. MIP-1b, IP-10, IL-6, IL-23 and IL-1b levels in supernatants were measured by sandwich ELISA.

Figure 3A:
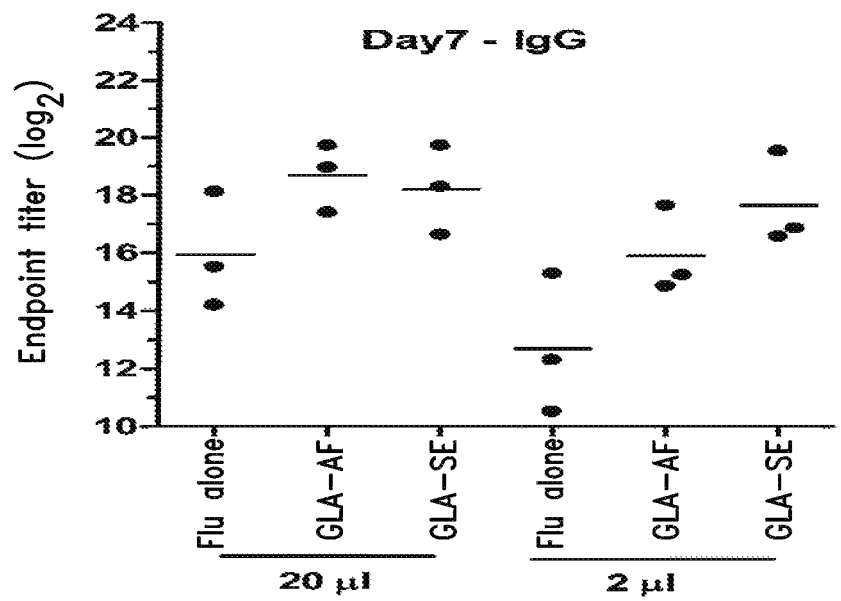
Figure 3B:
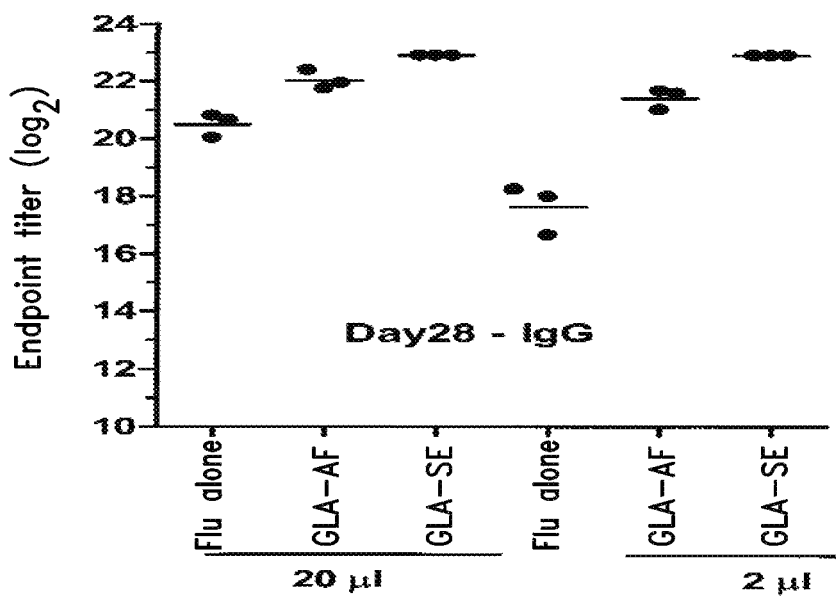
Figure 3C:
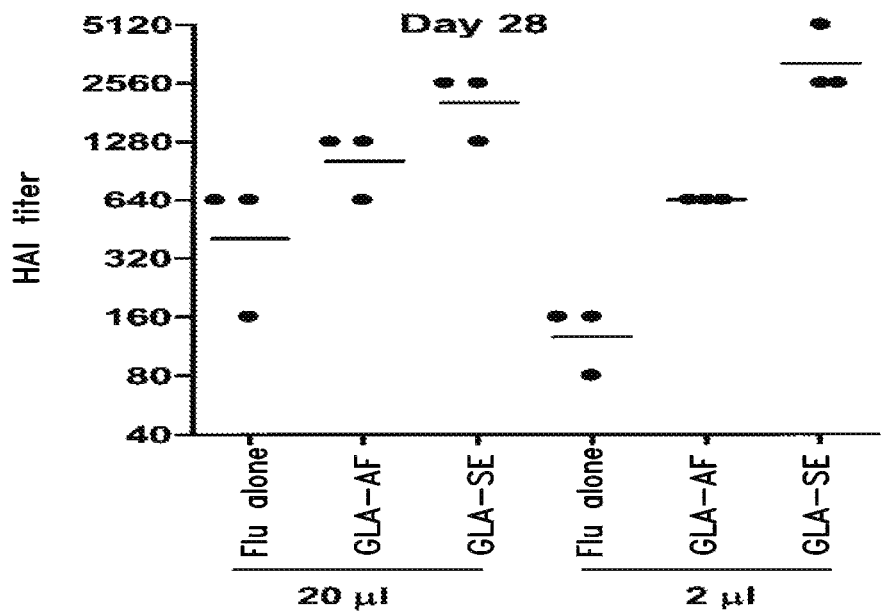

FIGS. 3A-3C show ELISA data demonstrating levels of anti-Fluzone antibody production induced in mice one week after each immunization (i.e., at day 7, FIG. 3A; and at day 28, FIG. 3B) using two different doses of Fluzone vaccine formulated with GLA-AF, or GLA-SE, compared to Fluzone alone. FIG. 3A and FIG. 3B show ELISA Ab titers of mice immunized twice at 3 weeks interval with 20 ml (1.8 µg) or 2 ml (0.18 mg) of Fluzone (Flu) vaccine in a formulation containing GLA-AF, GLA-SE or no adjuvant, one week after the first (FIG. 3A) or second (FIG. 3B) injection. FIG. 3C shows titers of neutralizing antibody (HAI) in the sera of mice after the second immunization.

Figure 4:
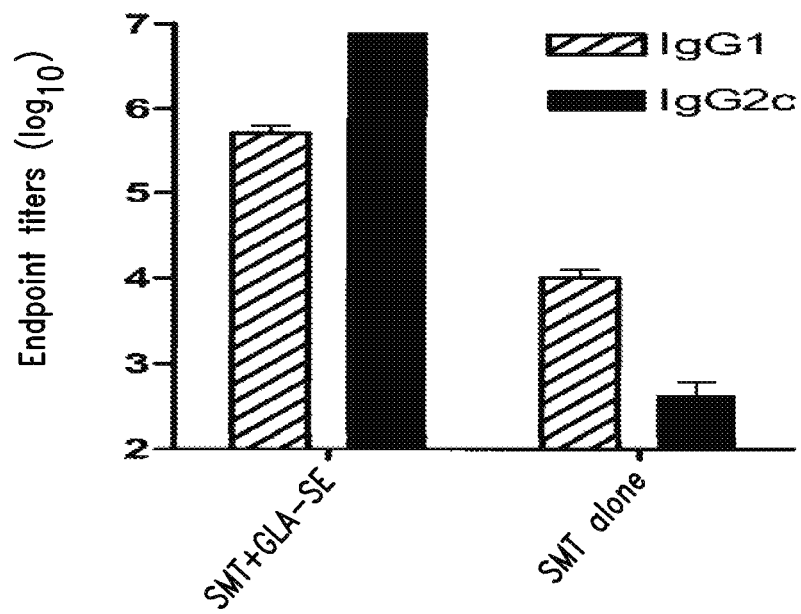

FIG. 4 shows ELISA data demonstrating levels of anti-SMT antibody production induced in mice one week after the third immunization using SMT antigen alone, or formulated with GLA-SE. C57BL/6 mice were immunized three times at three-week intervals with SMT antigen (10 µg per animal for each immunization) formulated in a stable emulsion containing GLA (GLA-SE; 20 µg per animal for each immunization), or injected with SMT protein alone. Sera were collected by bleeding one week after each immunization, and serum levels of IgG1, and IgG2c antibodies specific for SMT were examined by ELISA. Means and SEM of reciprocal endpoint titers are shown.

Figure 5:
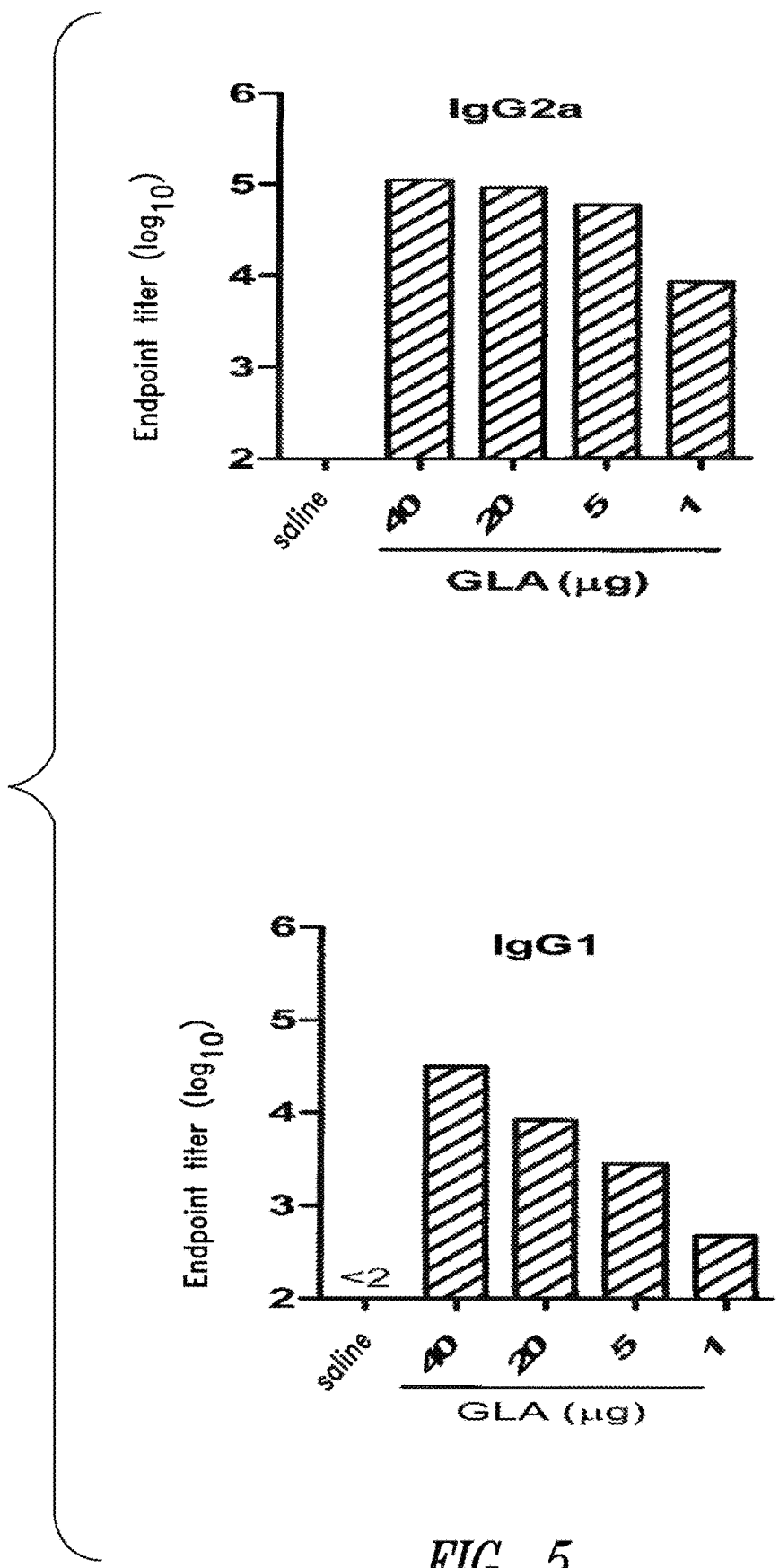

FIG. 5 shows ELISA data demonstrating levels of anti-Leish-110f antibody production induced in mice one week after the first immunization using Leish-110f antigen formulated with different amounts of GLA (40, 20, 5, or 1 µg), compared to saline controls. Balb/c mice were immunized three times at two-week intervals with the Leish-110f antigen (10 µg per animal for each immunization) formulated in a stable emulsion containing 40, 20, 5, or 1 mg of GLA (GLA-SE), or injected with saline. Sera were collected by bleeding one week after each immunization, and serum levels of IgG1 and IgG2a antibodies specific for Leish-110f were examined by ELISA. Means and SEM of reciprocal endpoint titers are shown for the sera collected 7 days after the 1st immunization.

Figure 6A:
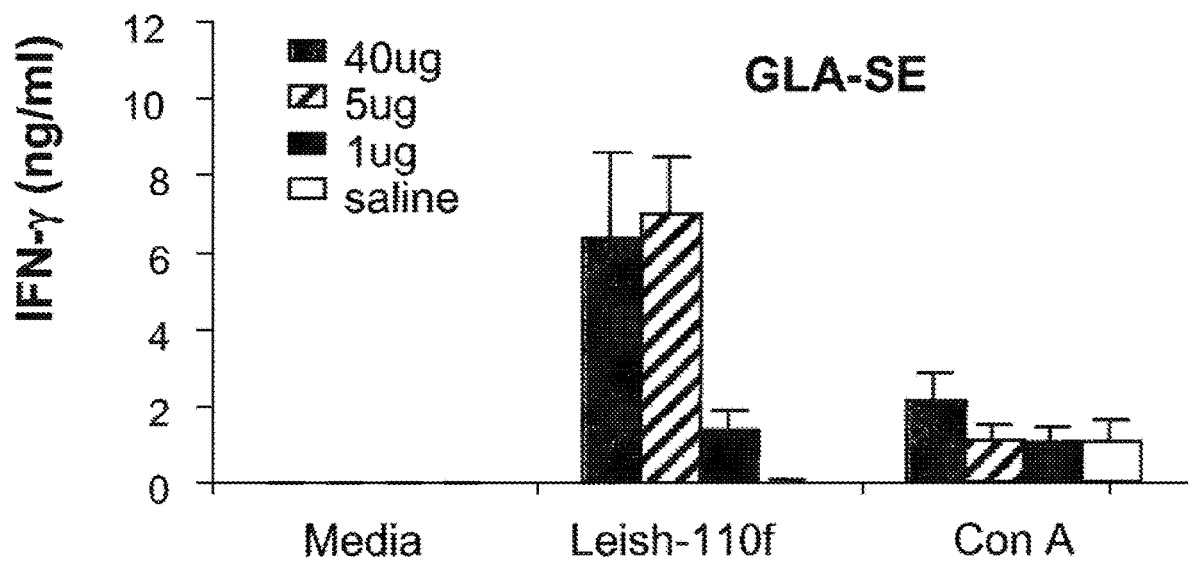
Figure 6B:
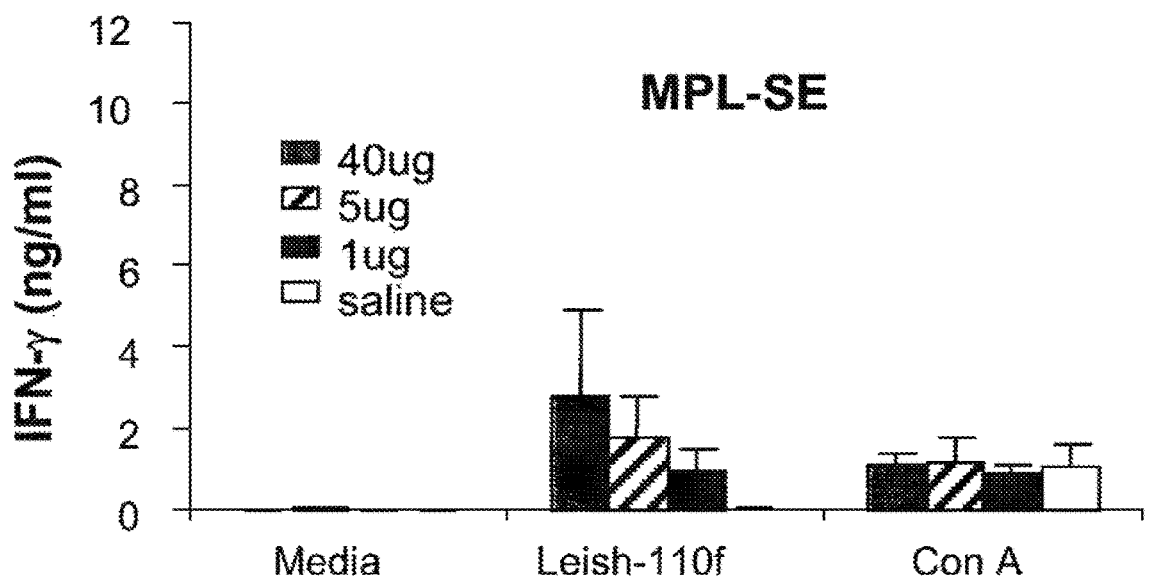

FIGS. 6A and 6B show ELISA data demonstrating levels of anti-Leish-110f IFN-γ cytokine production induced in mice one week after the third immunization using Leish-110f antigen formulated with different amounts of GLA, compared to saline controls. Splenocytes, from Balb/c mice immunized three times at two-week intervals with Leish-110f antigen (10 µg) formulated in a stable emulsion containing 40, 5, or 1 µg of MPL (MPL-SE) (FIG. 6B) or GLA (GLA-SE) (FIG. 6A), or from mice injected with a saline solution, were cultured for 3 days in vitro in medium alone, or in medium containing 10 mg/ml of Leish-110f, or 3 mg/ml of Concanavalin A (ConA). IFN-g levels in supernatants were measured by ELISA. Means and SEM are shown.

Figure 7:
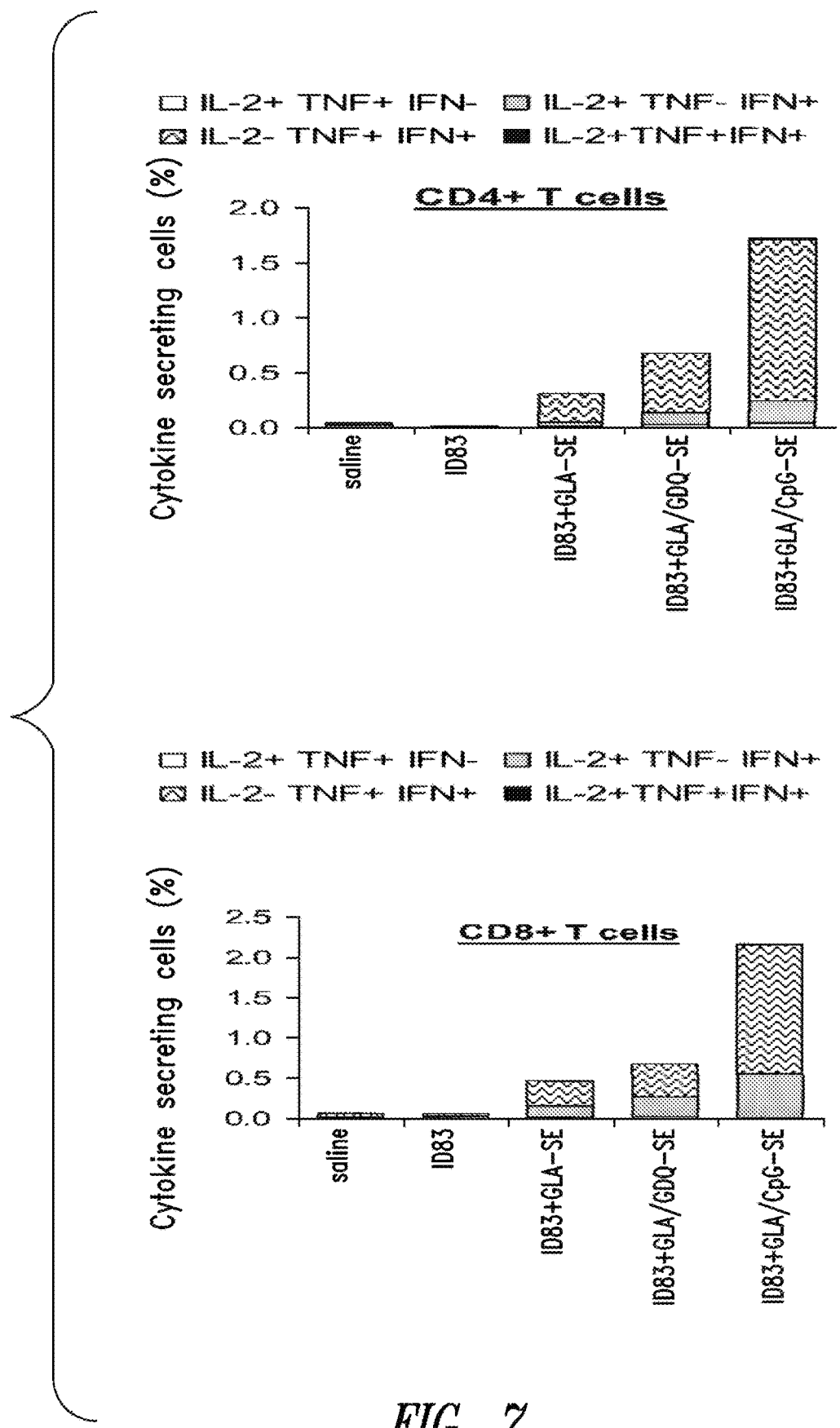

FIG. 7 shows ICS data demonstrating the frequencies of ID83-specific IFN-γ, IL-2, and TNF cytokine producing CD4+ and CD8+ T cells induced in mice one week after the third immunization using ID83 alone or adjuvanted with formulations containing GLA (GLA-SE), GLA+CpG (GLA/CpG-SE), or GLA+GDQ (GLA/GDQ-SE). Splenocytes from C57BL/6 mice, immunized three times at three-week intervals with *M. tuberculosis* ID83 fusion protein (8 µg) formulated with GLA-SE, GLA/CpG-SE, GLA/Gardiquimod (GDQ)-SE, or injected with saline, were cultured in vitro for 12 hrs in medium containing 10 mg/ml of ID83. Cell levels of IL-2, TNF, and IFN-g in CD3+CD4+ or CD3+CD8+ gated T cells were detected by intracellular staining and measured by flow cytometry on a BD LSRII FACS.

Figure 8A:
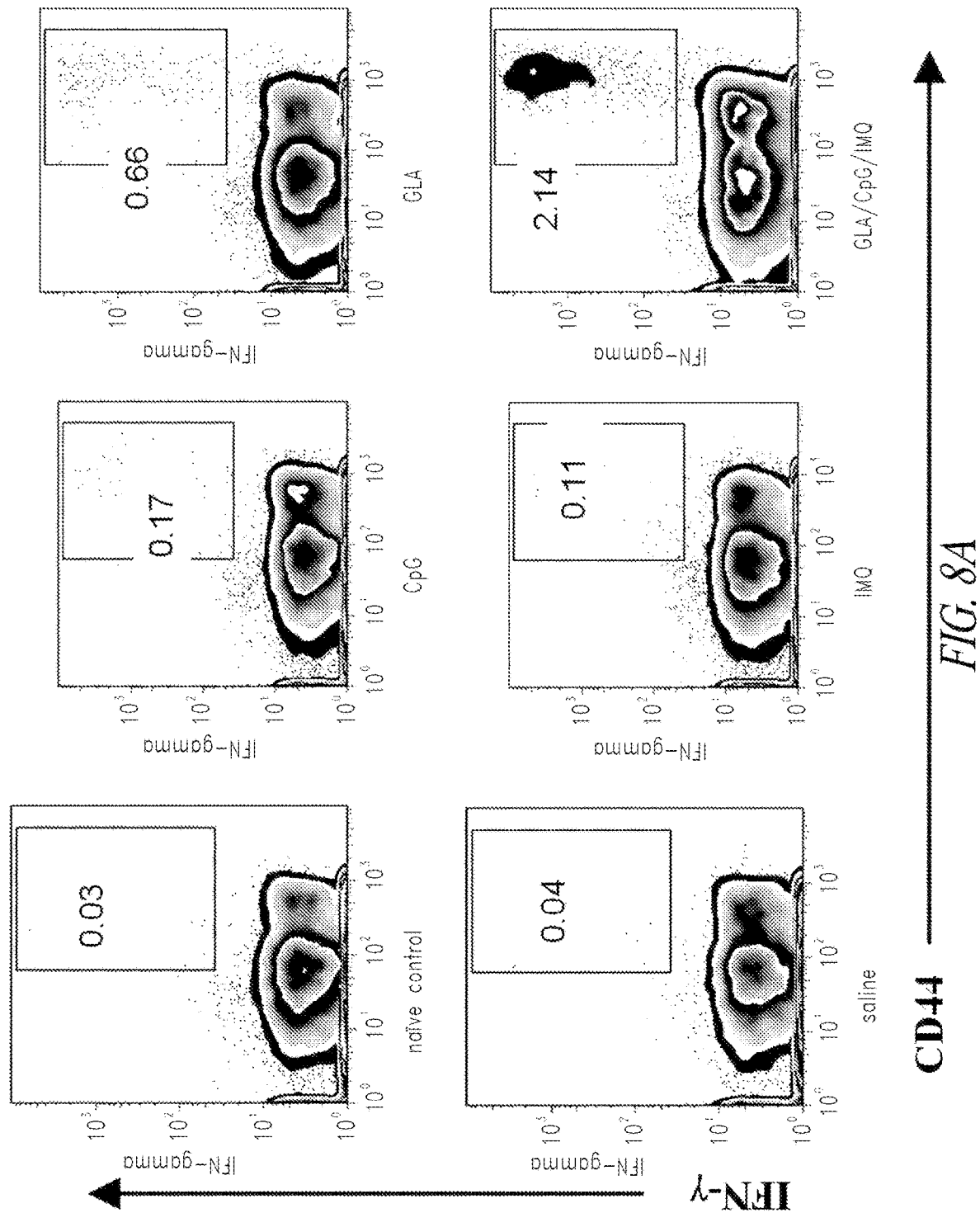
Figure 8B:
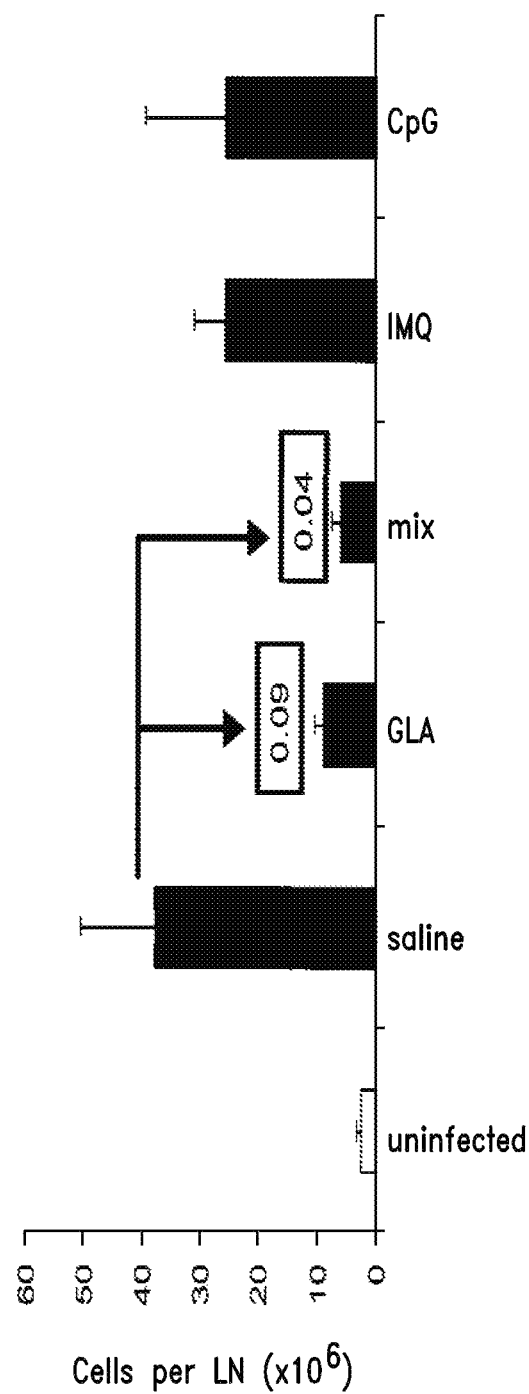

FIG. 8A shows ICS data demonstrating the frequencies of ML0276-specific IFN-γ cytokine producing CD4+ T cells induced in mice one week after the third immunization using ML0276 antigen formulated with aqueous formulations containing CpG, or Imiquimod (IMQ), or a stable oil emulsion containing GLA (GLA-SE), or the three mixed together, compared to saline and naïve controls. Splenocytes from C57BL/6 mice, immunized three times at three-week intervals with *M. leprea* ML0276 antigen (10 µg) formulated with CpG, Imiquimod (IMQ), GLA-SE, a combination of the three, or injected with saline, were cultured for 12 hrs in vitro in medium containing 10 mg/ml of ML0276. FIG. 8A shows cell levels of IFN-g in CD3+CD4+ T cells were detected by intracellular staining and measured by flow cytometry on a BD LSRII FACS. FIG. 8B shows draining lymph node cellularity as a correlate of protection.

FIGS. 9A and 9B show the surface expression of CD86 upon stimulation with GLA. Donor N003 CD14+ monocytes-derived primary dendritic cells were incubated for 44 hours with 10,000 ng/ml, 1000 ng/ml, 100 ng/ml, 10 ng/ml, 1 ng/ml, 0.1 ng/ml, or 0.01 ng/ml GLA (FIG. 9A) or MPL (FIG. 9B). A cytokine cocktail made of $PGE_2$, IL-1β, TNFα, and IL-6 was run as a positive control. Expression levels of the costimulatory molecule CD86 at the surface of DC were used as an indicator of cell activation and measured by flow cytometry on a LSRII instrument (BD Biosciences, San Jose, Calif.) using CD86-specific fluorochrome-labeled antibody (eBiosciences, San Diego, Calif.).

FIGS. 10A-10F show cultured human dendritic cells (DC) from three donors that show increased maturation with GLA stimulation. PBMC from three normal donors was purified for human CD14+ monocytes-derived primary dendritic cells and stimulated with GLA (FIGS. 10A-10C) or MPL (FIGS. 10D-10F). No stimulation was used as a negative control and a standard cytokine maturation cocktail of PGE2, IL-1β, TNFα, and IL-6 was run as a positive control. The percent maximum expression of CD86-specific fluorochrome-labeled antibody (eBiosciences, San Diego, Calif.) was used to monitor DC maturation by flow cytometry on a LSRII instrument (BD Biosciences, San Jose, Calif.)

Figure 11:
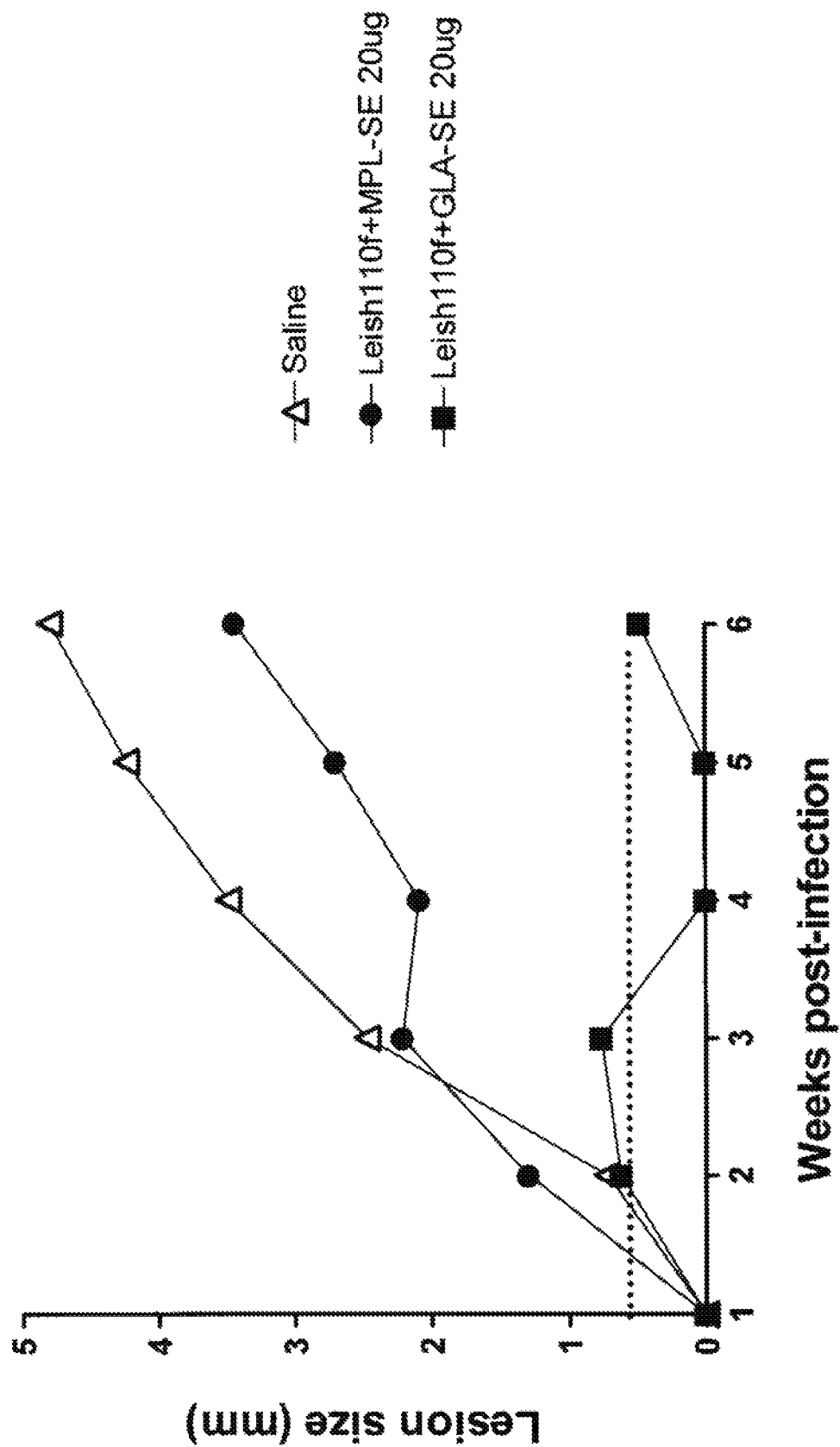

FIG. 11 shows the lesion development in mice vaccinated with Leish-110f+GLA-SE upon challenge with *L. major*. Four Balb/c mice per treatment group were immunized three times at two-week intervals with either saline or the Leish-110f antigen (10 µg per animal for each immunization) formulated in a stable emulsion containing 20 µg of (i) GLA (Avanti Polar Lipids, Inc., Alabaster, Ala.; product number 699800; GLA-SE), or (ii) MPL® in an emulsion as supplied by the manufacturer ("MPL-SE", GSK Biologicals, Rixensart, Belgium). Three weeks after the last injection, mice were challenged intradermally in the pinea of both ears with $2 \times 10^3$ purified *Leishmania major* clone V1 (MOHM/IL/80/Friedlin) metacyclic promastigotes. Development of cutaneous lesions was monitored weekly for 6 weeks post-infection.

Figure 12:
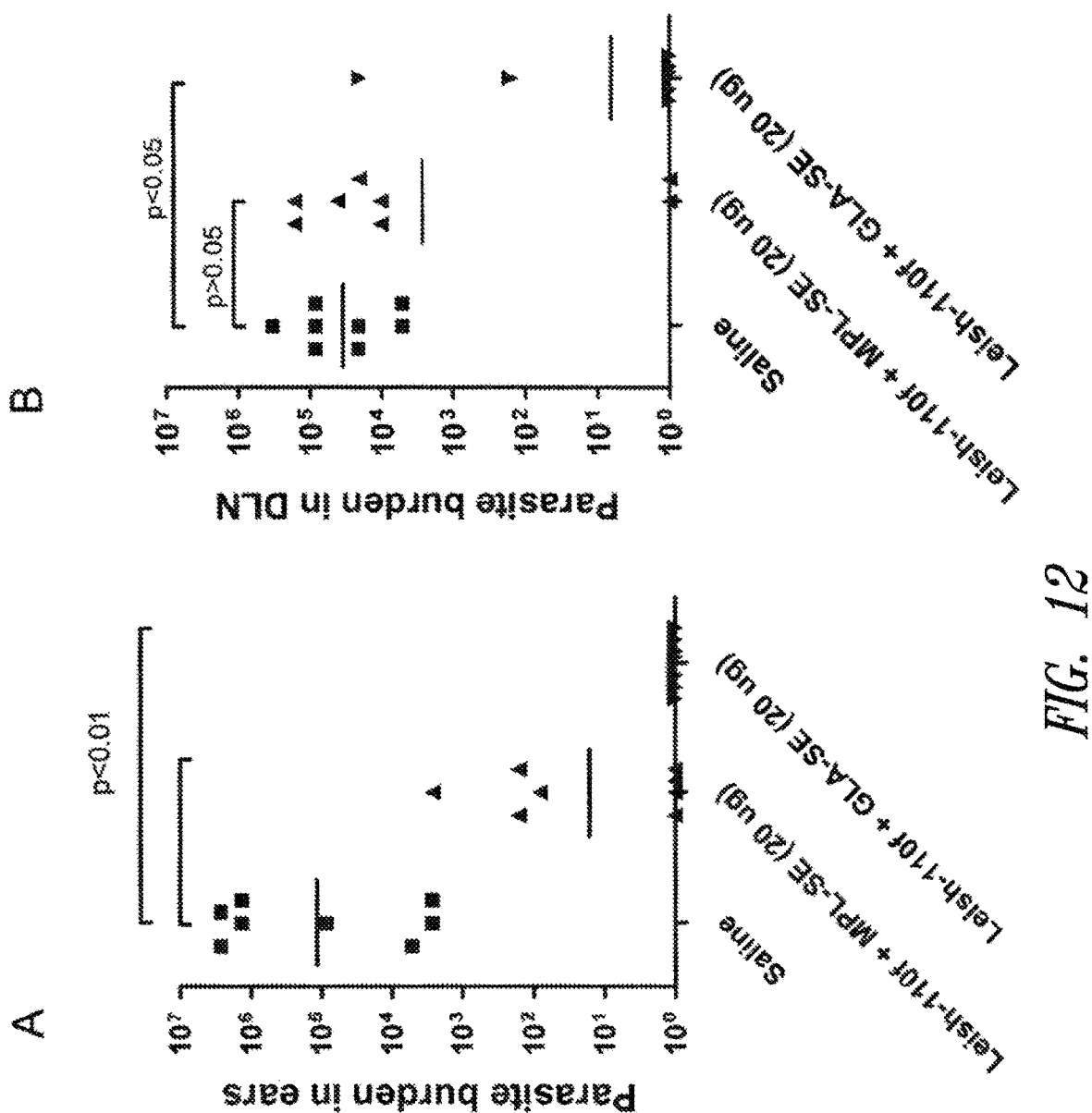
Figure 13A:
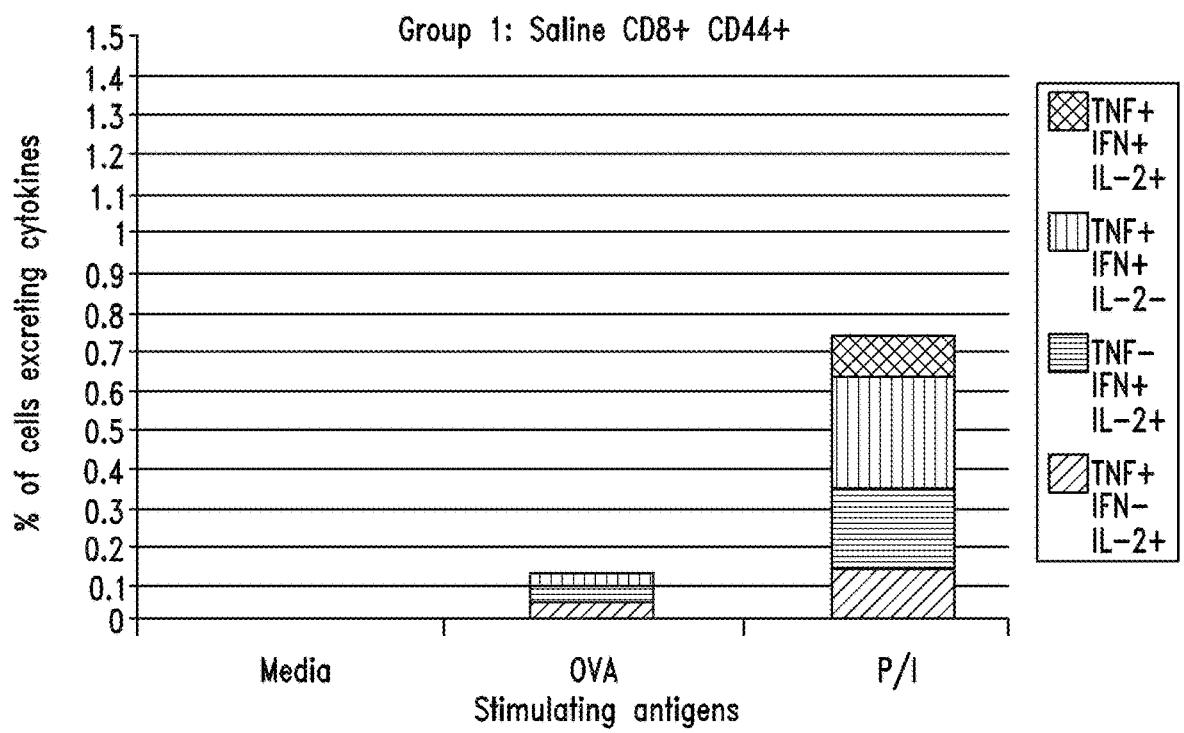
Figure 13B:
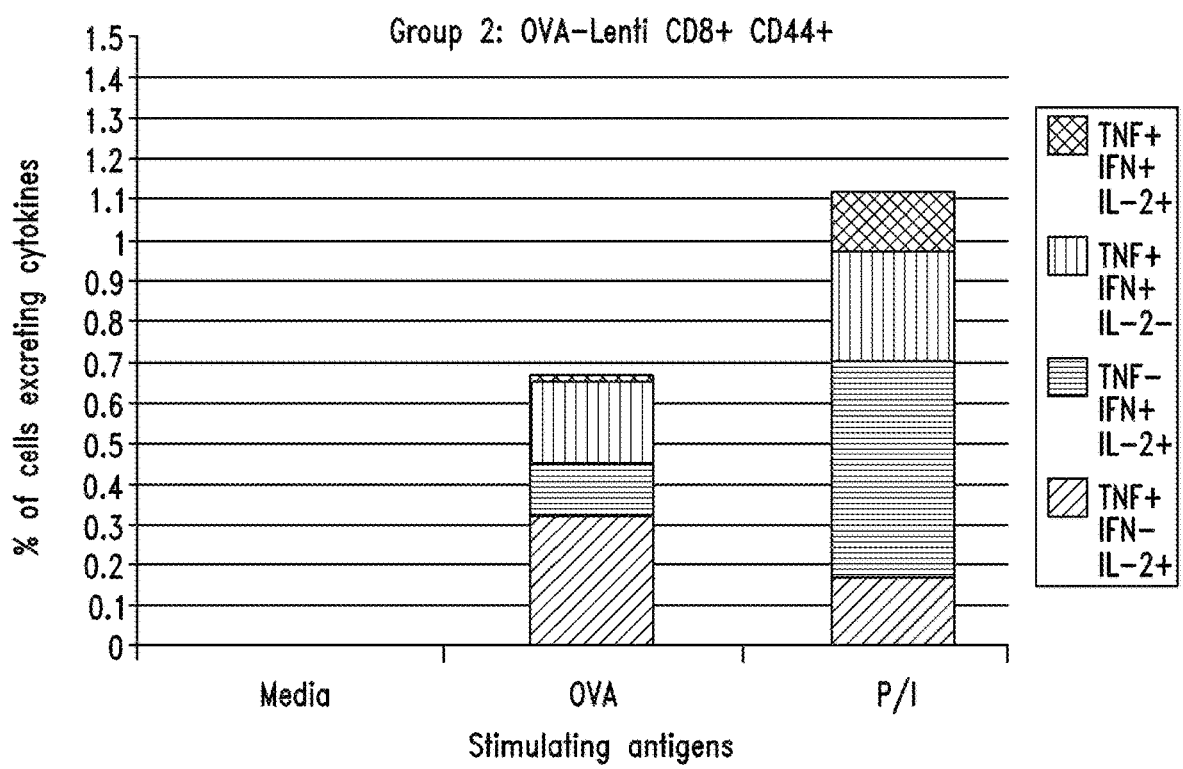
Figure 13C:
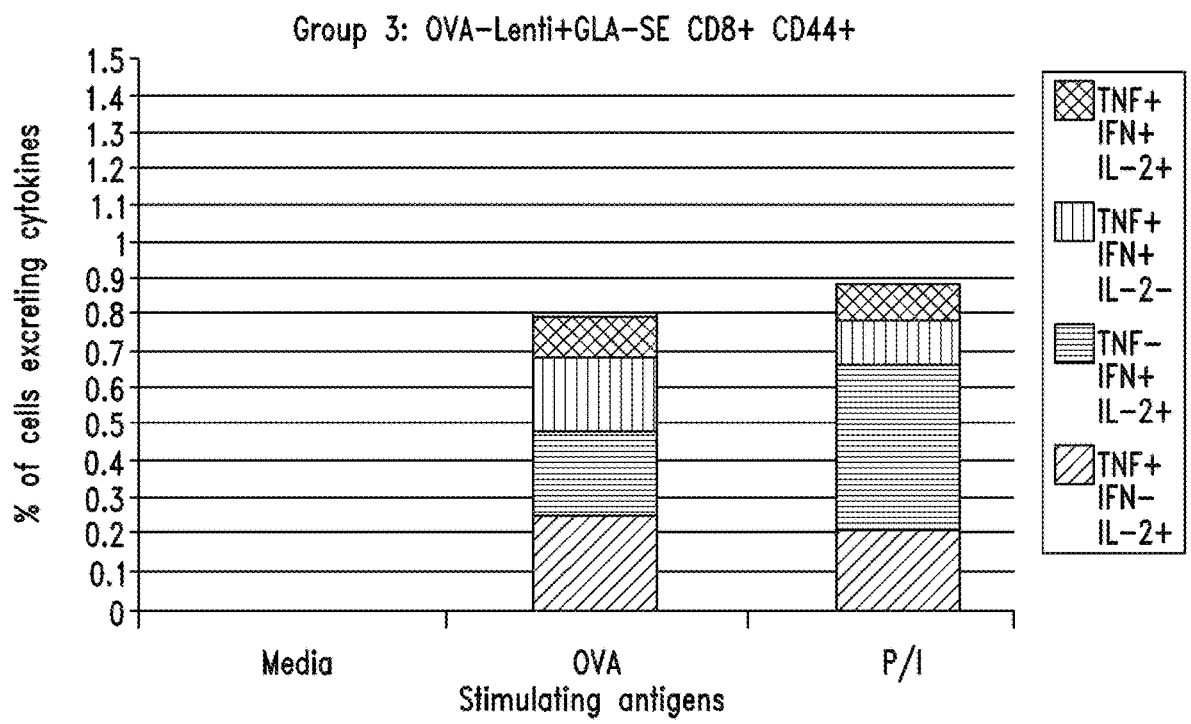
Figure 13D:
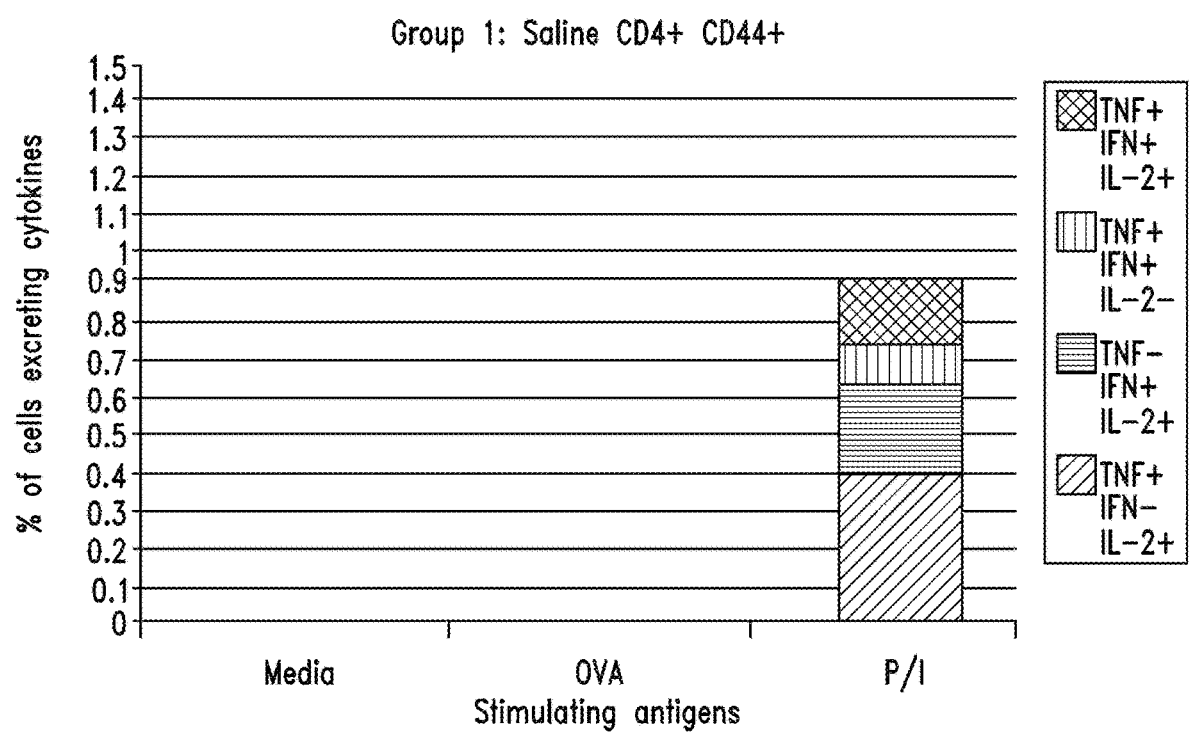
Figure 13E:
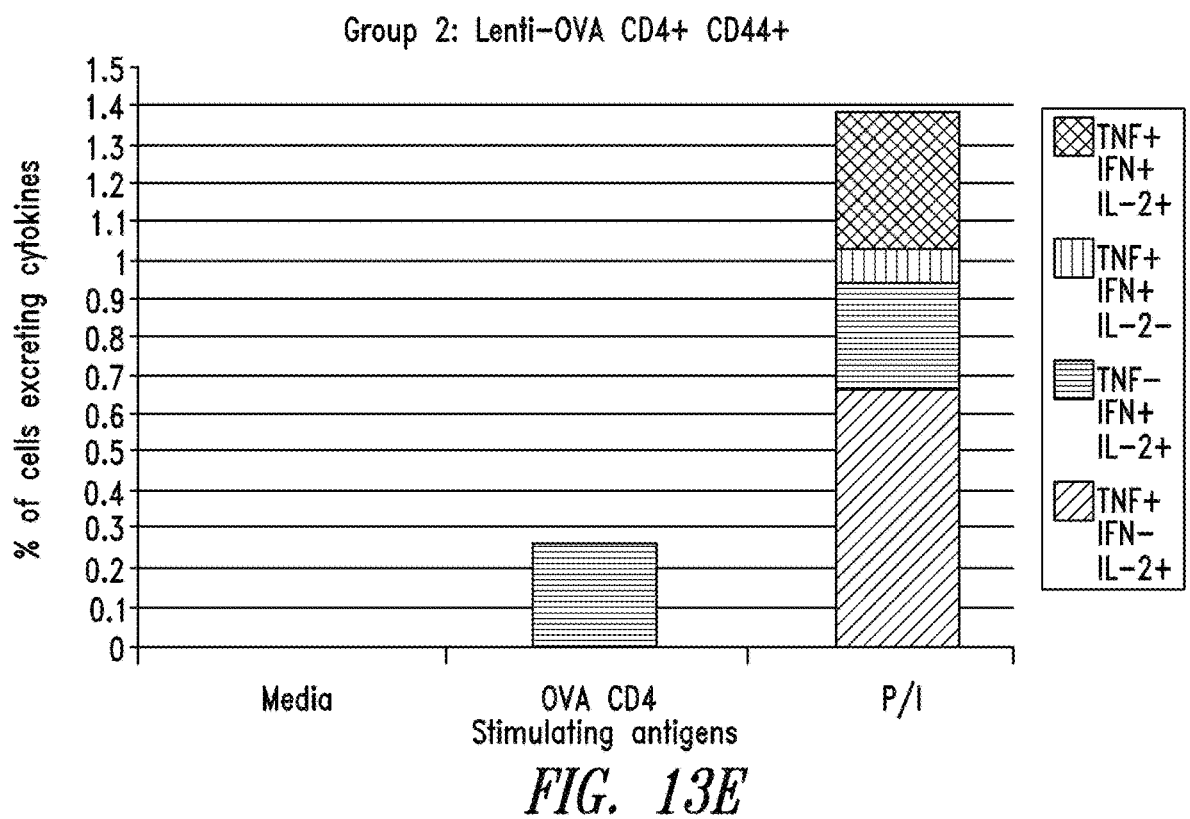
Figure 13F:
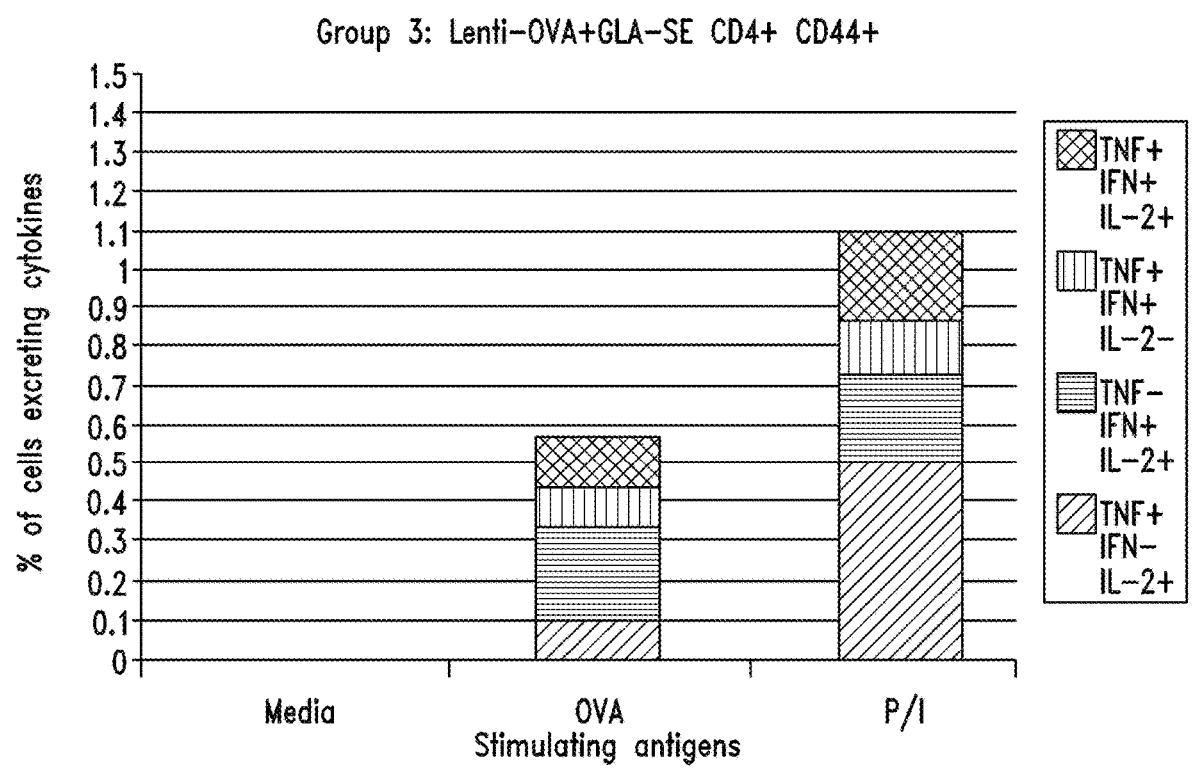

FIG. 12 shows parasite burden in mice vaccinated with Leish-110f+GLA-SE upon challenge with *L. major*. Four Balb/c mice per treatment group were immunized three times at two-week intervals with either saline or the Leish-110f antigen (10 µg per animal for each immunization) formulated in a stable emulsion containing 20 µg of (i) GLA (Avanti Polar Lipids, Inc., Alabaster, Ala.; product number 699800; GLA-SE), or (ii) MPL® in an emulsion as supplied by the manufacturer ("MPL-SE", GSK Biologicals, Rixensart, Belgium). Three weeks after the last injection, mice were challenged intradermally in the pinea of both ears with $2 \times 10^3$ purified *Leishmania major* clone V1 (MOHM/IL/80/Friedlin) metacyclic promastigotes. Parasite burden in the ear and draining lymph nodes of infected mice were determined 6 weeks post-infection. Individual counts and mean are shown for each group. Student's t test was performed and differences between groups were considered statistically significant when p<0.05.

FIGS. 13A-13F show a flow cytometry analysis of OVA-specific T-cells. Single-cell analysis of OVA-specific CD8+ and CD4+ T cells producing single, double or triple Th1-type cytokines are shown. IFN-γ, IL-2 and TNF-α production by CD8+(FIGS. 13A-13C) and CD4+(FIGS. 13D-13F) T cells in response to in vitro stimulation with medium, P/I or OVA were evaluated by flow cytometry. Splenocytes were purified from mice that were injected with saline, lentiviral vaccine or lentiviral vaccine plus GLA-SE, and were incubated in the presence of anti-CD28 and anti-CD49d with the addition of medium or OVA.

Figure 14A:
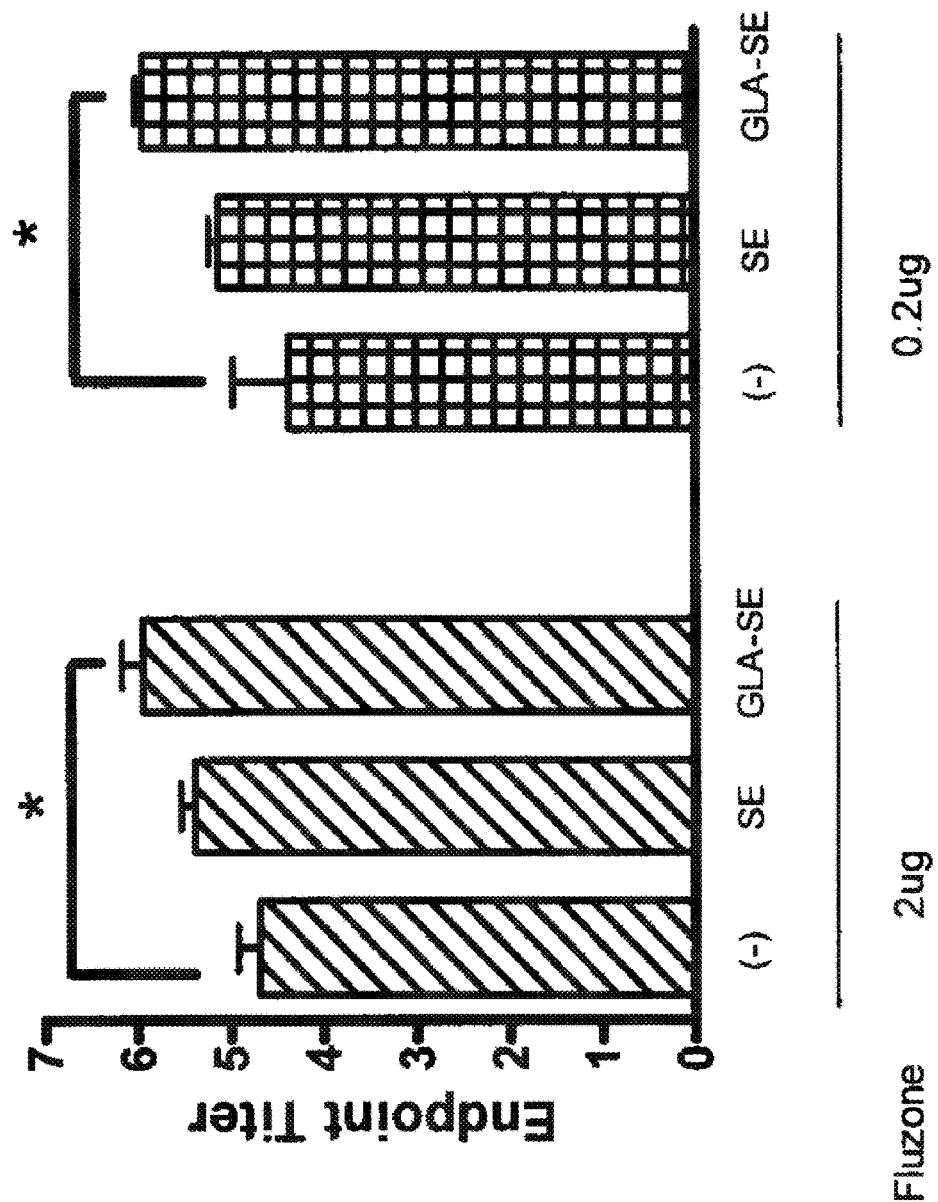
Figure 14B:
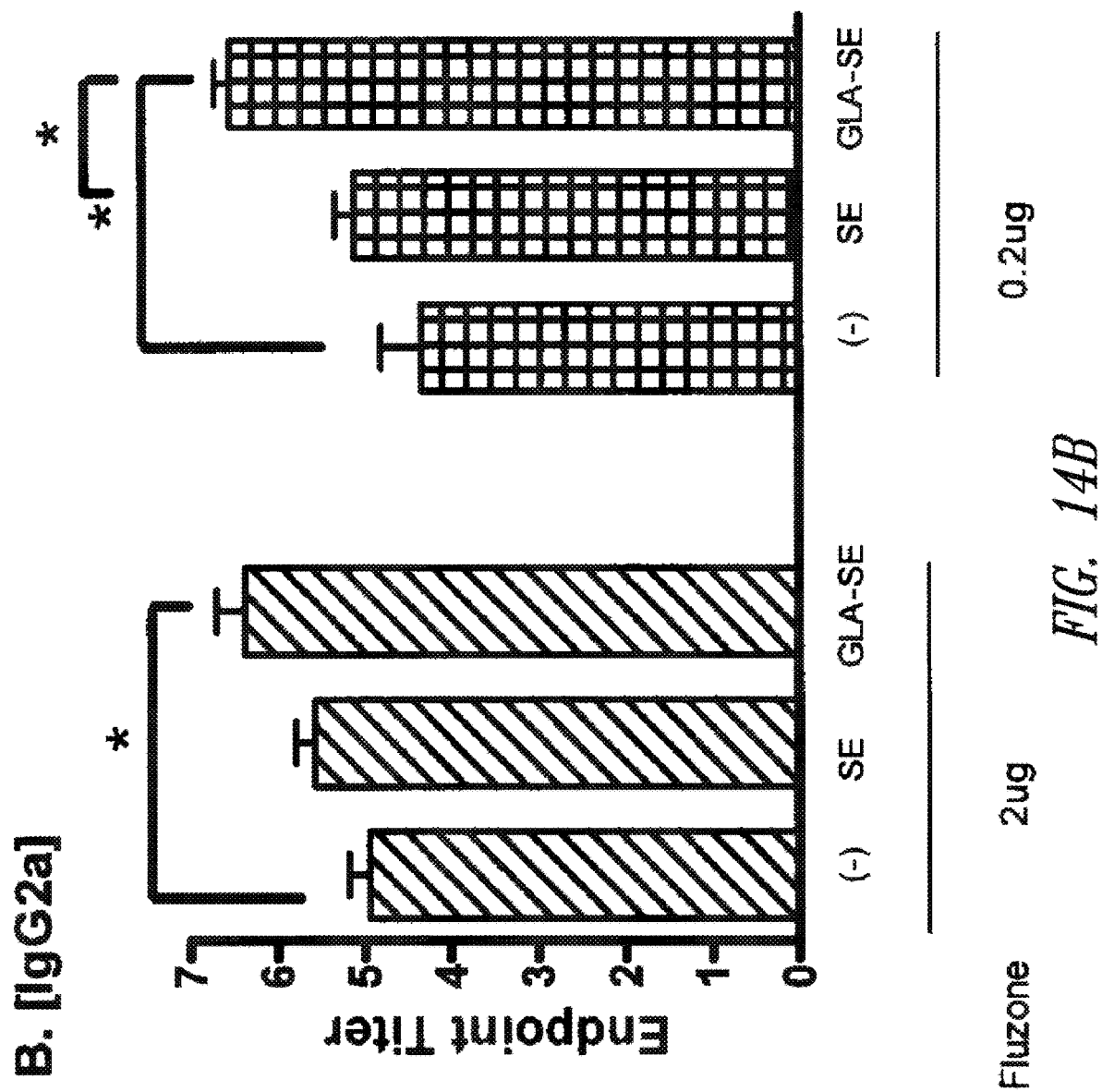
Figure 14C:
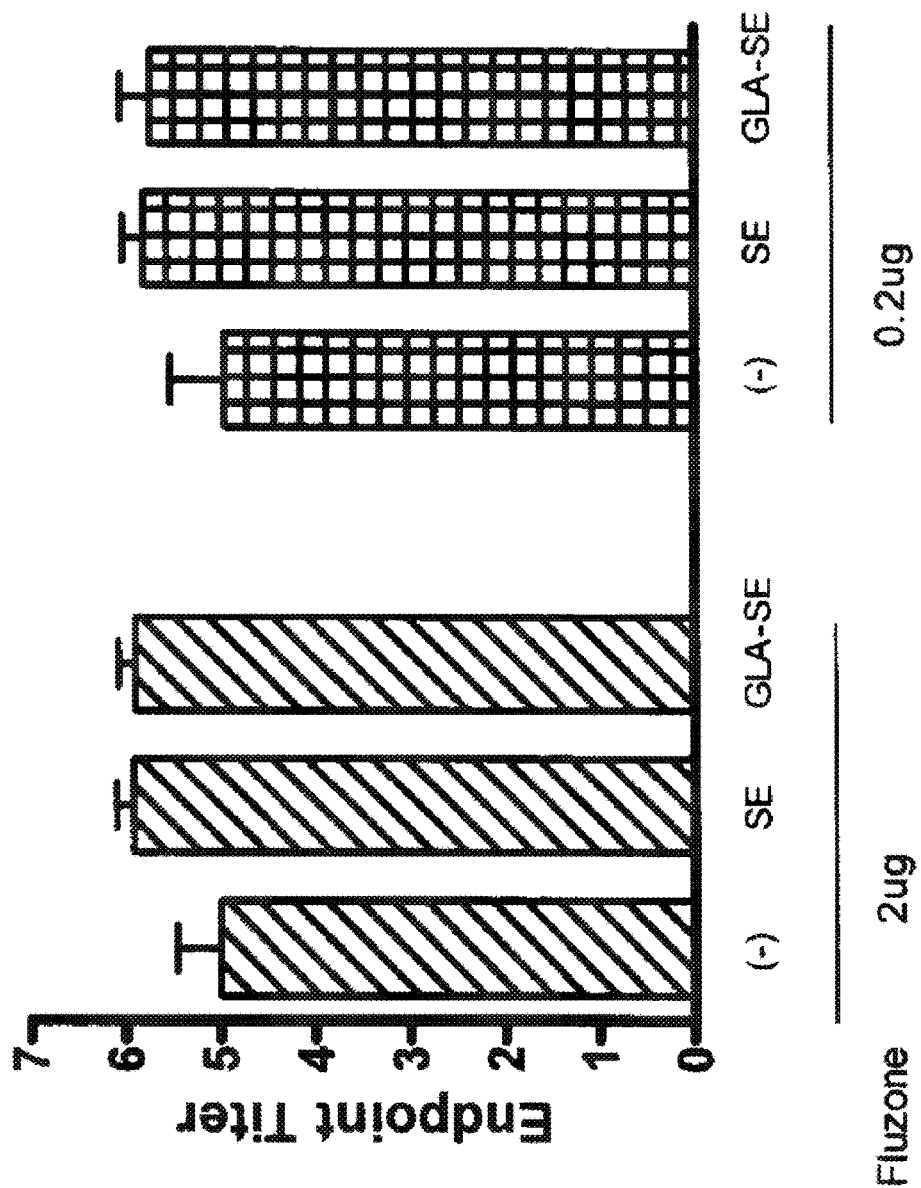
Figure 14D:
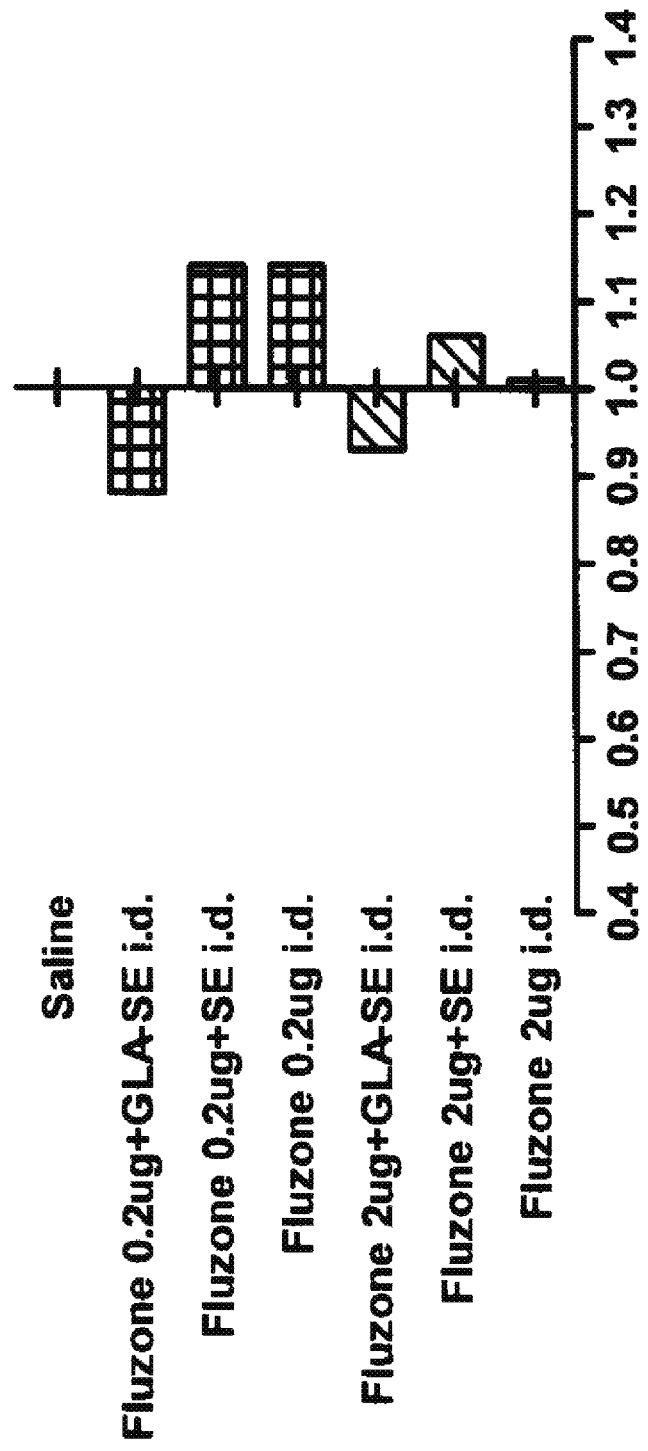
Figure 15A:
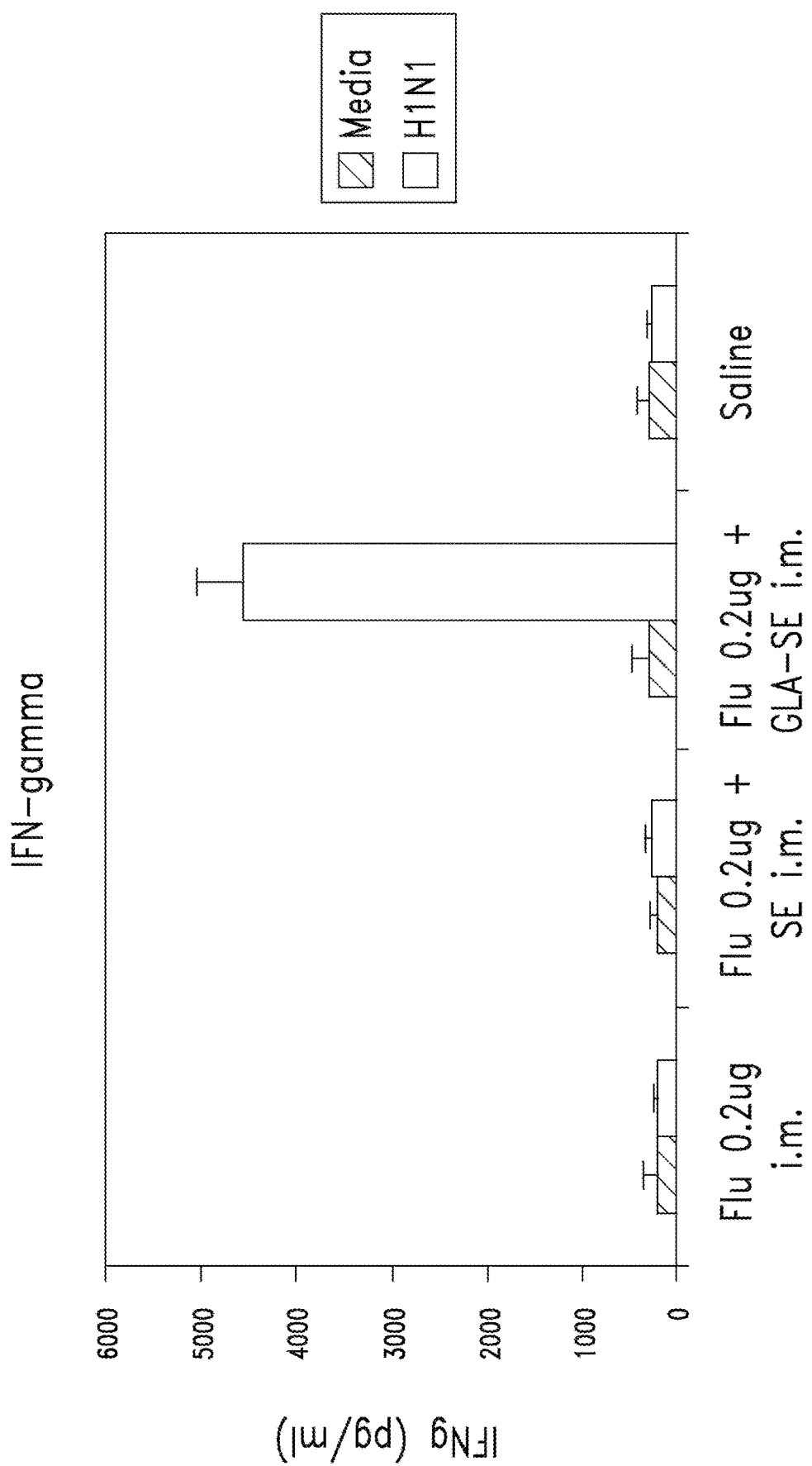
Figure 15B:
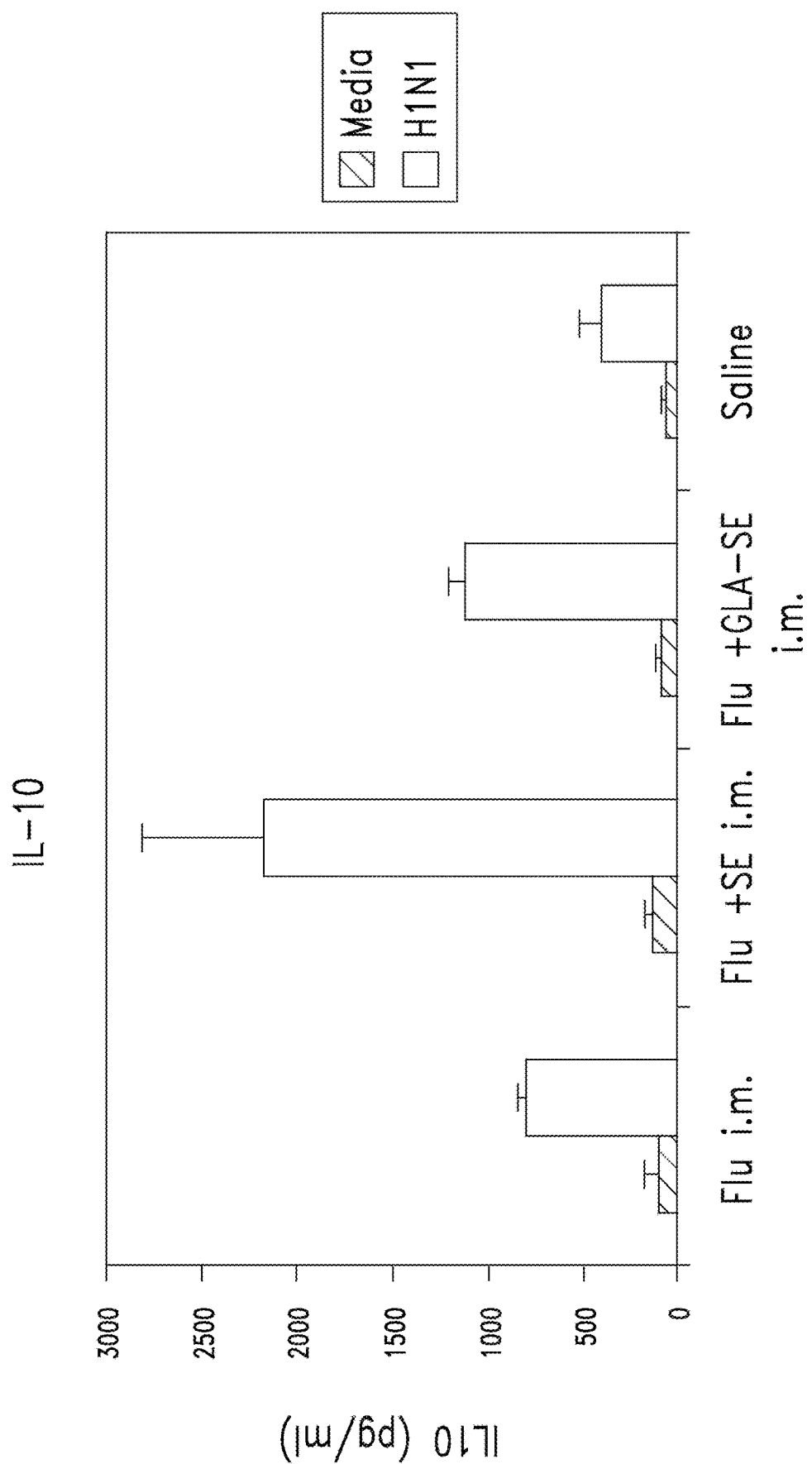
Figure 15C:
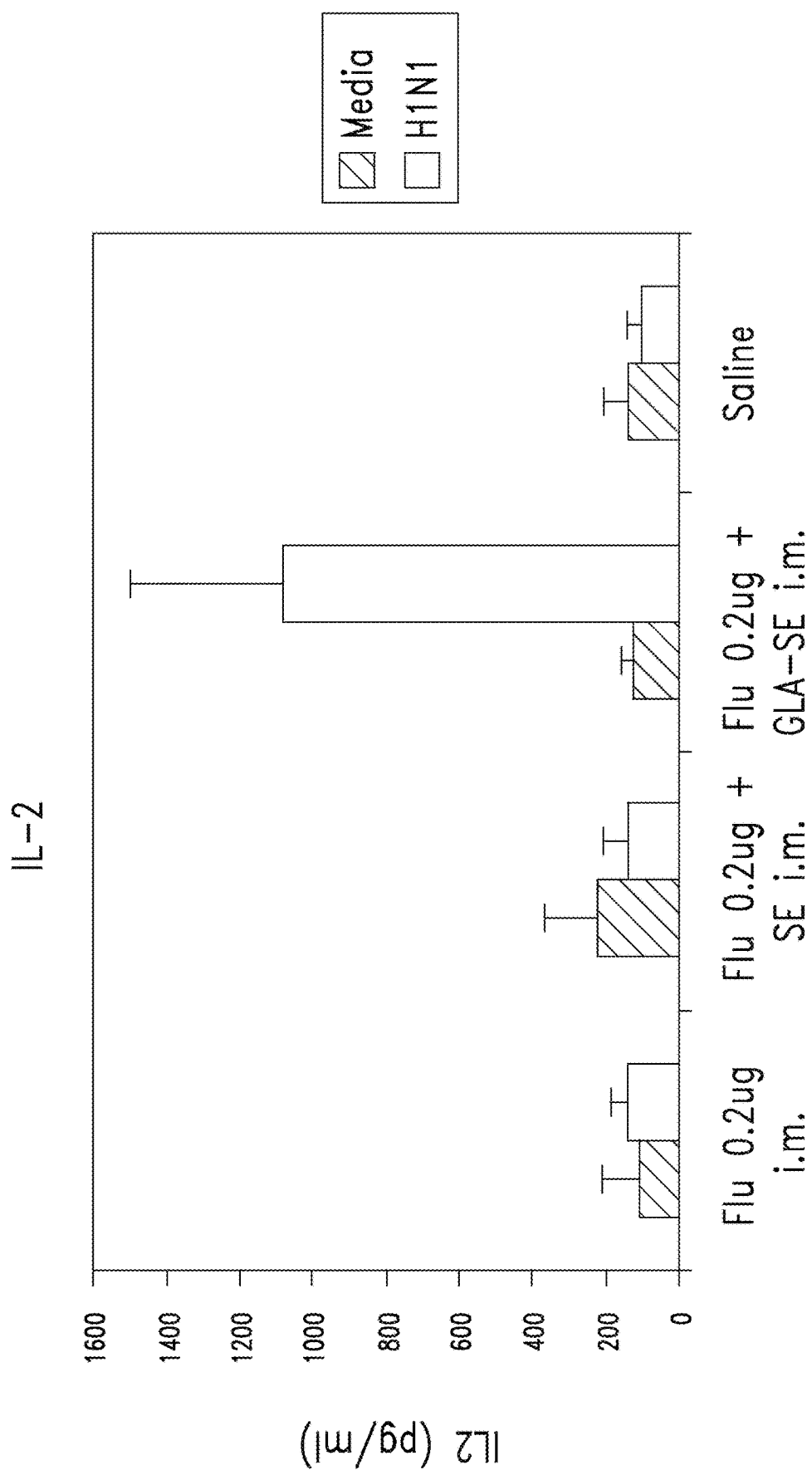
Figure 15D:
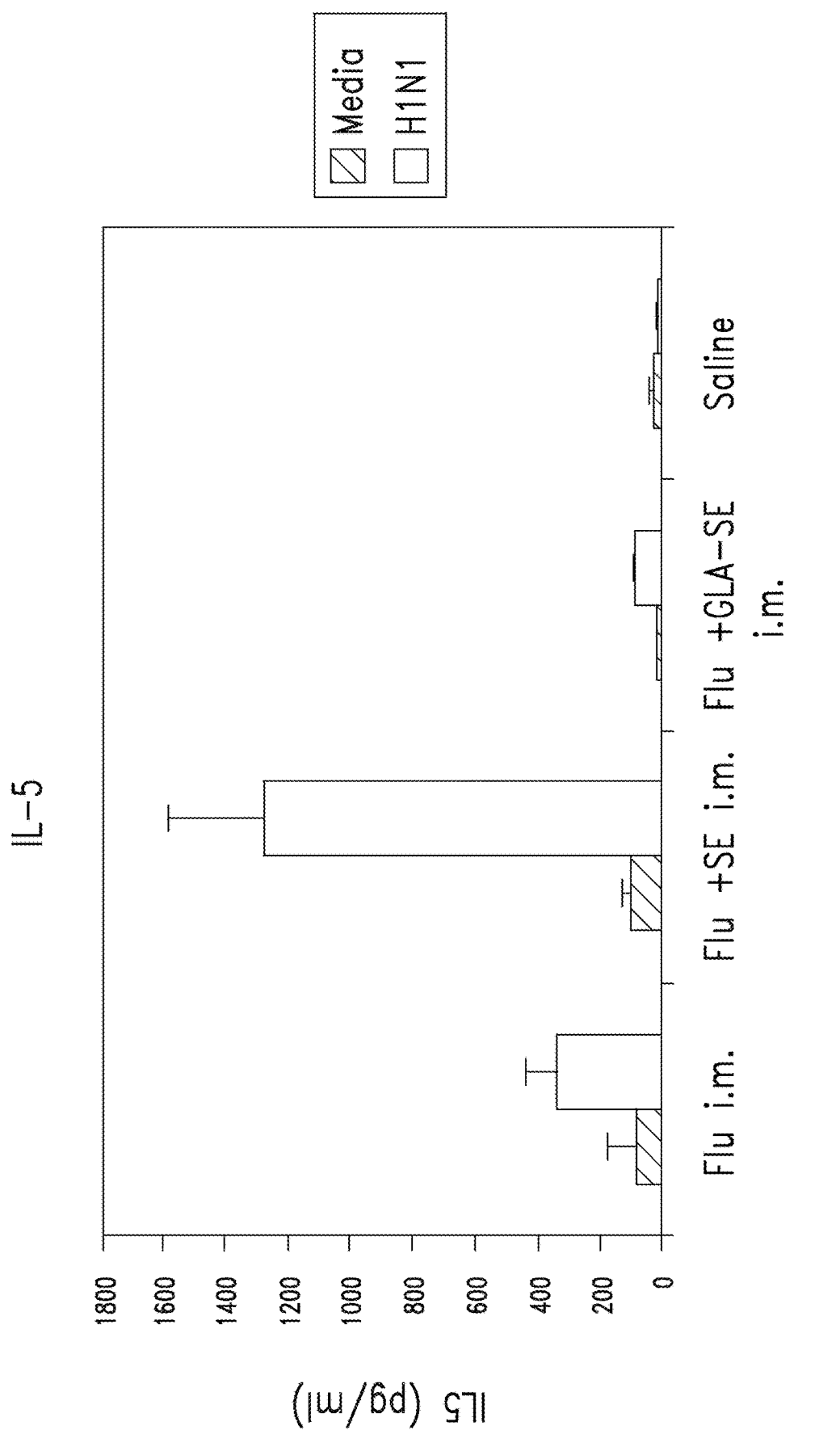

FIGS. 14A-14D show anti-Fluzone IgG antibody levels seven days following a boost immunization with Fluzone (two doses; 2 µg and 0.2 µg) given intradermally (i.d.) with and without adjuvant. FIG. 14A shows Fluzone-specific IgG antibody responses; FIG. 14B shows Fluzone-specific IgG2a responses; FIG. 14C shows Fluzone-specific IgG1 responses; and FIG. 14D shows IgG1:IgG2a ratios (results <1.0 represent an IgG2a dominant response; results >1.0 represent an IgG1 dominant response). Asterisks represent statistical significance, p<0.05.

FIGS. 15A-15D show cytokine levels for IFN-γ (FIG. 15A), IL-10 (FIG. 15B), IL-2 (FIG. 15C), and IL-5 (FIG. 15D) from ex vivo stimulated splenocytes 3 weeks following an intramuscular (i.m.) boost immunization with Fluzone (0.2 µg) plus GLA-SE (5 µg). The average cytokine levels from three individual Balb/c mice per treatment group ±s.d. are shown.

DETAILED DESCRIPTION OF THE INVENTION

The present invention in its several embodiments provides vaccine compositions, adjuvant compositions, and related methods that include the use of a synthetic glucopyranosyl lipid adjuvant (GLA). GLA provides a synthetic immunological adjuvant which, advantageously relative to adjuvants of the prior art, and in particular, relative to natural product adjuvants, can be prepared in substantially homogeneous form. Moreover, GLA can be prepared efficiently and economically through large-scale synthetic chemical manufacturing, unlike natural product-derived adjuvants. As a synthetic adjuvant that is chemically synthesized from defined starting materials to obtain a chemically defined product that exhibits qualitative and quantitative batch-to-batch consistency, GLA thus offers unprecedented benefits including improved product quality control. Surprisingly, although 3-acylated monophosphorylated lipid A has been associated with certain toxicities, it has been found that when the 2 amine position contains a single acyl chain, the molecules retain acceptable safety profiles. Further, the synthesis of such compounds is simplified because specific deacylation at the 3 position presents technical challenges. Thus, the invention offers further advantages in terms of safety and ease of synthesis.

As described herein, GLA-containing compositions and methods for their use include in some embodiments the use of GLA by itself with a pharmaceutically acceptable carrier or excipient for immunological adjuvant activity, including "adjuvanting" in which GLA administration to a subject may be wholly independent of, and/or separated temporally and/or spatially from, administration to the subject of one or more antigens against which elicitation or enhancement of an immune response (e.g., an antigen-specific response) in the subject is desired. Other embodiments include the use of GLA in a vaccine composition that also includes one or a plurality of antigens to which an immune response elicited or enhanced by such a vaccine is desired. As described herein, these vaccine compositions may in certain related embodiments also include one or more toll-like receptor (TLR) agonist and/or one or a plurality of one or more of a co-adjuvant, an imidazoquinoline immune response modifier, and a double stem loop immune modifier (dSLIM). In other related embodiments, a vaccine composition as provided herein may comprise GLA and one or more recombinant expression constructs each comprising a promoter operably linked to a nucleic acid sequence encoding the antigen against which elicitation or enhancement of an immune response (e.g., an antigen-specific response) in the subject is desired.

GLA

As also noted above, as a chemically synthesized adjuvant GLA can be prepared in substantially homogeneous form, which refers to a GLA preparation that is at least 80%, preferably at least 85%, more preferably at least 90%, more preferably at least 95% and still more preferably at least 96%, 97%, 98% or 99% pure with respect to the GLA molecule.

In certain embodiments, GLA comprises (i) a diglucosamine backbone having a reducing terminus glucosamine linked to a non-reducing terminus glucosamine through an ether linkage between hexosamine position 1 of the non-reducing terminus glucosamine and hexosamine position 6 of the reducing terminus glucosamine; (ii) an O-phosphoryl group attached to hexosamine position 4 of the non-reducing terminus glucosamine; and (iii) up to six fatty acyl chains; wherein one of the fatty acyl chains is attached to 3-hydroxy of the reducing terminus glucosamine through an ester linkage, wherein one of the fatty acyl chains is attached to a 2-amino of the non-reducing terminus glucosamine through an amide linkage and comprises a tetradecanoyl chain linked to an alkanoyl chain of greater than 12 carbon atoms through an ester linkage, and wherein one of the fatty acyl chains is attached to 3-hydroxy of the non-reducing terminus glucosamine through an ester linkage and comprises a tetradecanoyl chain linked to an alkanoyl chain of greater than 12 carbon atoms through an ester linkage. Determination of the degree of purity of a given GLA preparation can be readily made by those familiar with the appropriate analytical chemistry methodologies, such as by gas chromatography, liquid chromatography, mass spectroscopy and/or nuclear magnetic resonance analysis.

In certain embodiments, a GLA as used herein may have the following general structural formula:

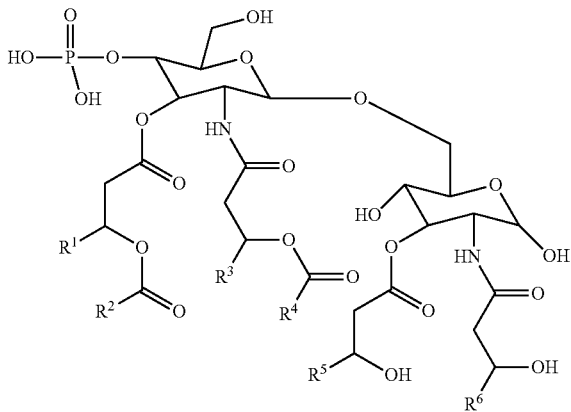

where $R^1$, $R^3$, $R^5$ and $R^6$ are $C_{11}$-$C_{20}$ alkyl; and $R^2$ and $R^4$ are $C_{12}$-$C_{20}$ alkyl.

In a more specific embodiment, the GLA has the formula set forth above wherein $R^1$, $R^3$, $R^5$ and $R^6$ are $C_{11-14}$ alkyl; and $R^2$ and $R^4$ are $C_{12-15}$ alkyl.

In a more specific embodiment, the GLA has the formula set forth above wherein $R^1$, $R^3$, $R^5$ and $R^6$ are $C_{11}$ alkyl; and $R^2$ and $R^4$ are $C_{13}$ alkyl.

As demonstrated herein, it has unexpectedly been found that GLA has surprisingly superior immunostimulatory activity when compared to MPL, while maintaining similar or reduced toxicity. For example, in certain embodiments, the GLA is effective for inducing an immune response that is at least 2-fold, at least 3-fold, at least 5-fold or at least 10-fold more potent than is induced using MPL at substantially the same or similar concentration. In other specific embodiments, the GLA has substantially the same or similar activity as MPL at concentrations at least 5-fold, at least 10-fold, at least 25-fold or at least 100-fold lower than MPL.

Immune responses may be measured using any of a variety of known immunological assays or parameters known in the art and/or described herein. For example, immune responses may be detected by any of a variety of well known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); or any other criterion by which the presence of an immune response may be detected. In a specific embodiment, an immune response is detected by measuring the induction of soluble mediators such as cytokines and/or chemokines (e.g., IFN-γ, IL-2, TNF, IL-1β, etc.). In another particular embodiment, an immune response may be detected by measuring in vivo protection from disease in an appropriate animal model.

GLA can be obtained commercially, for example, from Avanti Polar Lipids, Inc. (Alabaster, Ala.; product number 699800, wherein where $R^1$, $R^3$, $R^5$ and $R^6$ are undecyl and $R^2$ and $R^4$ are dodecyl).

"Alkyl" means a straight chain or branched, noncyclic or cyclic, unsaturated or saturated aliphatic hydrocarbon containing from 1 to 20 carbon atoms, and in certain preferred embodiments containing from 11 to 20 carbon atoms. Representative saturated straight chain alkyls include methyl, ethyl, n-propyl, n-butyl, n-pentyl, n-hexyl, and the like, including undecyl, dodecyl, tridecyl, tetradecyl, pentadecyl, hexadecyl, heptadecyl, octadecyl, etc.; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like. Cyclic alkyls are also referred to herein as "homocycles" or "homocyclic rings." Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1-butynyl, and the like.

Accordingly, in certain embodiments contemplated herein GLA may have any of the above described structures, and in certain embodiments it is expressly contemplated that GLA may, and in certain other embodiments it is expressly contemplated that GLA may not, have any structure of a lipid adjuvant that is disclosed in one or more of U.S. Pat. No. 6,544,518, EP 1531158, WO 2001/036433, WO 97/11708, WO 95/14026, U.S. Pat. No. 4,987,237, JP 63010728, JP 07055906, WO 2000/013029, U.S. Pat. Nos. 5,530,113, 5,612,476, 5,756,718, 5,843,918, WO 96/09310, U.S. Pub. 2004/161776, U.S. Pub. No. 2003/170249, U.S. Pub. No. 2002/176867, WO 2002/032450, WO 2002/028424, WO 2002/016560, WO 2000/042994, WO 2000/025815, WO 2000?018929, JP 10131046, WO 93/12778, EP 324455, DE 3833319, U.S. Pat. Nos. 4,844,894, 4,629,722. According to certain embodiments GLA is not 3'-de-O-acylated.

Antigen

An antigen, for use in certain embodiments of the herein described vaccine compositions and methods employing GLA, may be any target epitope, molecule (including a biomolecule), molecular complex (including molecular complexes that contain biomolecules), subcellular assembly, cell or tissue against which elicitation or enhancement of immunoreactivity in a subject is desired. Frequently, the term antigen will refer to a polypeptide antigen of interest. However, antigen, as used herein, may also refer to a recombinant construct which encodes a polypeptide antigen of interest (e.g, an expression construct). In certain preferred embodiments the antigen may be, or may be derived from, or may be immunologically cross-reactive with, an infectious pathogen and/or an epitope, biomolecule, cell or tissue that is associated with infection, cancer, autoimmune disease, allergy, asthma, or any other condition where stimulation of an antigen-specific immune response would be desirable or beneficial.

Preferably and in certain embodiments the vaccine formulations of the present invention contain an antigen or antigenic composition capable of eliciting an immune response against a human or other mammalian pathogen, which antigen or antigenic composition may include a composition derived from a virus such as from HIV-1, (such as tat, nef, gp120 or gp160), human herpes viruses, such as gD or derivatives thereof or Immediate Early protein such as ICP27 from HSV1 or HSV2, cytomegalovirus ((esp. Human)(such as gB or derivatives thereof), Rotavirus (including live-attenuated viruses), Epstein Barr virus (such as gp350 or derivatives thereof), Varicella Zoster Virus (such as gpI, II and 1E63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, etc.), flaviviruses (e.g., Yellow Fever Virus, Dengue Virus, Tick-borne encephalitis virus, Japanese Encephalitis Virus) or Influenza virus (whole live or inactivated virus, split influenza virus, grown in eggs or MDCK cells, or whole flu virosomes (as described by Gluck, *Vaccine*, 1992, 10, 915-920) or purified or recombinant proteins thereof, such as HA, NP, NA, or M proteins, or combinations thereof).

In certain other preferred embodiments the vaccine formulations of the present invention contain an antigen or antigenic composition capable of eliciting an immune response against a human or other mammlian pathogen, which antigen or antigenic composition may include a composition derived from one or more bacterial pathogens such as *Neisseria* spp, including *N. gonorrhea* and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans: H. ducreyi; Moraxella* spp, including *M. catarrhalis*, also known as *Branhamella catarrhalis* (for example high and low molecular weight adhesins and invasins); *Bordetella* spp, including *B. pertussis* (for example pertactin, pertussis toxin or derivatives thereof, filamenteous hemagglutinin, adenylate cyclase, fimbriae), *B. parapertussis* and *B. bronchiseptica; Mycobacterium* spp., including *M. tuberculosis* (for example ESAT6, Antigen 85A, -B or -C), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp., including *C. jejuni* (for example toxins, adhesins and invasins) and *C. coli; Salmonella* spp, including *S. typhi, S. paratyphi, S. choleraesuis, S. enteritidis; Listeria* spp., including *L. monocytogenes; Helicobacter* spp, including *H. pylori* (for example urease, catalase, vacuolating toxin); *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example *botulinum* toxin and derivative thereof), *C. difficile* (for example *clostridium* toxins A or B and derivatives thereof); *Bacillus* spp., including *B. anthracis* (for example *botulinum* toxin and derivatives thereof); *Corynebacterium* spp., including *C. diphtheriae* (for example diphtheria toxin and derivatives thereof); *Borrelia* spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human Granulocytic Ehrlichiosis; *Rickettsia* spp, including *R. rickettsii; Chlamydia* spp. including *C. trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae*; or other bacterial pathogens. In certain other preferred embodiments the vaccine formulations of the present invention contain an antigen or antigenic composition capable of eliciting an immune response against a human or other mammalian pathogen, which antigen or antigenic composition may include a composition derived from one or more parasites (See, e.g., John, D. T. and Petri, W. A., *Markell and Voge's Medical Parasitology*—9th Ed., 2006, WB Saunders, Philadelphia; Bowman, D. D., *Georgis' Parasitology for Veterinarians*—

8th Ed., 2002, WB Saunders, Philadelphia) such as *Plasmodium* spp., including *P. falciparum; Toxoplasma* spp., including *T. gondii* (for example SAG2, SAG3, Tg34); *Entamoeba* spp., including *E. histolytica; Babesia* spp., including *B. microti; Trypanosoma* spp., including *T. cruzi; Giardia* spp., including *G. lamblia; Leshmania* spp., including *L. major; Pneumocystis* spp., including *P. carinii; Trichomonas* spp., including *T. vaginalis*; or from a helminth capable of infecting a mammal, such as: (i) nematode infections (including, but not limited to, *Enterobius vermicularis, Ascaris lumbricoides, Trichuris trichiura, Necator americanus, Ancylostoma duodenale, Wuchereria bancrofti, Brugia malayi, Onchocerca volvulus, Dracanculus medinensis, Trichinella spiralis*, and *Strongyloides stercoralis*); (ii) trematode infections (including, but not limited to, *Schistosoma mansoni, Schistosoma haematobium, Schistosoma japonicum, Schistosoma mekongi, Opisthorchis sinensis, Paragonimus* sp, *Fasciola hepatica, Fasciola magna, Fasciola gigantica*); and (iii) cestode infections (including, but not limited to, *Taenia saginata* and *Taenia solium*). Certain embodiments may therefore contemplate vaccine compositions that include an antigen derived from *Schisostoma* spp., *Schistosoma mansonii, Schistosoma haematobium*, and/or *Schistosoma japonicum*, or derived from yeast such as *Candida* spp., including *C. albicans; Cryptococcus* spp., including *C. neoformans*.

Other preferred specific antigens for *M. tuberculosis* are for example Th Ra12, Tb H9, Tb Ra35, Tb38-1, Erd 14, DPV, MTI, MSL, mTTC2 and hTCC1 (WO 99/51748). Proteins for *M. tuberculosis* also include fusion proteins and variants thereof where at least two, preferably three polypeptides of *M. tuberculosis* are fused into a larger protein. Preferred fusions include Ra12-TbH9-Ra35, Erd14-DPV-MTI, DPV-MTI-MSL, Erd14DPV-MTI-MSL-mTCC2, Erd14-DPV-MTI-MSL, DPV-MTI-MSL-mTCC2, TbH9-DPV-MTI (WO 99151748).

Most preferred antigens for *Chlamydia* include for example the High Molecular Weight Protein (HWMP) (WO 99/17741), ORF3 (EP 366 412), and putative membrane proteins (Pmps). Other *Chlamydia* antigens of the vaccine formulation can be selected from the group described in WO 99128475. Preferred bacterial vaccines comprise antigens derived from *Streptococcus* spp, including *S. pneumoniae* (for example capsular polysaccharides and conjugates thereof, PsaA, PspA, streptolysin, choline-binding proteins) and the protein antigen Pneumolysin (*Biochem Biophys Acta*, 1989, 67, 1007; Rubins et al., *Microbial Pathogenesis*, 25, 337-342), and mutant detoxified derivatives thereof (WO 90/06951; WO 99/03884). Other preferred bacterial vaccines comprise antigens derived from *Haemophilus* spp., including *H. influenzae* type B (for example PRP and conjugates thereof), non typeable *H. influenzae*, for example OMP26, high molecular weight adhesins, P5, P6, protein D and lipoprotein D, and fimbrin and fimbrin derived peptides (U.S. Pat. No. 5,843,464) or multiple copy variants or fusion proteins thereof.

Derivatives of Hepatitis B Surface antigen are well known in the art and include, inter alia, those PreS1, Pars2 S antigens set forth described in European Patent applications EP-A414 374; EP-A-0304 578, and EP 198474. In one preferred aspect the vaccine formulation of the invention comprises the HIV-1 antigen, gp120, especially when expressed in CHO cells. In a further embodiment, the vaccine formulation of the invention comprises gD2t as hereinabove defined.

In a preferred embodiment of the present invention vaccines containing the claimed adjuvant comprise antigen derived from the Human Papilloma Virus (HPV) considered to be responsible for genital warts (HPV 6 or HPV 11 and others), and the HPV viruses responsible for cervical cancer (HPV16, HPV18 and others). Particularly preferred forms of genital wart prophylactic, or therapeutic, vaccine comprise L1 particles or capsomers, and fusion proteins comprising one or more antigens selected from the HPV 6 and HPV 11 proteins E6, E7, L1, and L2. Certain preferred forms of fusion protein include L2E7 as disclosed in WO 96/26277, and proteinD(1/3)-E7 disclosed in GB 9717953.5 (PCT/EP98/05285). A preferred HPV cervical infection or cancer, prophylaxis or therapeutic vaccine, composition may comprise HPV 16 or 18 antigens. For example, L1 or L2 antigen monomers, or L1 or L2 antigens presented together as a virus like particle (VLP) or the L1 alone protein presented alone in a VLP or caposmer structure. Such antigens, virus like particles and capsomer are per se known. See for example WO94/00152, WO94/20137, WO94/05792, and WO93/02184.

Additional early proteins may be included alone or as fusion proteins such as E7, E2 or preferably F5 for example; particularly preferred embodiments include a VLP comprising L1 E7 fusion proteins (WO 96/11272). Particularly preferred HPV 16 antigens comprise the early proteins E6 or F7 in fusion with a protein D carrier to form Protein D-E6 or E7 fusions from HPV 16, or combinations thereof; or combinations of E6 or E7 with L2 (WO 96/26277). Alternatively the HPV 16 or 18 early proteins E6 and E7, may be presented in a single molecule, preferably a Protein D-E6/E7 fusion. Such vaccine may optionally contain either or both E6 and E7 proteins front HPV 18, preferably in the form of a Protein D-E6 or Protein D-E7 fusion protein or Protein D E6/E7 fusion protein. The vaccine of the present invention may additionally comprise antigens from other HPV strains, preferably from strains HPV 31 or 33.

Vaccines of the present invention further comprise antigens derived from parasites that cause Malaria. For example, preferred antigens from *Plasmodia falciparum* include RTS,S and TRAP. RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus. Its full structure is disclosed in the International Patent Application No. PCT/EP92/02591, published as WO 93/10152 claiming priority from UK patent application No. 9124390.7. When expressed in yeast RTS is produced as a lipoprotein particle, and when it is co-expressed with the S antigen from HBV it produces a mixed particle known as RTS,S.

TRAP antigens are described in the International Patent Application No. PCT/GB89/00895 published as WO 90/01496. A preferred embodiment of the present invention is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27125, Pfs16, Pfs48/45, Pfs230 and their analogues in *Plasmodium* spp.

Accordingly, certain herein disclosed embodiment contemplate an antigen that is derived from at least one infectious pathogen such as a bacterium, a virus or a fungus, including an *Actinobacterium* such as *M. tuberculosis* or *M. leprae* or another *Mycobacterium*; a bacterium such as a member of the genus *Salmonella, Neisseria, Borrelia, Chlamydia* or *Bordetella*; a virus such as a herpes simplex virus, a human immunodeficiency virus (HIV), a feline immunodeficiency virus (FIV), cytomegalovirus, Varicella Zoster Virus, hepatitis virus, Epstein Barr Virus (EBV), respiratory syncytial virus, human papilloma virus (HPV) and a cytomegalovirus; HIV such as HIV-1 or HIV-2; a fungus such as *Aspergillus, Blastomyces, Coccidioides* and Pneumocysti or a yeast, including *Candida* species such as *C. albicans, C. glabrata, C. krusei, C. lusitaniae, C. tropicalis* and *C. parapsilosis*; a parasite such as a protozoan, for example, a *Plasmodium* species including *P. falciparum, P. vivax, P. malariae* and *P. ovale*; or another parasite such as one or more of *Acanthamoeba, Entamoeba histolytica, Angiostrongylus, Schistosoma mansonii, Schistosoma haematobium, Schistosoma japonicum, Cryptosporidium, Ancylostoma, Entamoeba histolytica, Entamoeba coli, Entamoeba dispar, Entamoeba hartmanni, Entamoeba polecki, Wuchereria bancrofti, Giardia,* and *Leishmania.*

For example, in GLA-containing vaccine embodiments containing antigens derived from *Borrelia* sp., the antigens may include nucleic acid, pathogen derived antigen or antigenic preparations, recombinantly produced protein or peptides, and chimeric fusion proteins. One such antigen is OspA. The OspA may be a full mature protein in a lipidated form by virtue of its biosynthesis in a host cell (Lipo-OspA) or may alternatively be a non-lipidated derivative. Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

Compositions and methods are known in the art for identifying subjects having, or suspected of being at risk for having, an infection with an infectious pathogen as described herein.

For example, the bacterium *Mycobacterium tuberculosis* cases tuberculosis (TB). The bacteria usually attack the lungs but can also attack the kidney, spine, and brain. If not treated properly, TB disease can be fatal. The disease is spread from one person to another in the air when an infected person sneezes or coughs. In 2003, more than 14,000 cases of TB were reported in the United States.

Although tuberculosis can generally be controlled using extended antibiotic therapy, such treatment is not sufficient to prevent the spread of the disease and concerns exist regarding the potential selection for antibiotic-resistant strains. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance. (e.g., U.S. Pat. No. 7,087,713)

Currently, vaccination with live bacteria is the most efficient method for inducing protective immunity against tuberculosis. The most common *Mycobacterium* employed for this purpose is *Bacillus* Calmette-Guerin (BCG), an avirulent strain of *Mycobacterium bovis.* However, the safety and efficacy of BCG is a source of controversy and some countries, such as the United States, do not vaccinate the general public. Diagnosis is commonly achieved using a skin test, which involves intradermal exposure to tuberculin PPD (protein-purified derivative). Antigen-specific T cell responses result in measurable induration at the injection site by 48 72 hours after injection, which indicates exposure to Mycobacterial antigens. Sensitivity and specificity have, however, been a problem with this test, and individuals vaccinated with BCG cannot be distinguished from infected individuals. (e.g., U.S. Pat. No. 7,087,713)

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. *Mycobacterium*-reactive CD4 T cells have been shown to be potent producers of gamma-interferon (IFN-gamma), which, in turn, has been shown to trigger the anti-mycobacterial effects of macrophages in mice. While the role of IFN-gamma in humans is less clear, studies have shown that 1,25-dihydroxy-vitamin D3, either alone or in combination with IFN-gamma or tumor necrosis factor-alpha, activates human macrophages to inhibit *M. tuberculosis* infection. Furthermore, it is known that IFN-gamma stimulates human macrophages to make 1,25-dihydroxy-vitamin D3. Similarly, IL-12 has been shown to play a role in stimulating resistance to *M. tuberculosis* infection. For a review of the immunology of *M. tuberculosis* infection, see Chan and Kaufmann, in Tuberculosis: Pathogenesis, Protection and Control, Bloom (ed.), ASM Press. Washington, D.C. (1994).

Existing compounds and methods for diagnosing tuberculosis or for inducing protective immunity against tuberculosis include the use of polypeptides that contain at least one immunogenic portion of one or more *Mycobacterium* proteins and DNA molecules encoding such polypeptides. Diagnostic kits containing such polypeptides or DNA sequences and a suitable detection reagent may be used for the detection of *Mycobacterium* infection in patients and biological samples. Antibodies directed against such polypeptides are also provided. In addition, such compounds may be formulated into vaccines and/or pharmaceutical compositions for immunization against *Mycobacterium* infection. (U.S. Pat. Nos. 6,949,246 and 6,555,653).

Malaria was eliminated in many parts of the world in the 1960s, but the disease still persists and new strains of the disease are emerging that are resistant to existing drugs. Malaria is a major public health problem in more than 90 countries. Nine out of ten cases of malaria occur in sub-Saharan Africa. More than one third of the world's population is at risk, and between 350 and 500 million people are infected with malaria each year. Forty-five million pregnant women are at risk of contracting malaria this year. Of those individuals already infected, more than 1 million of those infected die each year from what is a preventable disease. The majority of those deaths are children in Africa.

Malaria is usually transmitted when a person is bitten by an infected female *Anopheles* mosquito. To transmit the mosquito must have been infected by having drawn blood from a person already infected with malaria. Malaria is caused by a parasite and the clinical symptoms of the disease include fever and flu-like illness, such as chills, headache, muscle aches, and tiredness. These symptoms may be accompanied by nausea, vomiting, and diarrhea. Malaria can also cause anemia and jaundice because of the loss of red blood cells. Infection with one type of malaria, *Plasmodium falciparum,* if not promptly treated, may cause kidney failure, seizures, mental confusion, coma, and death.

An in vitro diagnostic method for malaria in an individual is known, comprising placing a tissue or a biological fluid taken from an individual in contact with a molecule or polypeptide composition, wherein said molecule or polypeptide composition comprises one or more peptide sequences bearing all or part of one or more T epitopes of the proteins resulting from the infectious activity of *P. falciparum*, under conditions allowing an in vitro immunological reaction to occur between said composition and the antibodies that may be present in the tissue or biological fluid, and in vitro detection of the antigen-antibody complexes formed (see, e.g., U.S. Pat. No. 7,087,231).

Expression and purification of a recombinant *Plasmodium falciparum* (3D7) AMA-1 ectodomain have been described. Previous methods have produced a highly purified protein which retains folding and disulfide bridging of the native molecule. The recombinant AMA-1 is useful as a diagnostic reagent as well as in antibody production, and as a protein for use alone, or as part of, a vaccine to prevent malaria. (U.S. Pat. No. 7,029,685)

Polynucleotides have been described in the art that encode species-specific *P. vivax* malarial peptide antigens which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether *Plasmodium vivax* is the species responsible for the infection. (U.S. Pat. No. 6,706,872) Species-specific *P. vivax* malarial peptide antigens have also been reported which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether *Plasmodium vivax* is the species responsible for the infection (see, e.g., U.S. Pat. No. 6,231,861).

A recombinant *Plasmodium falciparum* (3D7) AMA-1 ectodomain has also been expressed by a method that produces a highly purified protein which retains folding and disulfide bridging of the native molecule. The recombinant AMA-1 is useful as a diagnostic reagent, for use in antibody production, and as a vaccine. (U.S. Pat. No. 7,060,276) Similarly known are the expression and purification of a recombinant *Plasmodium falciparum* (3D7) MSP-1$_{42}$, which retains folding and disulfide bridging of the native molecule. The recombinant MSP-1$_{42}$ is useful as a diagnostic reagent, for use in antibody production, and as a vaccine. (U.S. Pat. No. 6,855,322).

Diagnostic methods for the detection of human malaria infections to identify a subject having or suspected of being at risk for having an infection with a malaria infectious pathogen are thus known according to these and related disclosures. Specifically, for example, blood samples are combined with a reagent containing 3-acetyl pyridine adenine dinucleotide (APAD), a substrate (e.g. a lactate salt or lactic acid), and a buffer. The reagent is designed to detect the presence of a unique glycolytic enzyme produced by the malaria parasite. This enzyme is known as parasite lactic acid dehydrogenase (PLDH). PLDH is readily distinguishable from host LDH using the above-described reagent. Combination of the reagent with a parasitized blood sample results in the reduction of APAD. However, APAD is not reduced by host LDH. The reduced APAD may then be detected by various techniques, including spectral, fluorimetric, electrophoretic, or colorimetric analysis. Detection of the reduced APAD in the foregoing manner provides a positive indication of malaria infection (e.g., U.S. Pat. No. 5,124,141). In another methodology for diagnosing malaria, a polypeptide comprising a characteristic amino acid sequence derived from the *Plasmodium falciparum* antigen GLURP, is recognized in a test sample by a specific antibody raised against or reactive with the polypeptide. (U.S. Pat. No. 5,231,168).

Leishmaniasis is a widespread parasitic disease with frequent epidemics in the Indian subcontinent, Africa, and Latin America and is a World Health Organization priority for vaccine development. A complex of different diseases, *Leishmania* parasites cause fatal infections of internal organs, as well as serious skin disease. One of the most devastating forms of leishmaniasis is a disfiguring infection of the nose and mouth. The number of cases of leishmaniasis are increasing, and it is now out of control in many areas. Leishmaniasis is also on the rise in some developed countries, specifically southern Europe as a result of HIV infection. Available drugs are toxic, expensive, and require long-term daily injections.

*Leishmania* are protozoan parasites that inhabit macrophages or the white blood cells of the immune system. The parasites are transmitted by the bite of small blood sucking insects (sand flies), which are difficult to control, as they inhabit vast areas of the planet.

Visceral leishmaniasis is the most dangerous of the three manifestations of the disease. It is estimated that about 500,000 new cases of the visceral form (kala-azar or "the killing disease") occur each year. More than 200 million people are currently at risk for contracting visceral leishmaniasis. Over 90 percent of visceral leishmaniasis cases occur in India, Bangladesh, Sudan, Brazil, and Nepal. Most of the deaths occur in children. Those with the cutaneous forms are often left permanently disfigured.

*Leishmania* infections are difficult to diagnose and typically involve histopathologic analysis of tissue biopsy specimens. Several serological and immunological diagnostic assays have, however, been developed. (U.S. Pat. No. 7,008,774; Senaldi et al., (1996) *J. Immunol. Methods* 193:9 5; Zijlstra, et al., (1997) *Trans. R. Soc. Trop. Med. Hyg.* 91:671 673; Badaro, et al., (1996) J. Inf. Dis. 173:758 761; Choudhary, S., et al., (1992) *J. Comm. Dis.* 24:32 36; Badaro, R., et al., (1986) *Am. J. Trop. Med. Hyg.* 35:72 78; Choudhary, A., et al., (1990) *Trans. R. Soc. Trop. Med. Hyg.* 84:363 366; and Reed, S. G., et al., (1990) *Am. J. Trop. Med. Hyg.* 43:632 639). The promastigotes release metabolic products into the culture medium to produce conditioned medium. These metabolic products are immunogenic to the host. See Schnur, L. F., et al., (1972) Isrl. J. Med. Sci. 8:932 942; Sergeiev, V. P., et al., (1969) Med. Parasitol. 38:208 212; El-On, J., et al., (1979) Exper. Parasitol. 47:254 269; and Bray, R. S., et al., (1966) Trans. R. Soc. Trop. Med. Hyg. 60:605 609; U.S. Pat. Nos. 6,846,648, 5,912,166; 5,719,263; 5,411,865).

About 40 million people around the world are infected with HIV, the virus that causes AIDS. Around 3 million people die of the disease each year, 95 percent of them in the developing world. Each year, close to 5 million people become infected with HIV. Currently, sub-Saharan African carries the highest burden of disease, but it is quickly spreading to other countries such as India, China, and Russia. The epidemic is growing most rapidly among minority populations. In the United States there have been more than 950,000 cases of AIDS reported since 1981. AIDS hits people during their most productive years. Women, for both biological and social reasons, have an increased risk for HIV/AIDS.

AIDS is caused by human immunodeficiency virus (HIV), which kills and damages cells of the body's immune system and progressively destroys the body's ability to fight infections and certain cancers. HIV is spread most commonly by having unprotected sex with an infected partner. The most robust solution to the problem is preventing the virus from spreading. Making a safe, effective, and affordable HIV vaccine is one way to reach this goal. Across the world, fewer than one in five people at high risk for HIV infection have access to effective prevention.

Methods for diagnosing HIV infections are known, including by virus culture, PCR of definitive nucleic acid sequences from patient specimens, and antibody tests for the presence of anti-HIV antibodies in patient sera, (see e.g., U.S. Pat. Nos. 6,979,535, 6,544,728, 6,316,183, 6,261,762, 4,743,540.)

According to certain other embodiments as disclosed herein, the vaccine compositions and related formulations and methods of use may include an antigen that is derived from a cancer cell, as may be useful for the immunotherapeutic treatment of cancers. For example, the adjuvant formulation may finds utility with tumor rejection antigens such as those for prostate, breast, colorectal, lung, pancreatic, renal or melanoma cancers. Exemplary cancer or cancer cell-derived antigens include MAGE 1, 3 and MAGE 4 or other MAGE antigens such as those disclosed in WO99/40188, PRAME, BAGE, Lage (also known as NY Eos 1) SAGE and HAGE (WO 99/53061) or GAGE (Robbins and Kawakami, 1996 *Current Opinions in Immunology* 8, pps 628-636; Van den Eynde et al., *International Journal of Clinical & Laboratory Research* (1997 & 1998); Correale et al. (1997), *Journal of the National Cancer Institute* 89, p. 293. These non-limiting examples of cancer antigens are expressed in a wide range of tumor types such as melanoma, lung carcinoma, sarcoma and bladder carcinoma. See, e.g., U.S. Pat. No. 6,544,518.

Other tumor-specific antigens are suitable for use with GLA according to certain presently disclosed embodiments include, but are not restricted to, tumor-specific or tumor-associated gangliosides such as $GM_2$, and $GM_3$ or conjugates thereof to carrier proteins; or an antigen for use in a GLA vaccine composition for eliciting or enhancing an anti-cancer immune response may be a self peptide hormone such as whole length Gonadotrophin hormone releasing hormone (GnRH, WO 95/20600), a short 10 amino acid long peptide, useful in the treatment of many cancers. In another embodiment prostate antigens are used, such as Prostate specific antigen (PSA), PAP, PSCA (e.g., *Proc. Nat. Acad. Sci. USA* 95(4) 1735-1740 1998), PSMA or, in a preferred embodiment an antigen known as Prostase. (e.g., Nelson, et al., *Proc. Natl. Acad. Sci. USA* (1999) 96: 3114-3119; Ferguson, et al. *Proc. Natl. Acad. Sci. USA* 1999. 96, 3114-3119; WO 98/12302; U.S. Pat. No. 5,955,306; WO 98/20117; U.S. Pat. Nos. 5,840,871 and 5,786,148; WO 00/04149. Other prostate specific antigens are known from WO 98/137418, and WO/004149. Another is STEAP (*PNAS* 96 14523 14528 7-12 1999).

Other tumor associated antigens useful in the context of the present invention include: Plu-1 (*J Biol. Chem* 274 (22) 15633-15645, 1999), HASH-1, HasH-2, Cripto (Salomon et al *Bioessays* 199, 21:61-70, U.S. Pat. No. 5,654,140) and Criptin (U.S. Pat. No. 5,981,215). Additionally, antigens particularly relevant for vaccines in the therapy of cancer also comprise tyrosinase and survivin.

The herein disclosed embodiments pertaining to GLA-containing vaccine compositions comprising a cancer antigen will be useful against any cancer characterised by tumor associated antigen expression, such as HER-2/neu expression or other cancer-specific or cancer-associated antigens.

Diagnosis of cancer in a subject having or suspected of being at risk for having cancer may be accomplished by any of a wide range of art-accepted methodologies, which may vary depending on a variety of factors including clinical presentation, degree of progression of the cancer, the type of cancer, and other factors. Examples of cancer diagnostics include histopathological, histocytochemical, immunohistocytochemical and immunohistopathological examination of patient samples (e.g., blood, skin biopsy, other tissue biopsy, surgical specimens, etc.), PCR tests for defined genetic (e.g., nucleic acid) markers, serological tests for circulating cancer-associated antigens or cells bearing such antigens, or for antibodies of defined specificity, or other methodologies with which those skilled in the art will be familiar. See, e.g., U.S. Pat. Nos. 6,734,172; 6,770,445; 6,893,820; 6,979,730; 7,060,802; 7,030,232; 6,933,123; 6,682,901; 6,587,792; 6,512,102; 7,078,180; 7,070,931; JP5-328975; Waslylyk et al., 1993 *Eur. J Bioch.* 211(7):18.

Vaccine compositions and methods according to certain embodiments of the present invention may also be used for the prophylaxis or therapy of autoimmune diseases, which include diseases, conditions or disorders wherein a host's or subject's immune system detrimentally mediates an immune response that is directed against "self" tissues, cells, biomolecules (e.g., peptides, polypeptides, proteins, glycoproteins, lipoproteins, proteolipids, lipids, glycolipids, nucleic acids such as RNA and DNA, oligosaccharides, polysaccharides, proteoglycans, glycosaminoglycans, or the like, and other molecular components of the subjects cells and tissues) or epitopes (e.g., specific immunologically defined recognition structures such as those recognized by an antibody variable region complementarity determining region (CDR) or by a T cell receptor CDR.

Autoimmune diseases are thus characterized by an abnormal immune response involving either cells or antibodies, that are in either case directed against normal autologous tissues. Autoimmune diseases in mammals can generally be classified in one of two different categories: cell-mediated disease (i.e., T-cell) or antibody-mediated disorders. Non-limiting examples of cell-mediated autoimmune diseases include multiple sclerosis, rheumatoid arthritis, Hashimoto thyroiditis, type I diabetes mellitus (Juvenile onset diabetes) and autoimmune uvoretinitis. Antibody-mediated autoimmune disorders include, but are not limited to, myasthenia gravis, systemic lupus erythematosus (or SLE), Graves' disease, autoimmune hemolytic anemia, autoimmune thrombocytopenia, autoimmune asthma, cryoglobulinemia, thrombic thrombocytopenic purpura, primary biliary sclerosis and pernicious anemia. The antigen(s) associated with: systemic lupus erythematosus is small nuclear ribonucleic acid proteins (snRNP); Graves' disease is the thyrotropin receptor, thyroglobulin and other components of thyroid epithelial cells (Akamizu et al., 1996; Kellerman et al., 1995; Raju et al., 1997; and Texier et al., 1992); pemphigus is cadherin-like pemphigus antigens such as desmoglein 3 and other adhesion molecules (Memar et al., 1996: Stanley, 1995; Plott et al., 1994; and Hashimoto, 1993); and thrombic thrombocytopenic purpura is antigens of platelets. (See, e.g., U.S. Pat. No. 6,929,796; Gorski et al. (Eds.), *Autoimmunity*, 2001, Kluwer Academic Publishers, Norwell, Mass.; Radbruch and Lipsky, P. E. (Eds.) *Current Concepts in Autoimmunity and Chronic Inflammation* (*Curr. Top. Microbiol. and Immunol.*) 2001, Springer, NY.)

Autoimmunity plays a role in more than 80 different diseases, including type 1 diabetes, multiple sclerosis, lupus, rheumatoid arthritis, scleroderma, and thyroid diseases. Vigorous quantitative estimates of morbidity for most autoimmune diseases are lacking. Most recent studies done in the late 1990s reveal that autoimmune diseases are the third most common major illness in the United States; and the most common autoimmune diseases affect more than 8.5 million Americans. Current estimates of the prevalence of the disease range from 5 to 8 percent of the United States population. Most autoimmune diseases disproportionately affect women. Women are 2.7 times more likely than men to acquire an autoimmune disease. Women are more susceptible to autoimmune diseases; men appear to have higher levels of natural killer cell activity than do women. (Jacobsen et al, *Clinical Immunology and Immunopathology*, 84:223-243, 1997.)

Autoimmune diseases occur when the immune system mistakes self tissues for nonself and mounts an inappropriate attack. The body can be affected in different ways from autoimmune diseases, including, for example, the gut (Crohn's disease) and the brain (multiple sclerosis). It is known that an autoantibody attacks self-cells or self-tissues to injure their function and as a result causes autoimmune diseases, and that the autoantibody may be detected in the patient's serum prior to the actual occurrence of an autoimmune disease (e.g., appearance of clinical signs and symptoms). Detection of an autoantibody thus permits early discovery or recognition of presence or risk for developing an autoimmune disease. Based on these findings, a variety of autoantibodies against autoantigens have been discovered and the autoantibodies against autoantigens have been measured in clinical tests (e.g., U.S. Pat. Nos. 6,919,210, 6,596, 501, 7,012,134, 6,919,078) while other autoimmune diagnostics may involve detection of a relevant metabolite (e.g., U.S. Pat. No. 4,659,659) or immunological reactivity (e.g., U.S. Pat. Nos. 4,614,722 and 5,147,785, 4,420,558, 5,298, 396, 5,162,990, 4,420,461, 4,595,654, 5,846,758, 6,660, 487).

In certain embodiments, the compositions of the invention will be particularly applicable in treatment of the elderly and/or the immunosuppressed, including subjects on kidney dialysis, subjects on chemo-therapy and/or radiation therapy, transplant recipients, and the like. Such individuals generally exhibit diminished immune responses to vaccines and therefore use of the compositions of the invention can enhance the immune responses achieved in these subjects.

In other embodiments, the antigen or antigens used in the compositions of the invention include antigens associated with respiratory diseases, such as those caused or exacerbated by bacterial infection (e.g. pneumococcal), for the prophylaxis and therapy of conditions such as chronic obstructive pulmonary disease (COPD). COPD is defined physiologically by the presence of irreversible or partially reversible airway obstruction in patients with chronic bronchitis and/or emphysema (Am J Respir Crit Care Med. 1995 November; 152(5 Pt 2):577-121). Exacerbations of COPD are often caused by bacterial (e.g. pneumococcal) infection (Clin Microbiol Rev. 2001 April; 14(2):336-63). In a particular embodiment, a composition of the invention comprises a GLA adjuvant, as described herein, in combination with the Pneumococcal vaccine Prevnar® (Wyeth).

In still other embodiments, the compositions of the invention, comprising GLA as described herein, are used in the treatment of allergic conditions. For example, in a particular embodiment, the compositions are used in allergy desensitization therapy. Such therapy involves the stimulation of the immune system with gradually increasing doses of the substances to which a person is allergic, wherein the substances are formulated in compositions comprising GLA. In specific embodiments, the compositions are used in the treatment of allergies to food products, pollen, mites, cats or stinging insects (e.g., bees, hornets, yellow jackets, wasps, velvet ants, fire ants).

TLR

As described herein, certain embodiments of the present invention contemplate vaccine compositions and immunological adjuvant compositions, including pharmaceutical compositions, that include one or more toll-like receptor agonist (TLR agonist). Toll-like receptors (TLR) include cell surface transmembrane receptors of the innate immune system that confer early-phase recognition capability to host cells for a variety of conserved microbial molecular structures such as may be present in or on a large number of infectious pathogens. (e.g., Armant et al., 2002 *Genome Biol.* 3(8): reviews 3011.1-3011.6; Fearon et al., 1996 *Science* 272:50; Medzhitov et al., 1997 *Curr. Opin. Immunol.* 9:4; Luster 2002 *Curr. Opin. Immunol.* 14:129; Lien et al. 2003 *Nat. Immunol.* 4:1162; Medzhitov, 2001 *Nat. Rev. Immunol.* 1:135; Takeda et al., 2003 *Ann Rev Immunol.* 21:335; Takeda et al. 2005 *Int. Immunol.* 17:1; Kaisho et al., 2004 *Microbes Infect.* 6:1388; Datta et al., 2003 *J. Immunol.* 170:4102).

Induction of TLR-mediated signal transduction to potentiate the initiation of immune responses via the innate immune system may be effected by TLR agonists, which engage cell surface TLR. For example, lipopolysaccharide (LPS) may be a TLR agonist through TLR2 or TLR4 (Tsan et al., 2004 *J. Leuk. Biol.* 76:514; Tsan et al., 2004 *Am. J. Physiol. Cell Phsiol.* 286:C739; Lin et al., 2005 *Shock* 24:206); poly(inosine-cytidine) (polyI:C) may be a TLR agonist through TLR3 (Salem et al., 2006 Vaccine 24:5119); CpG sequences (oligodeoxynucleotides containing unmethylated cytosine-guanosine or "CpG" dinucleotide motifs, e.g., CpG 7909, Cooper et al., 2005 AIDS 19:1473; CpG 10101 Bayes et al. *Methods Find Exp Clin Pharmacol* 27:193; Vollmer et al. *Expert Opinion on Biological Therapy* 5:673; Vollmer et al., 2004 *Antimicrob. Agents Chemother.* 48:2314; Deng et al., 2004 *J. Immunol.* 173:5148) may be TLR agonists through TLR9 (Andaloussi et al., 2006 *Glia* 54:526; Chen et al., 2006 *J. Immunol.* 177:2373); peptidoglycans may be TLR2 and/or TLR6 agonists (Soboll et al., 2006 *Biol. Reprod.* 75:131; Nakao et al., 2005 *J. Immunol.* 174:1566); 3M003 (4-amino-2-(ethoxymethyl)-α,α-dimethyl-6,7,8,9-tetrahydro-1H-imidazo[4,5-c]quinoline-1-ethanol hydrate, Mol. Wt. 318 Da from 3M Pharmaceuticals, St. Paul, Minn., which is also a source of the related compounds 3M001 and 3M002; Gorden et al., 2005 *J. Immunol.* 174:1259) may be a TLR7 agonist (Johansen 2005 *Clin. Exp. Allerg.* 35:1591) and/or a TLR8 agonist (Johansen 2005); flagellin may be a TLR5 agonist (Feuillet et al., 2006 *Proc. Nat. Acad. Sci. USA* 103:12487); and hepatitis C antigens may act as TLR agonists through TLR7 and/or TLR9 (Lee et al., 2006 *Proc. Nat. Acad. Sci. USA* 103:1828; Horsmans et al., 2005 Hepatol. 42:724). Other TLR agonists are known (e.g., Schirmbeck et al., 2003 *J. Immunol.* 171: 5198) and may be used according to certain of the presently described embodiments.

For example, and by way of background (see, e.g., U.S. Pat. No. 6,544,518) immunostimulatory oligonucleotides containing ummethylated CpG dinucleotides ("CpG") are known as being adjuvants when administered by both systemic and mucosal routes (WO 96/02555, EP 468520, Davis et al., *J. Immunol*, 1998. 160(2):870-876; McCluskie and Davis, *J. Immunol.*, 1998, 161(9):4463-6). CpG is an abbreviation for cytosine-guanosine dinucleotide motifs present in DNA. The central role of the CG motif in immunostimulation was elucidated by Krieg, Nature 374, p 546 1995.

Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in certain embodiments of the present invention. CpG when formulated into vaccines, may be administered in free solution together with free antigen (WO 96/02555; McCluskie and Davis, supra) or covalently conjugated to an antigen (PCT Publication No. WO 98/16247), or formulated with a carrier such as aluminium hydroxide (e.g., Davis et al. supra, Brazolot-Millan et al., *Proc. Natl. Acad. Sci., USA*, 1998, 95(26), 15553-8).

The preferred oligonucleotides for use in adjuvants or vaccines of the present invention preferably contain two or more dinucleotide CpG motifs separated by at least three, more preferably at least six or more nucleotides. The oligonucleotides of the present invention are typically deoxynucleotides. In a preferred embodiment the internucleotide in the oligonucleotide is phosphorodithioate, or more preferably a phosphorothioate bond, although phosphodiester and other internucleotide bonds are within the scope of the invention including oligonucleotides with mixed internucleotide linkages. Methods for producing phosphorothioate oligonucleotides or phosphorodithioate are described in U.S. Pat. Nos. 5,666,153, 5,278,302 and WO95/26204.

Examples of preferred oligonucleotides have sequences that are disclosed in the following publications; for certain herein disclosed embodiments the sequences preferably contain phosphorothioate modified internucleotide linkages:

CPG 7909: Cooper et al., "CPG 7909 adjuvant improves hepatitis B virus vaccine seroprotection in antiretroviral-treated HIV-infected adults." AIDS, 2005 Sep. 23; 19(14): 1473-9.

CpG 10101: Bayes et al., "Gateways to clinical trials." *Methods Find. Exp. Clin. Pharmacol.* 2005 April; 27(3): 193-219.

Vollmer J., "Progress in drug development of immunostimulatory CpG oligodeoxynucleotide ligands for TLR9." *Expert Opinion on Biological Therapy.* 2005 May; 5(5): 673-682.

Alternative CpG oligonucleotides may comprise variants of the preferred sequences described in the above-cited publications that differ in that they have inconsequential nucleotide sequence substitutions, insertions, deletions and/or additions thereto. The CpG oligonucleotides utilized in certain embodiments of the present invention may be synthesized by any method known in the art (e.g., EP 468520). Conveniently, such oligonucleotides may be synthesized utilising an automated synthesizer. The oligonucleotides are typically deoxynucleotides. In a preferred embodiment the internucleotide bond in the oligonucleotide is phosphorodithioate, or more preferably phosphorothioate bond, although phosphodiesters are also within the scope of the presently contemplated embodiments. Oligonucleotides comprising different internucleotide linkages are also contemplated, e.g., mixed phosphorothioate phophodiesters. Other internucleotide bonds which stabilize the oligonucleotide may also be used.

Co-Adjuvant

Certain embodiments as provided herein include vaccine compositions and immunological adjuvant compositions, including pharmaceutical compositions, that contain, in addition to GLA, at least one co-adjuvant, which refers to a component of such compositions that has adjuvant activity but that is other than GLA. A co-adjuvant having such adjuvant activity includes a composition that, when administered to a subject such as a human (e.g., a human patient), a non-human primate, a mammal or another higher eukaryotic organism having a recognized immune system, is capable of altering (i.e., increasing or decreasing in a statistically significant manner, and in certain preferred embodiments, enhancing or increasing) the potency and/or longevity of an immune response. (See, e.g., Powell and Newman, "Vaccine design—The Subunit and Adjuvant Approach", 1995, Plenum Press, New York) In certain embodiments disclosed herein GLA and a desired antigen, and optionally one or more co-adjuvants, may so alter, e.g., elicit or enhance, an immune response that is directed against the desired antigen which may be administered at the same time as GLA or may be separated in time and/or space (e.g., at a different anatomic site) in its administration, but certain invention embodiments are not intended to be so limited and thus also contemplate administration of GLA in a composition that does not include a specified antigen but which may also include one or more of a TLR agonist, a co-adjuvant, an imidazoquinline immune response modifier, and a double stem loop immune modifier (dSLIM).

Accordingly and as noted above, co-adjuvants include compositions other than GLA that have adjuvant effects, such as saponins and saponin mimetics, including QS21 and QS21 mimetics (see, e.g., U.S. Pat. No. 5,057,540; EP 0 362 279 B1; WO 95/17210), alum, plant alkaloids such as tomatine, detergents such as (but not limited to) saponin, polysorbate 80, Span 85 and stearyl tyrosine, one or more cytokines (e.g., GM-CSF, IL-2, IL-7, IL-12, TNF-alpha, IFN-gamma), an imidazoquinoline immune response modifier, and a double stem loop immune modifier (dSLIM, e.g., Weeratna et al., 2005 Vaccine 23:5263).

Detergents including saponins are taught in, e.g., U.S. Pat. No. 6,544,518; Lacaille-Dubois, M and Wagner H. (1996 *Phytomedicine* 2:363-386), U.S. Pat. No. 5,057,540, Kensil, *Crit Rev Ther Drug Carrier Syst,* 1996, 12 (1-2):1-55, and EP 0 362 279 B1. Particulate structures, termed Immune Stimulating Complexes (ISCOMS), comprising fractions of Quil A (saponin) are haemolytic and have been used in the manufacture of vaccines (Morein, B., EP 0 109 942 B1). These structures have been reported to have adjuvant activity (EP 0 109 942 B1; WO 96/11711). The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (1991. *J. Immunology* 146:431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711. Other saponins which have been used in systemic vaccination studies include those derived from other plant species such as *Gypsophila* and *Saponaria* (Bomford et al., *Vaccine,* 10(9):572-577, 1992).

Escin is another detergent related to the saponins for use in the adjuvant compositions of the embodiments herein disclosed. Escin is described in the Merck index (12$^{th}$ Ed.: entry 3737) as a mixture of saponin occurring in the seed of the horse chestnut tree, *Aesculus hippocastanum*. Its isolation is described by chromatography and purification (Fiedler, Arzneimittel-Forsch. 4, 213 (1953)), and by ion-exchange resins (Erbring et al., U.S. Pat. No. 3,238,190).

Fractions of escin (also known as aescin) have been purified and shown to be biologically active (Yoshikawa M, et al. (*Chem Pharm Bull* (Tokyo) 1996 August; 44(8): 1454-1464)). Digitonin is another detergent, also being described in the Merck index (12th Ed., entry 3204) as a saponin, being derived from the seeds of *Digitalis purpurea* and purified according to the procedure described by Gisvold et al., *J. Am. Pharm. Assoc.*, 1934, 23, 664; and Rubenstroth-Bauer, *Physiol. Chem.*, 1955, 301, 621.

Other co-adjuvants for use according to certain herein disclosed embodiments include a block co-polymer or biodegradable polymer, which refers to a class of polymeric compounds with which those in the relevant art will be familiar. Examples of a block co-polymer or biodegradable polymer that may be included in a GLA vaccine composition or a GLA immunological adjuvant include Pluronic® L121 (BASF Corp., Mount Olive, N.J.; see, e.g., Yeh et al., 1996 *Pharm. Res.* 13:1693; U.S. Pat. No. 5,565,209), CRL1005 (e.g., Triozzi et al., 1997 *Clin Canc. Res.* 3:2355), poly (lactic-co-glycolic acid) (PLGA), poly(lactic acid) (PLA), poly-(D,L-lactide-co-glycolide) (PLG), and polyI:C. (See, e.g., Powell and Newman, "Vaccine design—The Subunit and Adjuvant Approach", 1995, Plenum Press, New York).

Certain embodiments contemplate GLA vaccines and GLA immunological adjuvants that include an oil, which in some such embodiments may contribute co-adjuvant activity and in other such embodiments may additionally or alternatively provide a pharmaceutically acceptable carrier or excipient. Any number of suitable oils are known and may be selected for inclusion in vaccine compositions and immunological adjuvant compositions based on the present disclosure. Examples of such oils, by way of illustration and not limitation, include squalene, squalane, mineral oil, olive oil, cholesterol, and a mannide monooleate.

Immune response modifiers such as imidazoquinoline immune response modifiers are also known in the art and may also be included as co-adjuvants in certain presently disclosed embodiments. Certain preferred imidazoquinoline immune response modifiers include, by way of non-limiting example, resiquimod (R848), imiquimod and gardiquimod (Hemmi et al., 2002 *Nat. Immunol.* 3:196; Gibson et al., 2002 *Cell. Immunol.* 218:74; Gorden et al., 2005 *J. Immunol.* 174:1259); these and other imidazoquinoline immune response modifiers may, under appropriate conditions, also have TLR agonist activity as described herein. Other immune response modifiers are the nucleic acid-based double stem loop immune modifiers (dSLIM). Specific examples of dSLIM that are contemplated for use in certain of the presently disclosed embodiments can be found in Schmidt et al., 2006 Allergy 61:56; Weihrauch et al. 2005 *Clin Cancer Res.* 11(16):5993-6001; Modern Biopharmaceuticals, J. Knäblein (Editor). John Wiley & Sons, Dec. 6, 2005. (dSLIM discussed on pages 183 to ~200), and from Mologen AG (Berlin, FRG: [retrieved online on 8/18/06 at http://www.mologen.com/English/04.20-dSLIM.shtml].

As also noted above, one type of co-adjuvant for use with GLA as described herein may be the aluminum co-adjuvants, which are generally referred to as "alum." Alum co-adjuvants are based on the following: aluminum oxyhydroxide; aluminum hydroxyphoshoate; or various proprietary salts. Vaccines that use alum co-adjuvants may include vaccines for tetanus strains, HPV, hepatitis A, inactivated polio virus, and other antigens as described herein. Alum co-adjuvants are advantageous because they have a good safety record, augment antibody responses, stabilize antigens, and are relatively simple for large-scale production. (Edelman 2002 *Mol. Biotechnol.* 21:129-148; Edelman, R. 1980 *Rev. Infect. Dis.* 2:370-383.)

Other co-adjuvants that may be combined with GLA for effective immune stimulation include saponins and saponin mimetics, including QS21 and structurally related compounds conferring similar effects and referred to herein as QS21 mimetics. QS21 has been recognized as a preferred co-adjuvant. QS21 may comprise an HPLC purified non-toxic fraction derived from the bark of *Quillaja Saponaria Molina*. The production of QS21 is disclosed in U.S. Pat. No. 5,057,540. (See also U.S. Pat. Nos. 6,936,255, 7,029, 678 and 6,932,972.)

GLA may also in certain embodiments be combined with "immunostimulatory complexes" known as ISCOMS (e.g., U.S. Pat. Nos. 6,869,607, 6,846,489, 6,027,732, 4,981,684), including saponin-derived ISCOMATRIX®, which is commercially available, for example, from Iscotec (Stockholm, Sweden) and CSL Ltd. (Parkville, Victoria, Australia).

In still other embodiments, adjuvant/delivery systems may be used in combination with GLA which are lipid assemblies (liposomes and other formulations) comprising, for example, positively charged polycationic lipids. Illustratively, such systems may include a synthetic biocompatible polycationic sphingolipid (e.g., D-Erythro-N-palmitoyl sphingosyl-1-0 carbamoyl-spermine; also referred to as CCS; available from NasVax Ltd.) or may include cholesterol (C) in addition to the CCS lipid (referred to as CCS/C or Vaxisome®; available from NasVax Ltd.). The vaccine liposomal formulations may be formed, for example, by mixing a dry powder of CCS or CCS/C with vaccine proteins or polynucleotides (antigens), such as in aqueous suspension. Antigen-loaded liposomes can then be sprayed into the nose (i.n.) or injected intramuscularly (i.m.) or subcutaneously (s.c.), for example.

In further embodiments, a vesicular adjuvant/delivery system consisting of unilamellar or multilamellar vesicles, called niosomes, can be used in conjunction with GLA. In this case, an aqueous solution is generally enclosed in a highly ordered bilayer made up of non-ionic surfactant, with or without cholesterol and dicetyl phosphate, and exhibit a behaviour similar to liposomes in vivo. The bilayered vesicular structure is an assembly of hydrophobic tails of surfactant monomer, shielded away from the aqueous space located in the center and hydrophilic head group, in contact with the same. Addition of cholesterol results in an ordered liquid phase formation which gives the rigidity to the bilayer, and results in less leaky niosomes. Dicetyl phosphate is known to increase the size of vesicles, provide charge to the vesicles, and thus shows increase entrapment efficiency. Other charge-inducers are stearylamine and diacylglycerol, that also help in electrostatic stabilization of the vesicles.

Niosomes have unique advantages over liposomes. Nisomes are quite stable structures, even in the emulsified form. They require no special conditions such as low temperature or inert atmosphere for protection or storage, and are chemically stable. Relatively low cost of materials makes it suitable for industrial manufacture. A number of non-ionic surfactants have been used to prepare vesicles, e.g., polyglycerol alkyl ether, glucosyl dialkyl ethers, crown ethers, ester linked surfactants, polyoxyethylene alkyl ether, Brij, and various spans and tweens.

Similar to liposomes, there are 3 major types of niosomes—multilamellar vesicles (MLV, size >0.05 μm), small unilamellar vesicles (SUV, size—0.025-0.05 μm), and large unilamellar vesicles (LUV, size >0.10 μm). MLVs vesicles exhibit increased-trapped volume and equilibrium solute distribution, and generally require hand-shaking method. They show variations in lipid compositions. SUVs are commonly produced by sonication, and French Press procedures. Ultrasonic electrocapillary emulsification or solvent dilution techniques can also be used to prepare SUVs. The injections of lipids solubilized in an organic solvent into an aqueous buffer can result in spontaneous formation of LUV. Another method of preparation of LUV is reverse phase evaporation, or by detergent solubilization method.

Recombinant Expression Construct

According to certain herein disclosed embodiments, the GLA vaccine composition may contain at least one recombinant expression construct which comprises a promoter operably linked to a nucleic acid sequence encoding an antigen. In certain further embodiments the recombinant expression construct is present in a viral vector, such as an adenovirus, adeno-associated virus, herpesvirus, lentivirus, poxvirus or retrovirus vector. Compositions and methods for making and using such expression constructs and vectors are known in the art, for the expression of polypeptide antigens as provided herein, for example, according to Ausubel et al. (Eds.), Current Protocols in Molecular Biology, 2006 John Wiley & Sons, NY. Non-limiting examples of recombinant expression constructs generally can be found, for instance, in U.S. Pat. Nos. 6,844,192; 7,037,712; 7,052,904; 7,001,770; 6,106,824; 5,693,531; 6,613,892; 6,875,610; 7,067,310; 6,218,186; 6,783,981; 7,052,904; 6,783,981; 6,734,172; 6,713,068; 5,795,577 and 6,770,445 and elsewhere, with teachings that can be adapted to the expression of polypeptide antigens as provided herein, for use in certain presently disclosed embodiments.

Immune Response

The invention thus provides compositions for altering (i.e., increasing or decreasing in a statistically significant manner, for example, relative to an appropriate control as will be familiar to persons skilled in the art) immune responses in a host capable of mounting an immune response. As will be known to persons having ordinary skill in the art, an immune response may be any active alteration of the immune status of a host, which may include any alteration in the structure or function of one or more tissues, organs, cells or molecules that participate in maintenance and/or regulation of host immune status. Typically, immune responses may be detected by any of a variety of well known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); or any other criterion by which the presence of an immune response may be detected.

Immune responses may often be regarded, for instance, as discrimination between self and non-self structures by the cells and tissues of a host's immune system at the molecular and cellular levels, but the invention should not be so limited. For example, immune responses may also include immune system state changes that result from immune recognition of self molecules, cells or tissues, as may accompany any number of normal conditions such as typical regulation of immune system components, or as may be present in pathological conditions such as the inappropriate autoimmune responses observed in autoimmune and degenerative diseases. As another example, in addition to induction by up-regulation of particular immune system activities (such as antibody and/or cytokine production, or activation of cell mediated immunity) immune responses may also include suppression, attenuation or any other down-regulation of detectable immunity, which may be the consequence of the antigen selected, the route of antigen administration, specific tolerance induction or other factors.

Determination of the induction of an immune response by the vaccines of the present invention may be established by any of a number of well known immunological assays with which those having ordinary skill in the art will be readily familiar. Such assays include, but need not be limited to, to in vivo or in vitro determination of: soluble antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays are widely known and may be found, for example in Lefkovits (*Immunology Methods Manual: The Comprehensive Sourcebook of Techniques,* 1998; see also *Current Protocols in Immunology*; see also, e.g., Weir, *Handbook of Experimental Immunology,* 1986 Blackwell Scientific, Boston, Mass.; Mishell and Shigii (eds.) *Selected Methods in Cellular Immunology,* 1979 Freeman Publishing, San Francisco, Calif.; Green and Reed, 1998 *Science* 281: 1309 and references cited therein.).

Detection of the proliferation of antigen-reactive T cells may be accomplished by a variety of known techniques. For example, T cell proliferation can be detected by measuring the rate of DNA synthesis, and antigen specificity can be determined by controlling the stimuli (such as, for example, a specific desired antigen- or a control antigen-pulsed antigen presenting cells) to which candidate antigen-reactive T cells are exposed. T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, $Ca^{2+}$ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to a particular antigen may be quantified.

Detection of antigen-specific antibody production may be achieved, for example, by assaying a sample (e.g., an immunoglobulin containing sample such as serum, plasma or blood) from a host treated with a vaccine according to the present invention using in vitro methodologies such as radioimmunoassay (RIA), enzyme linked immunosorbent assays (ELISA), equilibrium dialysis or solid phase immunoblotting including Western blotting. In preferred embodiments ELISA assays may further include antigen-capture immobilization of the target antigen with a solid phase monoclonal antibody specific for the antigen, for example, to enhance the sensitivity of the assay. Elaboration of soluble mediators (e.g., cytokines, chemokines, lymphokines, prostaglandins, etc.) may also be readily determined by enzyme-linked immunosorbent assay (ELISA), for example, using methods, apparatus and reagents that are readily available from commercial sources (e.g., Sigma, St. Louis, Mo.; see also R & D Systems 2006 Catalog, R & D Systems, Minneapolis, Minn.).

Any number of other immunological parameters may be monitored using routine assays that are well known in the art. These may include, for example, antibody dependent cell-mediated cytotoxicity (ADCC) assays, secondary in vitro antibody responses, flow immunocytofluorimetric analysis of various peripheral blood or lymphoid mononuclear cell subpopulations using well established marker antigen systems, immunohistochemistry or other relevant assays. These and other assays may be found, for example, in Rose et al. (Eds.), *Manual of Clinical Laboratory Immunology*, 5$^{th}$ Ed., 1997 American Society of Microbiology, Washington, D.C.

Accordingly it is contemplated that the vaccine and adjuvant compositions provided herein will be capable of eliciting or enhancing in a host at least one immune response that is selected from a $T_H1$-type T lymphocyte response, a $T_H2$-type T lymphocyte response, a cytotoxic T lymphocyte (CTL) response, an antibody response, a cytokine response, a lymphokine response, a chemokine response, and an inflammatory response. In certain embodiments the immune response may comprise at least one of production of one or a plurality of cytokines wherein the cytokine is selected from interferon-gamma (IFN-γ), tumor necrosis factor-alpha (TNF-α), production of one or a plurality of interleukins wherein the interleukin is selected from IL-1, IL-2, IL-3, IL-4, IL-6, IL-8, IL-10, IL-12, IL-13, IL-16, IL-18 and IL-23, production one or a plurality of chemokines wherein the chemokine is selected from MIP-1α, MIP-1β, RANTES, CCL4 and CCL5, and a lymphocyte response that is selected from a memory T cell response, a memory B cell response, an effector T cell response, a cytotoxic T cell response and an effector B cell response. See, e.g., WO 94/00153; WO 95/17209; WO 96/02555; U.S. Pat. Nos. 6,692,752; 7,084,256; 6,977,073; 6,749,856; 6,733,763; 6,797,276; 6,752,995; 6,057,427; 6,472,515; 6,309,847; 6,969,704; 6,120,769; 5,993,800; 5,595,888; Smith et al., 1987 J Biol Chem. 262:6951; Kriegler et al., 1988 Cell 53:45 53; Beutler et al., 1986 Nature 320:584; U.S. Pat. Nos. 6,991,791; 6,654,462; 6,375,944.

Pharmaceutical Compositions

Pharmaceutical compositions generally comprise GLA (available from Avanti Polar Lipids, Inc., Alabaster, Ala.; product number 699800) and may further comprise one or more components as provided herein that are selected from antigen, TLR agonist, co-adjuvant (including optionally a cytokine, an imidazoquinoline immune response modifier and/or a dSLIM), and/or a recombinant expression construct, in combination with a pharmaceutically acceptable carrier, excipient or diluent.

Therefore, in certain aspects, the present invention is drawn to GLA "monotherapy" wherein GLA, as described herein, is formulated in a composition that is substantially devoid of other antigens, and is administered to a subject in order to stimulate an immune response, e.g., a non-specific immune response, for the purpose of treating or preventing a disease or other condition, such as for treating an infection by an organism, for treating seasonal rhinitis, or the like. In one embodiment, for example, the compositions and methods of the invention employ a monophosphorylated disaccharide for stimulating an immune response in a subject. In another particular embodiment, the compositions and methods employ a 2-monoacyl form of Lipid A for stimulating an immune response in a subject. In another particular embodiment, the GLA is in the form of a spray, optionally provided in a kit.

The GLA may be preferably formulated in a stable emulsion. In one particular embodiment, for example, a composition is provided comprising a lipid A derivative in a stable emulsion substantially devoid of other antigens. In another particular embodiment, a composition is provided comprising a derivative of 3-acylated monophosphorylated lipid A, suitable for use in mammals, wherein the 2 amine position has a single acyl chain, and that is substantially devoid of other antigens.

In certain other embodiments, the pharmaceutical composition is a vaccine composition that comprises both GLA and an antigen and may further comprise one or more components, as provided herein, that are selected from TLR agonist, co-adjuvant (including, e.g., a cytokine, an imidazoquinoline immune response modifier and/or a dSLIM) and the like and/or a recombinant expression construct, in combination with a pharmaceutically acceptable carrier, excipient or diluent.

Illustrative carriers will be nontoxic to recipients at the dosages and concentrations employed. For GLA-plus-nucleic acid-based vaccines, or for vaccines comprising GLA plus an antigen, about 0.01 µg/kg to about 100 mg/kg body weight will be administered, typically by the intradermal, subcutaneous, intramuscular or intravenous route, or by other routes.

A preferred dosage is about 1 µg/kg to about 1 mg/kg, with about 5 µg/kg to about 200 µg/kg particularly preferred. It will be evident to those skilled in the art that the number and frequency of administration will be dependent upon the response of the host. "Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id. "Pharmaceutically acceptable salt" refers to salts of the compounds of the present invention derived from the combination of such compounds and an organic or inorganic acid (acid addition salts) or an organic or inorganic base (base addition salts). The compositions of the present invention may be used in either the free base or salt forms, with both forms being considered as being within the scope of the present invention.

The pharmaceutical compositions may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal (e.g., as a spray). The term parenteral as used herein includes iontophoretic (e.g., U.S. Pat. Nos. 7,033,598; 7,018,345; 6,970,739), sonophoretic (e.g., U.S. Pat. Nos. 4,780,212; 4,767,402; 4,948,587; 5,618,275; 5,656, 016; 5,722,397; 6,322,532; 6,018,678), thermal (e.g., U.S. Pat. Nos. 5,885,211; 6,685,699), passive transdermal (e.g., U.S. Pat. Nos. 3,598,122; 3,598,123; 4,286,592; 4,314,557; 4,379,454; 4,568,343; 5,464,387; UK Pat. Spec. No. 2232892; U.S. 6,871,477; 6,974,588; 6,676,961), microneedle (e.g., U.S. Pat. Nos. 6,908,453; 5,457,041; 5,591,139; 6,033,928) administration and also subcutaneous injections, intravenous, intramuscular, intrasternal, intracavernous, intrathecal, intrameatal, intraurethral injection or infusion techniques. In a particular embodiment, a composition as described herein (including vaccine and pharmaceutical compositions) is administered intradermally by a technique selected from iontophoresis, microcavitation, sonophoresis or microneedles.

The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, preferred compositions contain one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following carriers or excipients: sterile diluents such as water for injection, saline solution, preferably physiological saline, Ringer's solution, isotonic sodium chloride, fixed oils such as squalene, squalane, mineral oil, a mannide monooleate, cholesterol, and/or synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In a particular embodiment, a pharmaceutical or vaccine composition of the invention comprises a stable aqueous suspension of less than 0.2 um and further comprises at least one component selected from the group consisting of phospholipids, fatty acids, surfactants, detergents, saponins, fluorodated lipids, and the like.

In another embodiment, a composition of the invention is formulated in a manner which can be aerosolized.

It may also be desirable to include other components in a vaccine or pharmaceutical composition, such as delivery vehicles including but not limited to aluminum salts, water-in-oil emulsions, biodegradable oil vehicles, oil-in-water emulsions, biodegradable microcapsules, and liposomes. Examples of additional immunostimulatory substances (co-adjuvants) for use in such vehicles are also described above and may include N-acetylmuramyl-L-alanine-D-isoglutamine (MDP), glucan, IL-12, GM-CSF, gamma interferon and IL-12.

While any suitable carrier known to those of ordinary skill in the art may be employed in the pharmaceutical compositions of this invention, the type of carrier will vary depending on the mode of administration and whether a sustained release is desired. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109. In this regard, it is preferable that the microsphere be larger than approximately 25 microns.

Pharmaceutical compositions (including GLA vaccines and GLA immunological adjuvants) may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. Preferably, product may be formulated as a lyophilizate using appropriate excipient solutions (e.g., sucrose) as diluents.

As described above, in certain embodiments the subject invention includes compositions capable of delivering nucleic acid molecules encoding desired antigens. Such compositions include recombinant viral vectors (e.g., retroviruses (see WO 90/07936, WO 91/02805, WO 93/25234, WO 93/25698, and WO 94/03622), adenovirus (see Berkner, *Biotechniques* 6:616-627, 1988; Li et al., *Hum. Gene Ther.* 4:403-409, 1993; Vincent et al., *Nat. Genet.* 5:130-134, 1993; and Kolls et al., *Proc. Natl. Acad. Sci. USA* 91:215-219, 1994), pox virus (see U.S. Pat. Nos. 4,769,330; 5,017,487; and WO 89/01973)), recombinant expression construct nucleic acid molecules complexed to a polycationic molecule (see WO 93/03709), and nucleic acids associated with liposomes (see Wang et al., *Proc. Natl. Acad. Sci. USA* 84:7851, 1987). In certain embodiments, the DNA may be linked to killed or inactivated adenovirus (see Curie) et al., *Hum. Gene Ther.* 3:147-154, 1992; Cotton et al., *Proc. Natl. Acad. Sci. USA* 89:6094, 1992). Other suitable compositions include DNA-ligand (see Wu et al., *J. Biol. Chem.* 264: 16985-16987, 1989) and lipid-DNA combinations (see Feigner et al., *Proc. Natl. Acad. Sci. USA* 84:7413-7417, 1989).

In addition to direct in vivo procedures, ex vivo procedures may be used in which cells are removed from a host, modified, and placed into the same or another host animal. It will be evident that one can utilize any of the compositions noted above for introduction of antigen-encoding nucleic acid molecules into tissue cells in an ex vivo context. Protocols for viral, physical and chemical methods of uptake are well known in the art.

Accordingly, the present invention is useful for enhancing or eliciting, in a host, a patient or in cell culture, an immune response. As used herein, the term "patient" refers to any warm-blooded animal, preferably a human. A patient may be afflicted with an infectious disease, cancer, such as breast cancer, or an autoimmune disease, or may be normal (i.e., free of detectable disease and/or infection). A "cell culture" is any preparation containing immunocompetent cells or isolated cells of the immune system (including, but not limited to, T cells, macrophages, monocytes, B cells and dendritic cells). Such cells may be isolated by any of a variety of techniques well known to those of ordinary skill in the art (e.g., Ficoll-hypaque density centrifugation). The cells may (but need not) have been isolated from a patient afflicted with cancer, and may be reintroduced into a patient after treatment.

In certain embodiments a liquid composition intended for either parenteral or oral administration should contain an amount of GLA vaccine composition such that a suitable dosage will be obtained. Typically, this amount is at least 0.01 wt % of an antigen in the composition. When intended for oral administration, this amount may be varied to be between 0.1 and about 70% of the weight of the composition. Preferred oral compositions contain between about 4% and about 50% of the antigen. Preferred compositions and preparations are prepared so that a parenteral dosage unit contains between 0.01 to 1% by weight of active composition.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the antigen (e.g., GLA-antigen vaccine composition) or GLA (e.g., immunological adjuvant composition; GLA is available from Avanti Polar Lipids, Inc., Alabaster, Ala.; e.g., product number 699800) of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. In the methods of the invention, the vaccine compositions/adjuvants may be administered through use of insert(s), bead(s), timed-release formulation(s), patch(es) or fast-release formulation(s).

Also contemplated in certain embodiments are kits comprising the herein described GLA vaccine compositions and/or GLA immunological adjuvant compositions, which may be provided in one or more containers. In one embodiment all components of the GLA vaccine compositions and/or GLA immunological adjuvant compositions are present together in a single container, but the invention embodiments are not intended to be so limited and also contemplate two or more containers in which, for example, a GLA immunological adjuvant composition is separate from, and not in contact with, the antigen component. By way of non-limiting theory, it is believed that in some cases administration only of the GLA immunological adjuvant composition may be performed beneficially, whilst in other cases such administration may beneficially be separated temporally and/or spatially (e.g., at a different anatomical site) from administration of the antigen, whilst in still other cases administration to the subject is beneficially conducted of a GLA vaccine composition as described herein and containing both antigen and GLA, and optionally other herein described components as well.

A container according to such kit embodiments may be any suitable container, vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Typically such a container may be made of a material that is compatible with the intended use and from which recovery of the contained contents can be readily achieved. Preferred examples of such containers include glass and/or plastic sealed or re-sealable tubes and ampules, including those having a rubber septum or other sealing means that is compatible with withdrawal of the contents using a needle and syringe. Such containers may, for instance, by made of glass or a chemically compatible plastic or resin, which may be made of, or may be coated with, a material that permits efficient recovery of material from the container and/or protects the material from, e.g., degradative conditions such as ultraviolet light or temperature extremes, or from the introduction of unwanted contaminants including microbial contaminants. The containers are preferably sterile or sterilizable, and made of materials that will be compatible with any carrier, excipient, solvent, vehicle or the like, such as may be used to suspend or dissolve the herein described vaccine compositions and/or immunological adjuvant compositions and/or antigens and/or recombinant expression constructs, etc.

Emulsion systems may also be used in formulating compositions of the present invention. For example, many single or multiphase emulsion systems have been described. Oil in water emulsion adjuvants per se have been suggested to be useful as adjuvant composition (EP 0 399 843B), also combinations of oil in water emulsions and other active agents have been described as adjuvants for vaccines (WO 95/17210; WO 98/56414; WO 99/12565; WO 99/11241). Other oil emulsion adjuvants have been described, such as water in oil emulsions (U.S. Pat. No. 5,422,109; EP 0 480 982 B2) and water in oil in water emulsions (U.S. Pat. No. 5,424,067; EP 0 480 981 B). The oil emulsion adjuvants for use in the present invention may be natural or synthetic, and may be mineral or organic. Examples of mineral and organic oils will be readily apparent to the man skilled in the art.

In a particular embodiment, a composition of the invention comprises an emulsion of oil in water wherein the GLA is incorporated in the oil phase. In another embodiment, a composition of the invention comprises an emulsion of oil in water wherein the GLA is incorporated in the oil phase and wherein an additional component is present, such as a co-adjuvant, TLR agonist, or the like, as described herein.

In order for any oil in water composition to be suitable for human administration, the oil phase of the emulsion system preferably comprises a metabolizable oil. The meaning of the term metabolizable oil is well known in the art. Metabolizable can be defined as "being capable of being transformed by metabolism" (Dorland's illustrated Medical Dictionary, W. B. Saunders Company, 25th edition (1974)). The oil may be any vegetable oil, fish oil, animal oil or synthetic oil, which is not toxic to the recipient and is capable of being transformed by metabolism. Nuts (such as peanut oil), seeds, and grains are common sources of vegetable oils. Synthetic oils are also part of this invention and can include commercially available oils such as NEOBEE® and others.

Squalene (2,6,10,15,19,23-Hexamethyl-2,6,10,14,18,22-tetracosahexaene), for example, is an unsaturated oil which is found in large quantities in shark-liver oil, and in lower quantities in olive oil, wheat germ nil, rice bran oil, and yeast, and is a particularly preferred oil for use in this invention. Squalene is a metabolizable oil virtue of the fact that it is an intermediate in the biosynthesis of cholesterol (Merck index, 10th Edition, entry no. 8619). Particularly preferred oil emulsions are oil in water emulsions, and in particular squalene in water emulsions. In addition, the most preferred oil emulsion adjuvants of the present invention comprise an antioxidant, which is preferably the oil .alpha.-tocopherol (vitamin E, EP 0 382 271 B1). WO 95/17210 and WO 99/11241 disclose emulsion adjuvants based on squalene, alpha-tocopherol, and TWEEN® 80, optionally formulated with the immunostimulants QS21 and/or 3D-MPL (which are discussed above). WO 99/12565 discloses an improvement to these squalene emulsions with the addition of a sterol into the oil phase. Additionally, a triglyceride, such as tricaprylin ($C_{27}H_{50}O_6$), may be added to the oil phase in order to stabilize the emulsion (WO 98/56414).

The size of the oil droplets found within the stable oil in water emulsion are preferably less than 1 micron, may be in the range of substantially 30-600 nm, preferably substantially around 30-500 nm in diameter, and most preferably substantially 150-500 nm in diameter, and in particular about 150 nm in diameter as measured by photon correlation spectroscopy. In this regard, 80% of the oil droplets by number should be within the preferred ranges, more preferably more than 90% and most preferably more than 95% of the oil droplets by number are within the defined size ranges. The amounts of the components present in the oil emulsions of the present invention are conventionally in the range of from 2 to 10% oil, such as squalene; and when present, from 2 to 10% alpha tocopherol; and from 0.3 to 3% surfactant, such as polyoxyethylene sorbitan monooleate. Preferably the ratio of oil:alpha tocopherol is equal or less than 1 as this provides a more stable emulsion. Span 85 may also be present at a level of about 1%. In some cases it may be advantageous that the vaccines of the present invention will further contain a stabiliser.

The method of producing oil in water emulsions is well known to the person skilled in the art. Commonly, the method comprises the mixing the oil phase with a surfactant such as a PBS/TWEEN80® solution, followed by homogenization using a homogenizer. For instance, a method that comprises passing the mixture once, twice or more times through a syringe needle would be suitable for homogenizing small volumes of liquid. Equally, the emulsification process in a microfluidiser (M110S microfluidics machine, maximum of 50 passes, for a period of 2 minutes at maximum pressure input of 6 bar (output pressure of about 850 bar)) could be adapted to produce smaller or larger volumes of emulsion. This adaptation could be achieved by routine experimentation comprising the measurement of the resultant emulsion until a preparation was achieved with oil droplets of the required diameter.

The following Examples are offered by way of illustration and not by way of limitation.

EXAMPLES

Example 1

GLA Aqueous Formulation

This example describes the preparation of a GLA-containing adjuvant aqueous formulation. The aqueous formulation of GLA (GLA-AF) contains Water For Injection (WFI), GLA (Avanti Polar Lipids, Inc., Alabaster, Ala.; product number 699800), and 1-palmitoyl-2-oleoyl-sn-glycero-3-phosphocholine (POPC). The formulation was prepared by adding a solution of ethanol and POPC to a pre-weighed amount of GLA. This wetted GLA was sonicated for 10 minutes to disperse the GLA as much as possible. The GLA was then dried under nitrogen gas. The dried GLA and POPC were reconstituted with WFI to the correct volume. This solution was sonicated at 60° C. for 15-30 minutes until all the GLA and POPC were in solution. For long term storage, GLA-AF formulations must be lyophilized. The lyophilization process consisted of adding glycerol to the solution until it was 2% of the total volume. Then the solution was placed in vials in 1-10 mL amounts. The vials were then run through the lyophilization process which consisted of freezing the solution and then putting it under vacuum to draw off the frozen water by sublimation.

Example 2

GLA HPLC Analysis

This example describes HPLC analysis of a GLA-containing adjuvant aqueous formulation. After the formulation was manufactured (see Example 1 above), certain release and stability tests were conducted to ensure product quality and reproducibility. All formulations were tested for release and long-term stability using High Performance Liquid Chromatography (HPLC), Dynamic Light Scattering (DLS) and a visual examination. HPLC chromatograms were collected using an Agilent 1100 system and an ESA Corona CAD detector. The method was run using a methanol to chloroform gradient on a Waters Atlantis C18 column. The injections included 2.5 µg of GLA (Avanti Polar Lipids, Inc., Alabaster, Ala.; product number 699800, GLA-AF) or MPL® (GSK Biologicals, Rixensart, Belgium, MPL-AF) respectively, and 0.27 µg of synthetic phosphocholine (POPC) which was used as a solubilizing agent.

FIG. 1 shows HPLC data demonstrating the number and amounts of contaminating materials in MPL-AF and GLA-AF.

The HPLC profiles showed that GLA-AF was substantially purer than MPL-AF. That is, there were fewer contaminant peaks in the GLA-AF than in the MPL-AF adjuvant formulation. A purer starting product is of tremendous benefit to researchers as the biological response obtained is from the single major component used in the formulations of the GLA.

Example 3

GLA Oil Formulation

This example describes preparation of one milliliter of a GLA-containing adjuvant oil formulation. GLA (100 micrograms; Avanti Polar Lipids, Inc., Alabaster, Ala.; product number 699800) was emulsified in squalene (34.3 mg) with glycerol (22.7 mg), phosphotidylcholine or lecithin (7.64 mg), Pluronic® F-68 (BASF Corp., Mount Olive, N.J.) or similar block co-polymer (0.364 mg) in 25 millimolar ammonium phosphate buffer (pH=5.1) using 0.5 mg D,L-alpha-tocopherol as an antioxidant. The mixture was processed under high pressure until an emulsion formed that did not separate and that had an average particle size of less than 180 nm. The emulsion was then sterile-filtered into glass unidose vials and capped for longer term storage. This preparation may be used for at least three years when stored at 2-8° C.

Example 4

GLA Stimulation of Murine Macrophages and Dendritic Cells

This example describes an in vitro model demonstrating an adjuvant effect of GLA. Standard tissue culture methodologies and reagents were employed. Cells of the murine J774 and RAW267.4 macrophage cell line (American Type Culture Collection, Manassas, Va.) were maintained according to the supplier's recommendations and cultured as adherent cell monolayers in multiwell dishes. Dendritic cells were derived from bone marrow progenitor cells following a protocol by Xiong et al. (J. Biol. Chem 2004, 279, pp 10776-83). Various adjuvant concentrations of synthetic GLA (Avanti Polar Lipids, Inc., Alabaster, Ala.; product number 699800) were achieved by diluting an aqueous adjuvant preparation in cell culture medium (DMEM containing 10% fetal bovine serum), and cells were maintained for 24 hours at 37° C. in a humidified atmosphere containing 5% $CO_2$, prior to collection of cell-free culture supernatants. Supernatant fluids were assayed for soluble murine cytokines such as IL-12, IL-6, and TNF, and chemokines such as RANTES, using specific sandwich ELISA assay kits (eBiosciences, San Diego, Calif. for cytokines, and R&D Systems, Minneapolis, Minn. for chemokines) according to the manufacturer's instructions.

GLA-AF induced dose-dependent immune responses in mouse macrophage cell lines and primary murine DC, characterized by the secretion of cytokines such as IL-12p40, IL-6, and TNF, and chemokines like RANTES.

Example 5

GLA Stimulation of Human Macrophages and Dendritic Cells

This example describes an in vitro model demonstrating the adjuvant effects of GLA. Standard tissue culture methodologies and reagents were employed.

Cells of the human Mono Mac 6 macrophage cell line (American Type Culture Collection, Manassas, Va.) were maintained according to the supplier's recommendations and cultured as adherent cell monolayers in multiwell plates. Dendritic cells were derived from peripheral blood mononuclear cells (PBMC) following a standard protocol. Various adjuvant concentrations of either synthetic GLA (Avanti Polar Lipids, Inc., Alabaster, Ala.; product number 699800) or the natural product MPL® (GSK Biologicals, Rixensart, Belgium) were achieved by diluting an aqueous adjuvant preparation in cell culture medium (DMEM containing 10% fetal bovine serum, for MonoMac 6, or 10% human serum, for DC), and cells were maintained for 24 hours at 37° C. in a humidified atmosphere containing 5% $CO_2$, prior to collection of cell-free culture supernatants. Supernatant fluids were assayed for soluble human cytokines such as IL-1β, IL-23, and IL-6, and chemokines such as IP-10, RANTES and MIP-1β using specific sandwich ELISA assay kits (eBiosciences, San Diego, Calif. for cytokines, and Invitrogen, Carlsbad, Calif., for chemokines) according to the manufacturer's instructions.

FIG. 2 shows ELISA data demonstrating levels of cytokines and chemokines expressed by human macrophages of the Mono Mac 6 cell line (panels a-e), and monocyte-derived DC (panels f-h) in response to GLA stimulation.

GLA-AF induced a dose-dependent immune response in the human macrophage cell line Mono Mac 6 (FIG. 2, panels a-e), and primary DC (FIG. 2, panels f-h), characterized by the secretion of cytokines such as IL-1β, IL-6, IL-23, and chemokines such as RANTES, IP-10, MIP-1β. GLA-AF was active at concentrations 5-500 lower compared to MPL-AF for all the cytokines and chemokines that were tested.

Example 6

GLA Stimulation of Human Blood Cells

This example describes an in vitro model demonstrating adjuvant effects of GLA. Standard tissue culture methodologies and reagents were employed.

Human whole blood cells were cultured with various adjuvant concentrations of either synthetic GLA (Avanti Polar Lipids, Inc., Alabaster, Ala.; product number 699800) or the natural product MPL® (GSK Biologicals, Rixensart, Belgium), achieved by diluting an aqueous adjuvant preparation in cell culture medium (DMEM containing 10% fetal bovine serum). Blood cells were maintained for 16 hours at 37° C. in a humidified atmosphere containing 5% $CO_2$, prior to collection of cell-free culture supernatants. Supernatant fluids were assayed for soluble human cytokine IL-1β using specific sandwich ELISA assay kit (eBiosciences, San Diego, Calif.) according to the manufacturer's instructions.

GLA-AF induced a dose-dependent immune response in human whole blood cells, characterized by the secretion of IL-1β☐ cytokine. In this assay, 92 nM of GLA was equivalent in potency to 57,000 nM of MPL-AF.

Example 7

Use of GLA-Containing Vaccine In Vivo

This example describes an in vivo model demonstrating an adjuvant effect of GLA in a vaccine against Influenza. Standard immunological methodologies and reagents were employed (Current Protocols in Immunology, Coligan et al. (Eds.) 2006 John Wiley & Sons, NY).

Mice (three Balb/c animals per group) were immunized twice at three-week intervals with the Fluzone vaccine (Sanofi-Aventis, Swiftwater, Pa., at 1/25 (20 µl) and 1/250 (2 µl) of the human dosage, alone, or formulated in (i) an aqueous emulsion containing GLA (Avanti Polar Lipids, Inc., Alabaster, Ala.; product number 699800; 20 µg per animal for each immunization) according to the procedure used in Example 1 above ("GLA-AF"), or (ii) a stable emulsion containing GLA (Avanti Polar Lipids, Inc., Alabaster, Ala.; product number 699800; 20 µg per animal for each immunization) according to the procedure used in Example 3 above ("GLA-SE"). Sera were collected by bleeding animals one week after each immunization, and serum levels of total IgG antibodies specific for Fluzone were examined by ELISA according to published methods (Id.). Serum levels of virus neutralizing antibodies were also examined by Hemagglutination Inhibition Assay (HAI) according to published methods.

FIG. 3 shows ELISA data demonstrating levels of anti-Fluzone antibody production induced in mice one week after each immunization (i.e., at day 7, panel A; and at day 28, panel B) using two different doses of Fluzone vaccine formulated with GLA-AF, or GLA-SE, compared to Fluzone alone. Means and SEM of reciprocal endpoint titers in each group/time point are shown. FIG. 3, panel C shows HAI data demonstrating levels of virus neutralizing antibody production induced in mice one week after the second immunization using two different doses of Fluzone vaccine formulated with GLA-AF, or GLA-SE, compared to Fluzone alone. Means and SEM of reciprocal endpoint titers in each group/time point are shown.

Total IgG and neutralizing antibody titers in response to Fluzone vaccination were enhanced by adding GLA, either in an aqueous or stable oil formulation. The adjuvanting effect of GLA was more pronounced with the 2 µl dose of Fluzone vaccine, and induced antigen-specific humoral responses similar to (GLA-AF) or greater than (GLA-SE) 20 µl of Fluzone vaccine alone. These results suggest that it is possible to reduce the dose of Fluzone vaccine by adjuvanting it with GLA-containing formulations, and still induce high levels of IgG and neutralizing antibody titers. This is of particular importance in the context of a world pandemic infection such as Bird Flu.

Example 8

Use of GLA-Containing Vaccine In Vivo

This example describes an in vivo model demonstrating an adjuvant effect of GLA in a vaccine containing a specific *Leishmania* antigen. Standard immunological methodologies and reagents were employed (Current Protocols in Immunology, Coligan et al. (Eds.) 2006 John Wiley & Sons, NY).

Mice (three C57BL/6 animals per group) were immunized three times at three-week intervals with the SMT antigen (10 µg per animal for each immunization) used alone or formulated in a stable emulsion containing GLA (Avanti Polar Lipids, Inc., Alabaster, Ala.; product number 699800; 20 µg per animal for each immunization) according to the procedure used in Example 3 above, GLA-SE). Sera were collected by bleeding animals one week after the third immunization, and serum levels of IgG1 and IgG2c antibodies specific for SMT antigen were examined by ELISA according to published methods.

FIG. 4 shows ELISA data demonstrating levels of anti-SMT antibody production induced in mice one week after the third immunization using SMT antigen alone, or formulated with GLA-SE. Means and SEM of reciprocal endpoint titers in each group are shown.

Predominance of either IgG1 or IgG2c antibody isotype is associated with TH2 or TH1 responses respectively. It has been demonstrated that a TH1 response is necessary for protection against *Leishmania* infection. SMT alone vaccination induced predominantly SMT-specific IgG1 antibody. SMT+GLA-SE vaccination induced higher antibody titers, and reverted the phenotype to a predominantly IgG2c antigen-specific antibody response, associated with protection against the disease.

Example 9

Use of GLA-Containing Vaccine In Vivo

This example describes an in vivo model demonstrating an adjuvant effect of GLA in a vaccine containing a specific *Leishmania* antigen. Standard immunological methodologies and reagents were employed (*Current Protocols in Immunology*, Coligan et al. (Eds.) 2006 John Wiley & Sons, NY).

Mice (three Balb/c animals per group) were immunized three times at two-week intervals with the Leish-110f antigen (10 µg per animal for each immunization) formulated in a stable emulsion containing different amounts of GLA (Avanti Polar Lipids, Inc., Alabaster, Ala.; product number 699800; 40, 20, 5, or 1 µg per animal for each immunization according to the procedure used in Example 3 above, GLA-SE). Sera were collected by bleeding animals one week after the first immunization, and serum levels of IgG1 and IgG2a antibodies specific for Leish-110f were examined by ELISA according to published methods (Id.).

FIG. 5 shows ELISA data demonstrating levels of anti-Leish-110f antibody production induced in mice one week after the first immunization using Leish-110f antigen formulated with different amounts of GLA (40, 20, 5, or 1 µg), compared to saline controls. Means and SEM of reciprocal endpoint titers in each group are shown.

Leish-110f-specific IgG1 and IgG2a antibody titers were GLA dose-dependent. Predominance of TH1 associated IgG2a antibody was observed at all concentrations of GLA tested.

Example 10

Use of GLA-Containing Vaccine In Vivo

This example describes an in vivo model demonstrating an adjuvant effect of GLA in a vaccine containing a specific *Leishmania* antigen. Standard immunological methodologies and reagents were employed (Current Protocols in Immunology, Coligan et al. (Eds.) 2006 John Wiley & Sons, NY).

Mice (three Balb/c animals per group) were immunized three times at three-week intervals with saline or the Leish-111f antigen (10 µg per animal for each immunization) formulated in a stable emulsion containing GLA (Avanti Polar Lipids, Inc., Alabaster, Ala.; product number 699800; 20 µg per animal for each immunization, according to the procedure used in Example 3 above, GLA-SE). Two weeks after the last injection, mice were sacrificed and spleen collected to analyze T cell-dependent IFN-γ and IL-4 cytokine responses to in vitro antigen stimulation by ELISA according to published methods.

Predominance of either IL-4 or IFN-γ cytokine is associated with TH2 or TH1 responses respectively. We and others have demonstrated that a TH1 response is necessary for protection against *Leishmania* infection. All animals responded well to ConA, a potent mitogen. Leish-111f+GLA-SE vaccination induced Leish-111f antigen-specific cytokine responses while no such responses were observed in the saline control group. When compared to ConA, Leish-111f+GLA-SE vaccination induced much more IFN-γ than IL-4, a TH1:TH2 ratio or phenotype associated with protection against the disease.

Example 11

Use of GLA-Containing Vaccine In Vivo

This example describes an in vivo model demonstrating an adjuvant effect of GLA in a vaccine containing a specific *Leishmania* antigen. Standard immunological methodologies and reagents were employed (Current Protocols in Immunology, Coligan et al. (Eds.) 2006 John Wiley & Sons, NY).

Mice (three Balb/c animals per group) were immunized three times at two-week intervals with saline or the Leish- 110f antigen (10 μg per animal for each immunization) formulated in a stable emulsion containing different amounts of (i) GLA (Avanti Polar Lipids, Inc., Alabaster, Ala.; product number 699800; 40, 5, or 1 μg per animal for each immunization) according to the procedure used in Example 3 above (GLA-SE), or (ii) MPL® (40, 5, or 1 μg per animal for each immunization) in an emulsion as supplied by the manufacturer ("MPL-SE", GSK Biologicals, Rixensart, Belgium). One week after the last injection, mice were sacrificed and spleen collected to analyze T cell-dependent IFN-γ cytokine responses to in vitro antigen stimulation by ELISA according to published methods (Id.). IFN-γ cytokine responses have been associated with a TH1 protective phenotype against Leishmania infection.

FIG. 6 shows ELISA data demonstrating levels of anti-Leish-110f IFN-γ cytokine production induced in mice one week after the third immunization using Leish-110f antigen formulated with different amounts of GLA, compared to saline controls. Means and SEM in each group are shown.

All animals responded well to ConA, a potent cell activator and mitogen. Leish-110f+GLA-SE vaccination induced Leish-110f antigen-specific cytokine responses, in a dose-dependent manner, while no such responses were observed in the saline control group. At all concentration tested, GLA-SE was more potent than MPL-SE, in inducing higher levels of IFN-γ☐ secreted by antigen-specific T cells.

In conclusion, the addition of GLA in a stable oil formulation to Leishmania vaccine antigen candidate Leish-110f induced predominantly antigen-specific immune responses of the cellular type (T cell) associated with the protective TH1 phenotype. In addition, GLA-SE was more potent than MPL-SE in inducing protection-associated cytokines like IFN-γ.

Example 12

Use of GLA-Containing Vaccine In Vivo

This example describes an in vivo model demonstrating an adjuvant effect of GLA in a vaccine containing a specific Leishmania antigen. Standard immunological methodologies and reagents were employed (Current Protocols in Immunology, Coligan et al. (Eds.) 2006 John Wiley & Sons, NY).

Mice (three Balb/c animals per group) were immunized three times at two-week intervals with saline or the Leish-110f antigen (10 μg per animal for each immunization) formulated in a stable emulsion containing different amounts of (i) GLA (Avanti Polar Lipids, Inc., Alabaster, Ala.; product number 699800; 20 μg or 5 μg per animal for each immunization) according to the procedure used in Example 3 above (GLA-SE), or (ii) MPL® (20 μg or 5 μg per animal for each immunization) in an emulsion as supplied by the manufacturer ("MPL-SE", GSK Biologicals, Rixensart, Belgium). One week after the last injection, mice were sacrificed and spleen collected to analyze T cell-dependent IFN-γ, IL-2, and TNF cytokine responses to in vitro antigen stimulation by intracellular cell staining (ICS) and Flow cytometry according to published methods (Id.). These three cytokines have been associated with a TH1 protective phenotype against Leishmania infection.

When analyzed at the single cell level, the frequency of CD4+ T cells expressing all three cytokines IFN-γ, IL-2, and TNF or a combination of IFN-γ and IL-2 was higher in the Leish-110f+GLA-SE group compared to the Leish-110f+ MPL-SE group, and this was observed at both 20 and 5 μg doses. It has been reported (Seder et al.) that high frequencies of CD4+ T cells expressing all three cytokines IFN-γ, IL-2, and TNF correlates with protection against Leishmania infection.

In conclusion, the addition of GLA in a stable oil formulation to Leishmania vaccine antigen candidate Leish-110f induced predominantly antigen-specific immune responses of the cellular type (T cell) associated with the protective TH1 phenotype. In addition, GLA-SE was more potent than MPL-SE in inducing protection-associated cytokines like IFN-γ, IL-2, and TNF.

Example 13

Use of GLA-Containing Vaccine In Vivo

This example describes an in vivo model demonstrating an adjuvant effect of GLA in a vaccine containing a specific Mycobacterium tuberculosis antigen. Standard immunological methodologies and reagents were employed (Current Protocols in Immunology, Coligan et al. (Eds.) 2006 John Wiley & Sons, NY).

Mice (three C57BL/6 animals per group) were immunized three times at three-week intervals with the ID83 antigen (8 μg per animal for each immunization) used alone or formulated in a stable emulsion containing GLA (Avanti Polar Lipids, Inc., Alabaster, Ala.; product number 699800; 20 μg per animal for each immunization, according to the procedure used in Example 3 above, GLA-SE). Sera were collected by bleeding animals one week after the third immunization, and serum levels of IgG1 and IgG2c antibodies specific for ID83 were examined by ELISA according to published methods (Id.) Predominance of either IgG1 or IgG2c antibody isotype is associated with TH2 or TH1 responses, respectively. It has been demonstrated that a TH1 response is necessary for protection against Mycobacterium tuberculosis infection.

Vaccination with ID83 alone induced predominantly antigen-specific IgG1 antibody. In contrast, ID83+GLA-SE vaccination induced higher antibody titers, and reverted the phenotype to a predominantly IgG2c antigen-specific antibody response, associated with protection against the disease.

Example 14

Use of GLA-Containing Vaccine In Vivo

This example describes an in vivo model demonstrating an adjuvant effect of GLA in a vaccine containing a specific Mycobacterium tuberculosis antigen. Standard immunological methodologies and reagents were employed (Current Protocols in Immunology, Coligan et al. (Eds.) 2006 John Wiley & Sons, NY).

Mice (three C57BL/6 animals per group) were immunized three times at three-week intervals with the ID83 antigen (8 μg per animal for each immunization) used alone or formulated in a stable emulsion containing GLA (GLA-SE), GLA+CpG ($CpG_{1826}$, Coley Pharmaceuticals, 25 μg) (GLA/CpG-SE), or GLA+Gardiquimod (GDQ) (Invivogen, 20 μg) (GLA/GDQ-SE). Three weeks after the last injection, mice were sacrificed and spleens collected to analyze CD4+ and CD8+ T cell-dependent IFN-γ, IL-2, and TNF cytokine responses to in vitro ID83 antigen stimulation by ICS and Flow cytometry according to published methods. Expression of IFN-γ, IL-2, and TNF cytokines have been associated with protective TH1 responses against M. tuberculosis infection.

FIG. 7 shows ICS data demonstrating the frequencies of ID83-specific IFN-γ, IL-2, and TNF cytokine producing CD4+ and CD8+ T cells induced in mice one week after the third immunization using ID83 alone or adjuvanted with formulations containing GLA (GLA-SE), GLA+CpG (GLA/CpG-SE), or GLA+GDQ (GLA/GDQ-SE).

Frequencies of ID83 specific cytokine producing CD4+ or CD8+ T cells were at background levels for the saline and ID83 alone vaccine groups. ID83 antigen specific cytokine producing T cells, both CD4+ and CD8+, were induced by ID83+GLA-SE vaccination, and their frequency further increased by the addition of a second TLR ligand like GDQ (TLR7/8) or CpG (TLR9). T cells expressing IFN-γ+ TNF or IFN-γ+IL-2 were the predominant populations.

In conclusion, adjuvanting an antigen against *M. tuberculosis* with GLA-SE greatly enhanced the antigen specific cellular response (T cells) as measured by the frequencies of T cells expressing IFN-γ, IL-2, and/or TNF cytokines. Combining GLA-SE with another TLR ligand further increased the frequency of antigen specific cytokine producing cells, a phenotype associated with protection against this disease.

Example 15

Use of GLA-Containing Vaccine In Vivo

This example describes an in vivo model demonstrating an adjuvant effect of GLA in a vaccine containing a specific *Mycobacterium leprae* antigen. Standard immunological methodologies and reagents were employed (Current Protocols in Immunology, Coligan et al. (Eds.) 2006 John Wiley & Sons, NY).

Mice (three C57BL/6 animals per group) were immunized three times at three-week intervals with the ML0276 antigen (10 μg per animal for each immunization) adjuvanted with aqueous formulations containing CpG (CpG$_{1826}$, Coley Pharmaceutical, 25 μg per animal for each immunization), or Imiquimod (IMQ) (3M Pharma, 25 μg per animal for each immunization), or GLA (Avanti Polar Lipids, Inc., Alabaster, Ala.; product number 699800; 25 μg per animal for each immunization according to the procedure used in Example 3 above, GLA-SE), a mix of the three, or saline as negative control. Sera were collected by bleeding animals three weeks after the second immunization, and serum levels of IgG antibodies specific for ML0276 were examined by ELISA according to published methods (Id.).

Animals from the saline control group did not show ML0276 specific IgG, and those from the ML0276+CpG and ML0276+IMQ groups showed a very low level of antigen specific antibody. In contrast, ML0276+GLA-SE induced a significant level of ML0276 specific IgG, that was further increased when the three adjuvants were used together.

In conclusion, the data support the adjuvanting effect of GLA-SE and/or a combination of GLA-SE with additional TLR ligands when used with antigen ML0276 for the induction of antigen specific antibodies.

Example 16

Use of GLA-Containing Vaccine In Vivo

This example describes an in vivo model demonstrating an adjuvant effect of GLA in a vaccine containing a specific *Mycobacterium leprae* antigen. Standard immunological methodologies and reagents were employed (Current Protocols in Immunology, Coligan et al. (Eds.) 2006 John Wiley & Sons, NY).

Mice (three C57BL/6 animals per group) were immunized three times at three-week intervals with the ML0276 antigen (10 μg per animal for each immunization) adjuvanted with aqueous formulations containing CpG (CpG$_{1826}$, Coley Pharmaceutical, 25 μg per animal for each immunization), or Imiquimod (IMQ) (3M Pharma, 25 μg per animal for each immunization), or GLA (Avanti Polar Lipids, Inc., Alabaster, Ala.; product number 699800; 25 μg per animal for each immunization, according to the procedure used in Example 3 above, GLA-SE), a mix of the three, or saline as negative control. Three weeks after the last injection, mice were sacrificed and spleen collected to analyze CD4+ T cell-dependent IFN-γ cytokine responses to in vitro ML0276 antigen stimulation by ICS and Flow cytometry according to published methods. Expression of IFN-γ cytokine has been associated with protective TH1 responses against *M. leprae* infection.

FIG. 8, panel A shows ICS data demonstrating the frequencies of ML0276-specific IFN-γ cytokine producing CD4+ T cells induced in mice one week after the third immunization using ML0276 antigen formulated with aqueous formulations containing CpG, or Imiquimod (IMQ), or a stable oil emulsion containing GLA (GLA-SE), or the three mixed together, compared to saline and naïve controls. Means in each group are shown. FIG. 8, panel B shows data demonstrating the cellularity of lymph nodes draining the site of *M. leprae* infection in mice immunized with ML0276 antigen formulated with aqueous formulations containing CpG, or Imiquimod (IMQ), or a stable oil emulsion containing GLA (GLA-SE), or a mixture of the three, compared to saline and naïve controls. Means and SEM in each group are shown.

Animals from the saline control group did not show ML0276 specific IFN-γ responses with a background frequency of 0.04% positive cells. Those from the CpG and IMQ groups showed a slightly increased frequency of antigen specific cytokine producing cells with 0.17% and 0.11% respectively. In contrast, a significantly higher number of ML0276 specific IFN-γ+CD4+ T cells (0.66%) were observed when GLA-SE was used as an adjuvant, a frequency that was further increased when the three adjuvants were mixed together (2.14%).

A subset of mice was subsequently challenged with *M. leprae* and found to be protected by ML0276+GLA-SE as measured by the reduction in the number of cells in the lymph nodes draining the site of challenge as compared to infected saline controls. Vaccination with ML0276+CpG and ML0276+IMQ induced only a modest decrease in cell numbers compared to saline.

In conclusion, the data support the adjuvanting effect of GLA-SE and/or a combination of GLA-SE with additional TLR ligands when used with antigen ML0276 for the induction of antigen specific cellular responses.

Example 17

GLA Stimulation of Human Dendritic Cells

This example describes an in vitro model demonstrating an adjuvant effect of GLA. Standard tissue culture methodologies and reagents were employed.

Dendritic cells were derived from purified blood CD14+ monocytes following a published protocol. Various adjuvant concentrations of either synthetic GLA (Avanti Polar Lipids, Inc., Alabaster, Ala.; product number 699800) or the natural product MPL® (GSK Biologicals, Rixensart, Belgium) were achieved by diluting an aqueous adjuvant preparation in cell culture medium (RPMI containing 5% human serum). Prior to collection and analysis of the expression of activation markers, cells were maintained for 44 hours at 37° C. in a humidified atmosphere containing 5% $CO_2$. Expression levels of the costimulatory molecule CD86 at the surface of DC were used as an indicator of cell activation and measured by flow cytometry on a LSRII instrument (BD Biosciences, San Jose, Calif.) using CD86-specific fluorochrome-labeled antibody (eBiosciences, San Diego, Calif.) according to the manufacturer's instructions.

FIG. 9 shows data obtained by flow cytometry demonstrating levels of CD86 molecule expressed at the surface of human DC in response to 44 h of stimulation with 10,000 ng/ml to 0.010 ng/ml GLA (panel A) or MPL (panel B). A positive stimulation control consisting of PGE2, IL-1β, TNF, and IL-6 was also included.

GLA-AF induced a dose-dependent immune response in the human primary DC (FIG. 9, panel A), characterized by the increased expression of CD86. Maximal CD86 expression was seen with GLA at 10,000 ng/ml, 1000 ng/ml, and 100 ng/ml, while MPL had only maximal expression at 10,000 ng/ml and 1000 ng/mL with DCs generated from Donor N003. An additional three donors were used to generate DC cultures and evaluated in a similar manner with GLA and MPL stimulation at 1000 ng/ml to 1 ng/mL, see FIG. 10. The dendritic cells from these donors showed different levels of sensitivity, but in every case lower doses of GLA achieved higher CD86 expression than MPL. This demonstrated that GLA was active at concentrations at least 10-fold lower compared to MPL for human dendritic cell maturation.

Example 18

Use of GLA-Containing Vaccine In Vivo

This example describes an in vivo model demonstrating an adjuvant effect of GLA in a vaccine containing a specific *Leishmania* antigen. Standard immunological methodologies and reagents were employed (*Current Protocols in Immunology*, Coligan et al. (Eds.) 2006 John Wiley & Sons, NY).

Four Balb/c mice per treatment group were immunized three times at two-week intervals either with saline or the Leish-110f antigen (10 µg per animal for each immunization) formulated in a stable emulsion containing 20 µg of (i) GLA (Avanti Polar Lipids, Inc., Alabaster, Ala.; product number 699800; per animal for each immunization) according to the procedure used in Example 3 above (GLA-SE), or (ii) MPL® in an emulsion as supplied by the manufacturer ("MPL-SE", GSK Biologicals, Rixensart, Belgium, per animal for each immunization). Three weeks after the last injection, mice were challenged intradermally in the pinea of both ears with $2 \times 10^3$ purified *Leishmania major* clone V1 (MOHM/IL/80/Friedlin) metacyclic promastigotes according to published methods (Id.). Development of cutaneous lesions was monitored weekly for 6 weeks post-infection.

FIG. 11 shows diameter of lesions in mice immunized using Leish-110f antigen formulated with GLA-SE or MPL-SE, compared to saline controls. Means in each group are shown.

All animals in the saline control groups developed progressive non-healing lesions. Ear lesions that started to develop during the first 2 weeks, were controlled at week 3, and eventually resolved by week 4 in mice immunized with Leish-110f+GLA-SE. Lesions of mice immunized with Leish-110f+MPL-SE were reduced compared to the saline group but did not resolve. GLA-SE was more potent than MPL-SE in preventing the development of lesions.

In conclusion, the addition of GLA in a stable oil formulation to *Leishmania* vaccine antigen candidate Leish-110f prevented the development of cutaneous lesions upon challenge with *Leishmania major* parasites. In addition, GLA-SE was more potent than MPL-SE in controlling lesion development.

Example 19

Use of GLA-Containing Vaccine In Vivo

This example describes an in vivo model demonstrating an adjuvant effect of GLA in a vaccine containing a specific *Leishmania* antigen. Standard immunological methodologies and reagents were employed (*Current Protocols in Immunology*, Coligan et al. (Eds.) 2006 John Wiley & Sons, NY).

Four Balb/c mice per treatment group were immunized three times at two-week intervals with saline or the Leish-110f antigen (10 µg per animal for each immunization) formulated in a stable emulsion containing 20 µg of (i) GLA (Avanti Polar Lipids, Inc., Alabaster, Ala.; product number 699800; per animal for each immunization) according to the procedure used in Example 3 above (GLA-SE), or (ii) MPL® in an emulsion as supplied by the manufacturer ("MPL-SE", GSK Biologicals, Rixensart, Belgium, per animal for each immunization). Three weeks after the last injection, mice were challenged intradermally in the pinea of both ears with $2 \times 10^3$ purified *Leishmania major* clone V1 (MOHM/IL/80/Friedlin) metacyclic promastigotes according to published methods (Id.). Parasite burden in the ear and draining lymph nodes of infected mice were determined 6 weeks post-infection.

FIG. 12 shows the number of parasites recovered in the ear and draining lymph nodes of mice immunized using Leish-110f antigen formulated with GLA-SE or MPL-SE, compared to saline controls. Number of parasites in individual organs and means in each group are shown. Differences in parasite numbers between groups were evaluated for statistical significance using the Student's t test. A difference was considered significant when the p value was <0.05.

Animals in the saline control groups showed an average parasite load of $10^5$ and $5 \times 10^4$ in ears and draining lymph nodes respectively. In mice immunized with Leish-110f+GLA-SE, no parasites could be detected in 8/8 ears and in 6/8 draining lymph nodes. In contrast, in mice immunized with Leish-110f+MPL-SE, no parasites could be detected in 4/8 ears and 2/8 draining lymph nodes. GLA-SE was more potent than MPL-SE in controlling infection with *Leishmania major*.

In conclusion, the addition of GLA in a stable oil formulation to *Leishmania* vaccine antigen candidate Leish-110f controlled parasite burden in both ear and draining lymph nodes upon challenge with *Leishmania major* parasites. In addition, GLA-SE was more potent than MPL-SE in controlling the number of parasites recovered from the infected tissues.

Example 20

Use of GLA-Containing Vaccine In Vivo

This example describes an in vivo model demonstrating an adjuvant effect of GLA in a lentiviral vaccine containing OVA antigen. Standard immunological methodologies and reagents were employed (*Current Protocols in Immunology*, Coligan et al. (Eds.) 2006 John Wiley & Sons, NY).

Five C57BL/6 mice per treatment group were immunized one time with saline, the lentiviral vaccine or the lentiviral vaccine administered at the same time as a stable emulsion containing 20 µg of GLA (Avanti Polar Lipids, Inc., Alabaster, Ala.; product number 699800; per animal for each immunization) according to the procedure used in Example 3 above (GLA-SE). Two weeks after the injection, splenocytes were removed and T cell immunogenicity (phenotype and effector functions) was evaluated by multiparameter flow cytometry.

Splenocytes were plated in 24-well plates and stimulated ex vivo overnight with 2 µg/ml anti-CD28 (eBioscience, San Diego, Calif.), anti-CD49d (eBioscience), and 20 µg/ml OVA as antigen (or with PMA/ionomycin, or without antigen as a negative control) in complete media at 37° C. After a 2 hour incubation at 37° C., brefeldin A (GolgiPlug: BD Biosciences, San Jose, Calif.) was added to the wells and the incubation resumed for an additional 12 hrs at 37° C. Cells were blocked with anti-CD16/32 (eBioscience) 1:50 in 50 µl and then stained with AlexaFluor 700-anti-CD3 (eBioscience), PerCP-anti-CD4 (BD Biosciences), and PE-anti-CD8 (BD Biosciences). The cells were fixed using the Cytofix/Cytoperm kit (BD Biosciences) and intracellular staining was performed according to the BD Biosciences protocol. Cells were blocked with anti-CD16/32 and intracellularly stained with FITC-anti-TNF-α (eBioscience), Pacific Blue-anti-IL-2 (eBioscience) and PE-Cy7-anti-IFN-γ (BD Biosciences). Cells were analyzed with a LSRII FACS machine (BD Biosciences) and the DIVA software to quantify CD4+ T cells producing IFN-γ, IL-2 and TNF-α.

FIG. 13 shows CD8 (panels A-C) and CD4 (panels D-F) responses in mice immunized with the lentivirus vaccine expressing OVA antigen in the presence and absence of GLA-SE, compared to saline controls. Means in each group are shown.

Splenocytes from animals in the lentivector vaccine plus GLA-SE had higher percentages of CD8+CD44+ as well as CD4+CD44+ cytokine secreting cells than splenocytes from animals receiving the lentivaccine alone. The addition of GLA-SE to the lentivaccine immunization resulted in an increased frequency of antigen-specific triple cytokine (IFN-γ, TNF-α, IL-2) producing T cells.

In conclusion, the addition of GLA in a stable oil formulation to the lentiviral vector vaccine improved both the quantity and quality of effector T cells which may have an essential role in protection against a variety of infections.

Example 21

Use of GLA-Containing Vaccine In Vivo

This example describes an in vivo model demonstrating an adjuvant effect of GLA-SE in a vaccine against Influenza. Standard immunological methodologies and reagents were employed (e.g., *Current Protocols* in Immunology, Coligan et al. (Eds.) 2006 John Wiley & Sons, NY).

Three Balb/c mice treatment group were immunized i.d. with microneedles (NanoPass Technologies Ltd., Nes Ziona, Israel) 2 times at 3 week intervals (total volume was 100 µl; 50 µl per hind leg) with i) a stable emulsion containing GLA, "GLA-SE", (Avanti Polar Lipids, Inc., Alabaster, Ala.; product number 699800; 5 µg per animal for each immunization) and Fluzone® (Sanofi Pasteur, Stillwater Pa.; 2 µg and 0.2 µg treatment groups); ii) stable emulsion (SE) plus Fluzone; or iii) Fluzone only. Mice were immunized with the 2006-2007 commercial Fluzone formula which includes components from A/New Caledonia/20/99 (H1N1), A/Wisconsin/67/2005 (H3N2), and B/Malaysia/2506/2004. Mice were bled one week after the second immunization and serum was analyzed for antibody responses to Fluzone.

IgG2a responses were dominant in mice immunized using Fluzone combined with GLA-SE. One week following a boost immunization, significantly greater levels of anti-Fluzone antibodies (total IgG and IgG2a) were induced in this treatment group (see FIG. 14, panels A-B). IgG1 antibody levels were similar in all treatment groups (see FIG. 14, panel C). A significant increase in endpoint antibody titers were seen in mice that received a boost immunization of Fluzone plus GLA-SE as compared to mice that received a boost immunization of Fluzone vaccine alone (e.g., FIG. 14, compare "GLA-SE" treatment group (Fluzone plus GLA-SE) with "(–)" treatment group (Fluzone)). No differences in antibody titers were observed in mice that received a boost immunization of Fluzone combined with a stable emulsion (SE) as compared to mice that received a boost immunization of Fluzone vaccine alone (e.g., FIG. 14, compare "SE" treatment group (Fluzone plus SE) with "(–)" treatment group (Fluzone)).

Total IgG and IgG2a antibody titers were enhanced in response to Fluzone vaccination combined with GLA-SE. The adjuvanting effect of GLA-SE was similar for both the 2 µg and 0.2 ug doses of Fluzone vaccine in combination with GLA-SE. These results suggest that it is possible to reduce the dose of Fluzone vaccine by adjuvanting it with GLA-SE, and still induce high levels of IgG and IgG2a antibody titers.

Example 22

Use of GLA-Containing Vaccine In Vivo

This example describes an in vivo model demonstrating an adjuvant effect of GLA-SE in a vaccine against Influenza. Standard immunological methodologies and reagents were employed (Current Protocols in Immunology, Coligan et al. (Eds.) 2006 John Wiley & Sons, NY).

Three Balb/c mice treatment group were immunized i.m. 2 times at 3 week intervals (total volume was 100 µl; 50 µl per hind leg) with i) a stable emulsion containing GLA, "GLA-SE", (Avanti Polar Lipids, Inc., Alabaster, Ala.; product number 699800; 5 µg per animal for each immunization) and Fluzone® (Sanofi Pasteur, Stillwater Pa.; 0.2 µg); ii) stable emulsion (SE) plus Fluzone; iii) Fluzone only; or iv) saline. Mice were immunized with the 2006-2007 commercial Fluzone formula which includes components from A/New Caledonia/20/99 (H1N1), A/Wisconsin/67/2005 (H3N2), and B/Malaysia/2506/2004. Spleens were harvested three weeks following an i.m. boost with saline, Fluzone alone, Fluzone plus SE, or Fluzone plus GLA-SE.

Splenocytes were plated in 48-well plates and were stimulated ex vivo with H1N1 antigen (Influenza virus A H1N1, New Caledonia, Fitzgerald Industries, Concord Mass.) or media (e.g., negative control) and supernatants were collected 72 hours later. Supernatants were assayed for soluble murine cytokines including IFN-gamma, IL-2, IL-10 and IL-5, using specific sandwich ELISA assay kits (eBiosciences, San Diego, Calif.) according to the manufacturer's instructions.

Mice immunized using Fluzone (0.2 µg) plus GLA-SE (5 µg) had significantly higher levels of IFN-γ and IL-2 cytokines following H1N1 antigen stimulation of splenocytes as compared to unstimulated controls (FIG. 15). Furthermore, treatment groups ii-iv failed to show significant increases in IFN-γ and IL-2 after H1N1 antigen stimulation. In contrast, mice immunized with Fluzone (0.2 µg) and SE displayed a different cytokine profile e.g., significantly higher levels of IL-5 and IL-10 as compared to other treatment groups.

These results indicate that mice immunized with Fluzone plus GLA-SE induced a significant Th$_1$ type T-cell cytokine response compared to other treatment groups. Th$_1$ cytokine responses are believed have an essential role in protection against a variety of infections.

Example 23

USP Rabbit Pyrogen Test

GLA and MPL were evaluated for pyrogenicity/toxicity using the United States Pharmacopeial (USP) rabbit pyrogen test method. GLA was tested at the same doses and conditions commonly used for MPL. Both GLA and MPL passed the USP<151> requirements for the absence of pyrogens at the doses evaluated. These data indicate that the unexpected high potency of GLA compared to MPL is not associated with increased toxicity. Accordingly, lower doses of GLA can be used to achieve the same or improved potency relative to MPL while also having correspondingly reduced pyrogenicity due to the lower doses needed.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of eliciting or enhancing a desired antigen-specific immune response in a subject, the method comprising administering to the subject a composition comprising:
    (a) at least one recombinant expression construct which comprises a promoter operably linked to a nucleic acid sequence encoding at least one polypeptide antigen; and
    (b) a synthetic, substantially homogenous glucopyranosyl lipid adjuvant (GLA), wherein the GLA has the formula:

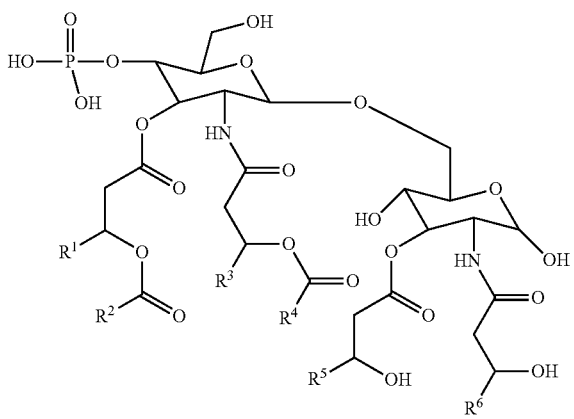

where:
    $R^1$, $R^3$, $R^5$ and $R^6$ are $C_{11}$ alkyl; and
    $R^2$ and $R^4$ are $C_{13}$ alkyl.

2. The method of claim 1 wherein the at least one polypeptide antigen is derived from, or is immunologically cross-reactive with, (i) at least one infectious pathogen that is associated with an infectious disease, (ii) at least one epitope, biomolecule, cell or tissue that is associated with a cancer, or (iii) at least one epitope, biomolecule, cell or tissue that is associated with an autoimmune disease, and thereby eliciting or enhancing a desired antigen-specific immune response.

3. The method of claim 1, wherein the composition further comprises at least one additional component selected from the group consisting of:
    (a) a toll-like receptor (TLR) agonist;
    (b) a saponin or saponin mimetic;
    (c) a carrier that comprises at least one of an oil and ISCOMATRIX™;
    (d) an imidazoquinoline immune response modifier;
    (e) a double stem loop immune modifier (dSLIM);
    (f) a co-adjuvant; and
    (g) a pharmaceutically acceptable carrier.

4. The method of claim 3 wherein:
    (i) the co-adjuvant, when present, is selected from the group consisting of alum, a plant alkaloid and a detergent, wherein the plant alkaloid is selected from tomatine and the detergent is selected from saponin, Polysorbate 80, Span 85 and Stearyl tyrosine,
    (ii) the TLR agonist, when present, is selected from the group consisting of lipopolysaccharide, peptidoglycan, polyI:C, CpG, 3M003, flagellin, Leishmania homolog of eukaryotic ribosomal elongation and initiation factor 4a (LeIF) and at least one hepatitis C antigen,
    (iii) the imidazoquinoline immune response modifier, when present, is selected from the group consisting of resiquimod (R848), imiquimod and gardiquimod,
    (iv) the co-adjuvant, when present, is selected from the group consisting of a cytokine, a detergent, and a block copolymer or biodegradable polymer, and
    (v) the pharmaceutically acceptable carrier, when present, comprises a carrier that is selected from the group consisting of calcium phosphate, an oil-in-water emulsion, a water-in-oil emulsion, a liposome, and a microparticle.

5. The method of claim 1 wherein the GLA is capable of inducing an immune response that is more potent that an immune response induced using MPL.

6. The method of claim 1 wherein the GLA is active at a concentration at least 5-fold lower than MPL.

7. The method of claim 1 wherein the recombinant expression construct comprises a viral vector.

8. The method of claim 7 wherein the viral vector is selected from the group consisting of an adenovirus vector, an adeno-associated virus vector, a herpesvirus vector, a lentivirus vector, a poxvirus vector and a retrovirus vector.

9. The method of claim 1 wherein the at least one polypeptide antigen is derived from, or is immunologically cross-reactive with, (i) at least one infectious pathogen that is associated with an infectious disease, (ii) at least one epitope, biomolecule, cell or tissue that is associated with the cancer or (iii) at least one epitope, biomolecule, cell or tissue that is associated with an autoimmune disease.

* * * * *